(12) United States Patent
Benitez-Marzan et al.

(10) Patent No.: US 11,332,787 B2
(45) Date of Patent: May 17, 2022

(54) METHODS AND COMPOSITIONS FOR DELIVERY OF MOLECULES AND COMPLEXES TO REACTION SITES

(71) Applicant: Pacific Biosciences of California, Inc., Menlo Park, CA (US)

(72) Inventors: Jaime Juan Benitez-Marzan, Fremont, CA (US); Natasha Popovich, Belmont, CA (US); Lei Sun, San Jose, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 501 days.

(21) Appl. No.: 16/456,867

(22) Filed: Jun. 28, 2019

(65) Prior Publication Data
US 2020/0002765 A1    Jan. 2, 2020

Related U.S. Application Data

(60) Provisional application No. 62/692,234, filed on Jun. 29, 2018, provisional application No. 62/837,159, filed on Apr. 22, 2019.

(51) Int. Cl.
*C12Q 1/6874* (2018.01)
*B01J 19/00* (2006.01)

(52) U.S. Cl.
CPC ........ *C12Q 1/6874* (2013.01); *B01J 19/0046* (2013.01)

(58) Field of Classification Search
None
See application file for complete search history.

(56) References Cited

U.S. PATENT DOCUMENTS

| | | |
|---|---|---|
| 5,328,824 A | 7/1994 | Ward et al. |
| 5,476,928 A | 12/1995 | Ward et al. |
| 6,001,611 A | 12/1999 | Will |
| 6,056,661 A | 5/2000 | Schmidt |
| 6,917,726 B2 | 7/2005 | Levene et al. |
| 7,033,764 B2 | 4/2006 | Korlach et al. |
| 7,041,812 B2 | 5/2006 | Kumar et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,302,146 B2 | 11/2007 | Turner et al. |
| 7,313,308 B2 | 12/2007 | Turner et al. |

(Continued)

FOREIGN PATENT DOCUMENTS

| | | |
|---|---|---|
| WO | 2007041342 A2 | 4/2007 |
| WO | 2007075987 A2 | 7/2007 |

(Continued)

OTHER PUBLICATIONS

International Search Report and Written Opinion dated Oct. 29, 2019 from related case PCT/US2019/039846.

(Continued)

*Primary Examiner* — Kaijiang Zhang
(74) *Attorney, Agent, or Firm* — Monicia Elrod-Erickson

(57) ABSTRACT

The present invention provides methods, compositions, and systems for distributing molecules and complexes into reaction sites. In particular, the methods, compositions, and systems of the present invention result in loading of polymerase enzyme complexes into a predetermined number of reaction sites, including nanoscale wells.

15 Claims, 29 Drawing Sheets

Specification includes a Sequence Listing.

(56) References Cited

U.S. PATENT DOCUMENTS

| | | | |
|---|---|---|---|
| 7,315,019 | B2 | 1/2008 | Turner et al. |
| 7,361,466 | B2 | 4/2008 | Korlach et al. |
| 7,476,504 | B2 | 1/2009 | Turner |
| 7,745,116 | B2 | 6/2010 | Williams |
| 7,763,423 | B2 | 7/2010 | Roitman et al. |
| 7,907,800 | B2 | 3/2011 | Foquet et al. |
| 7,968,702 | B2 | 6/2011 | Wegener et al. |
| 7,993,895 | B2 | 8/2011 | Eid et al. |
| 7,998,717 | B2 | 8/2011 | Eid et al. |
| 8,071,346 | B2 | 12/2011 | Eid et al. |
| 8,153,375 | B2 | 4/2012 | Travers et al. |
| 8,236,499 | B2 | 8/2012 | Patel et al. |
| 8,252,911 | B2 | 8/2012 | Bjornson et al. |
| 8,324,914 | B2 | 12/2012 | Chen et al. |
| 8,389,676 | B2 | 3/2013 | Christians |
| 8,501,405 | B2 | 8/2013 | Korlach et al. |
| 8,530,164 | B2 | 9/2013 | Patel et al. |
| 8,652,781 | B2 | 2/2014 | Korlach et al. |
| 8,669,374 | B2 | 3/2014 | Shen et al. |
| 8,715,930 | B2 | 5/2014 | Pham et al. |
| 8,802,600 | B2 | 8/2014 | Rank et al. |
| 8,889,886 | B2 | 11/2014 | Yue et al. |
| 8,906,612 | B2 | 12/2014 | Shen et al. |
| 8,906,670 | B2 | 12/2014 | Gray et al. |
| 8,906,831 | B2 | 12/2014 | Eid et al. |
| 8,975,216 | B2 | 3/2015 | Rank et al. |
| 8,986,930 | B2 | 3/2015 | Fedorov et al. |
| 8,993,307 | B2 | 3/2015 | Zaccarin et al. |
| 8,994,946 | B2 | 3/2015 | McCaffrey et al. |
| 9,051,263 | B2 | 6/2015 | Shen |
| 9,062,091 | B2 | 6/2015 | Bjornson et al. |
| 9,175,342 | B2 | 11/2015 | Jue et al. |
| 9,399,766 | B2 | 7/2016 | Kamtekar et al. |
| 9,547,003 | B2 | 1/2017 | Howarth |
| 9,637,782 | B2 | 5/2017 | Shen et al. |
| 9,957,291 | B2 | 1/2018 | Sebo et al. |
| 2003/0044781 | A1 | 3/2003 | Korlach et al. |
| 2003/0124576 | A1 | 7/2003 | Kumar et al. |
| 2007/0036511 | A1 | 2/2007 | Lundquist et al. |
| 2007/0072196 | A1 | 3/2007 | Xu et al. |
| 2007/0196846 | A1 | 8/2007 | Hanzel et al. |
| 2008/0032301 | A1 | 2/2008 | Rank et al. |
| 2008/0108082 | A1 | 5/2008 | Rank et al. |
| 2009/0208957 | A1 | 8/2009 | Korlach et al. |
| 2009/0208961 | A1 | 8/2009 | Bjornson et al. |
| 2009/0298075 | A1 | 12/2009 | Travers |
| 2010/0003765 | A1 | 1/2010 | Dixon et al. |
| 2010/0075332 | A1 | 3/2010 | Patel et al. |
| 2010/0093555 | A1 | 4/2010 | Bjornson et al. |
| 2010/0112645 | A1 | 5/2010 | Clark et al. |
| 2010/0136592 | A1 | 6/2010 | Kong |
| 2010/0152424 | A1 | 6/2010 | Korlach et al. |
| 2010/0167299 | A1 | 7/2010 | Korlach |
| 2010/0221716 | A1 | 9/2010 | Flusberg et al. |
| 2011/0059505 | A1 | 3/2011 | Hanzel et al. |
| 2011/0183320 | A1 | 7/2011 | Flusberg et al. |
| 2011/0189659 | A1 | 8/2011 | Clark et al. |
| 2011/0244447 | A1 | 10/2011 | Korlach |
| 2011/0256618 | A1 | 10/2011 | Eid et al. |
| 2012/0014837 | A1 | 1/2012 | Fehr et al. |
| 2012/0019828 | A1 | 1/2012 | McCaffrey et al. |
| 2012/0021525 | A1 | 1/2012 | Fehrt et al. |
| 2012/0034602 | A1 | 2/2012 | Emig et al. |
| 2012/0052488 | A1 | 3/2012 | Yue et al. |
| 2012/0085894 | A1 | 4/2012 | Zhong et al. |
| 2013/0217007 | A1 | 8/2013 | Kamtekar et al. |
| 2013/0244340 | A1 | 9/2013 | Davis et al. |
| 2013/0264207 | A1 | 10/2013 | Ju et al. |
| 2013/0327644 | A1 | 12/2013 | Turner et al. |
| 2014/0051068 | A1 | 2/2014 | Cherf et al. |
| 2014/0094374 | A1 | 4/2014 | Kamtekar et al. |
| 2014/0094375 | A1 | 4/2014 | Kamtekar et al. |
| 2014/0134616 | A1 | 5/2014 | David et al. |
| 2014/0315756 | A1 | 10/2014 | Rank et al. |
| 2015/0065353 | A1 | 3/2015 | Turner et al. |
| 2015/0086994 | A1 | 3/2015 | Williams et al. |
| 2016/0168634 | A1* | 6/2016 | Rearick et al. ...... C12Q 1/6874 506/2 |
| 2016/0310926 | A1 | 10/2016 | Sun et al. |
| 2017/0037462 | A1 | 2/2017 | Turner et al. |
| 2017/0136433 | A1 | 5/2017 | Sun et al. |
| 2017/0145494 | A1 | 5/2017 | Yue et al. |
| 2017/0145495 | A1 | 5/2017 | Sebo et al. |
| 2017/0145496 | A1 | 5/2017 | Sebo et al. |
| 2017/0159119 | A1 | 6/2017 | Sheikholeslami et al. |
| 2017/0184580 | A1 | 6/2017 | Shen et al. |
| 2017/0321268 | A1 | 11/2017 | Shen et al. |
| 2017/0356041 | A1 | 12/2017 | Miller et al. |
| 2018/0023134 | A1 | 1/2018 | Hanes et al. |
| 2018/0057870 | A1 | 3/2018 | Gremyachinskiy et al. |

FOREIGN PATENT DOCUMENTS

| | | | | |
|---|---|---|---|---|
| WO | 2007076057 | A2 | 7/2007 | |
| WO | 2007123763 | A2 | 11/2007 | |
| WO | 2008051530 | A2 | 5/2008 | |
| WO | 2009077734 | A2 | 6/2009 | |
| WO | 2009114182 | A2 | 9/2009 | |
| WO | WO-2010037085 | A1 * | 4/2010 | ......... G01N 27/4145 |
| WO | 2012042226 | A2 | 4/2012 | |
| WO | 2012083249 | A2 | 6/2012 | |
| WO | 2012129242 | A2 | 9/2012 | |
| WO | 2017087702 | A1 | 5/2017 | |

OTHER PUBLICATIONS

International Preliminary Report on Patentability dated Jan. 7, 2021 from related case PCT/US2019/039846.

Alba, "Protein Family Review: Replicative DNA Polymerases" Genome Biology (2001) 2(1):reviews 3002.1-3002.4.

Berman et al., "Structures of phi29 DNA polymerase complexed with substrate: The mechanism of translocation in B-family polymerases" EMBO J. (2007) 26:3494-3505.

Brune et al., "Dual Plug-and-Display Synthetic Assembly Using Orthogonal Reactive Proteins for Twin Antigen Immunization" Bioconjugate Chem. (2017) 28:1544-1551.

Burgers et al., "Eukaryotic DNA polymerases: proposal for a revised nomenclature" J Biol Chem. (2001) 276(47):43487-90.

Chen et al., "The history and advances of reversible terminators used in new generations of sequencing technology" Genomics Proteomics Bioinformatics (2013) 11:34-40.

Clarke et al., "Continuous base identification for single-molecule nanopore DNA sequencing" Nature Nanotechnology (2019) 4:265-270.

Di Mascio et al., "Carotenoids, Tocopherols and Thiols as Biological Singlet Molecular Oxygen Quenchers," Biochem Soc. Trans. Dec. 1990; 18(6): 1054-6.

Driscoll, R. J., et al., "Atomic-Scale Imaging of DNA Using Scanning Tunneling Microscopy." Nature (1990) 346(6281):294-296.

Eid et al., "Real-Time DNA Sequencing From Single Polymerase Molecules," Science (2009) 323:133-138.

Fairhead et al., "SpyAvidin hubs enable precise and ultrastable orthogonal nanoassembly" J. Am. Chem. Soc. (2014) 136: 12355-12363.

Feng et al., "Nanopore-based Fourth-generation DNA Sequencing Technology" Genomics, Proteomics & Bioinformatics (2015) 13:4-16.

Fuller et al., "Real-time single-molecule electronic DNA sequencing by synthesis using polymer-tagged nucleotides on a nanopore array" Proc Natl Acad Sci USA (2016) 113:5233-5238.

Glatthar et al., "A new photocleavable Linker in solid-phase chemistry for ether cleavage," Org. Lett. (2000) 2(15):2315-2317.

Goodwin, P. M., et al., "Application of Single Molecule Detection to DNA Sequencing," Nucleosides & Nucleotides (1997) 16(5-6): 543-550.

Howorka, S., et al., "Sequence-Specific Detection of Individual DNA Strands using Engineered Nanopores," Nature Biotechnology (2001) 19(7): 636-639.

(56) References Cited

OTHER PUBLICATIONS

Hübscher et al., "Eukaryotic DNA Polymerases" Annual Review of Biochemistry (2002) vol. 71: 133-163.
Kadina et al., "RNA Cloaking by Reversible Acylation," Angew Chem Int Ed Engl. Mar. 12, 2018; 57(12):3059-3063.
Kamtekar et al., "Insights into strand displacement and processivity from the crystal structure of the protein-primed DNA polymerase of bacteriophage ϕ29" Mol. Cell (2004) 16(4): 609-618.
Kamtekar et al., "The phi29 DNA polymerase:protein-primer structure suggests a model for the initiation to elongation transition," EMBO J. (2006) 25(6):1335-43.
Korlach et al., "Long, Processive Enzymatic DNA Synthesis Using 100% Dye-Labeled Terminal Phosphate-Linked Nucleotides," Nucleosides, Nucleotides and Nucleic Acids (2008) 27:1072-1083.
Korlach et al., "Real-time DNA sequencing from single polymerase molecules" Methods Enzymol. (2010) 472:431-55.
Korlach et al., "Selective aluminum passivation for targeted immobilization of single DNA polymerase molecules in zero-mode waveguide nanostructures," Proc Natl Acad Sci (2008) 105(4)1176-1181.
Levene et al., "Zero-mode Waveguides for Single-molecule Analysis at High Concentration," Science (2003) 299:682-686.
Lundquist et al., "Parellel Confocal Detection of Single Molecules in Real Time," Optics Letters (2008) 33(9):1026-1028.
Meller, A., et al., "Rapid Nanopore Discrimination Between Single Polynucleotide Molecules," Proceedings of the National Academy of Sciences of the United States of America (2000) 97(3): 1079-1084.
Rigler, et al., "DNA-Sequencing at the Single Molecule Level," Journal of Biotechnology (2001) 86(3): 161.
Rodebaugh, et al., "A New-Nitrobenzyl Photocleavable Linker for Solid Phase Synthesis," Tetrahedron Lett. (1997) 38(44):7653-7656.
Sano and Cantor, "Expression of a cloned streptavidin gene in *Escherichia coli*," Proc Natl Acad Sci USA 87:142-6.
Stahl et al., "Biological activities of natural and synthetic carotenoids: induction of gap junctional communication and singlet oxygen quenching," Carcinogenesis vol. 18 No. 1 pp. 89-92, 1997.
Steitz, "DNA polymerases: structural diversity and common mechanisms," J Biol Chem (2008) 274:17395-17398.
Travers et al., "A flexible and efficient template format for circular consensus sequencing and SNP detection" Nucl. Acids Res. (2010) 38(15):e159.
Veggiani et al., "Programmable polyproteams built using twin peptide superglues," Proc Natl Acad Sci USA (2016) 113(5):1202-7.
Yan et al., "Synthesis and Characterization of a Photocleavable Cross-Linker and Its Application on Tunable Surface Modification and Protein Photodelivery," Bioconjugate Chem. (2004) 15(5): 1030-1036.
Zakeri et al., "Peptide tag forming a rapid covalent bond to a protein, through engineering a bacterial adhesin" Proc Natl Acad Sci USA (2012) 109(12):E690-7.
EP Search Report dated Mar. 9, 2022 from related EP 19825049.0.

* cited by examiner

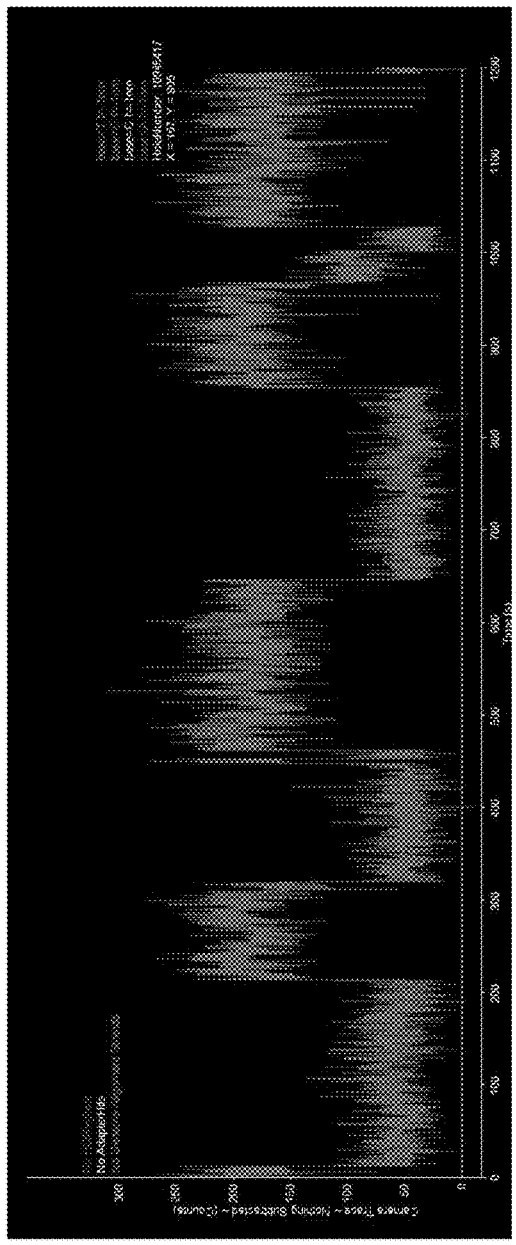
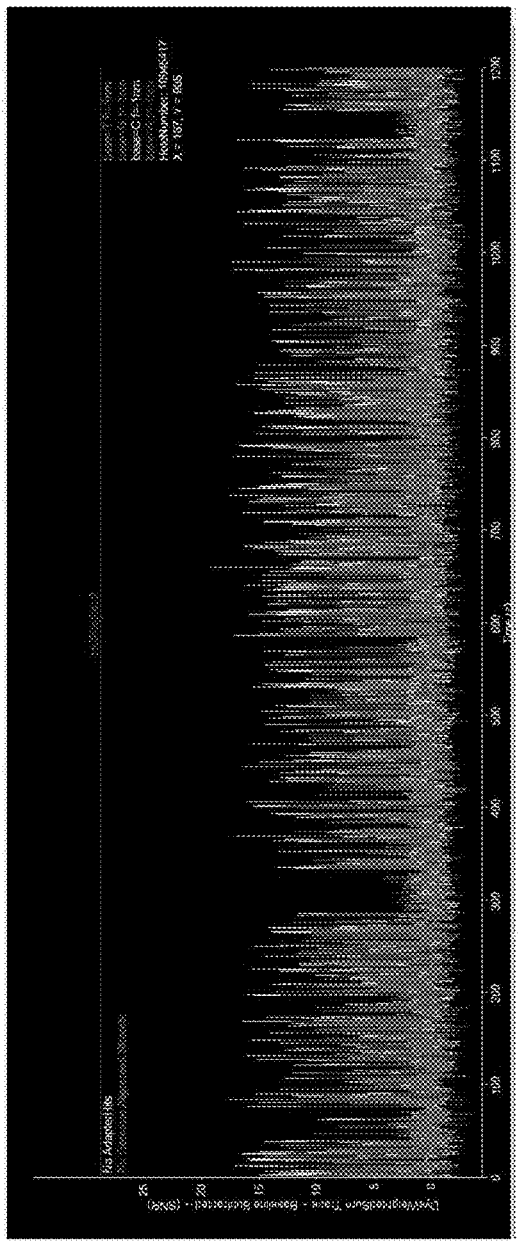
Fig. 2A
Fig. 2B

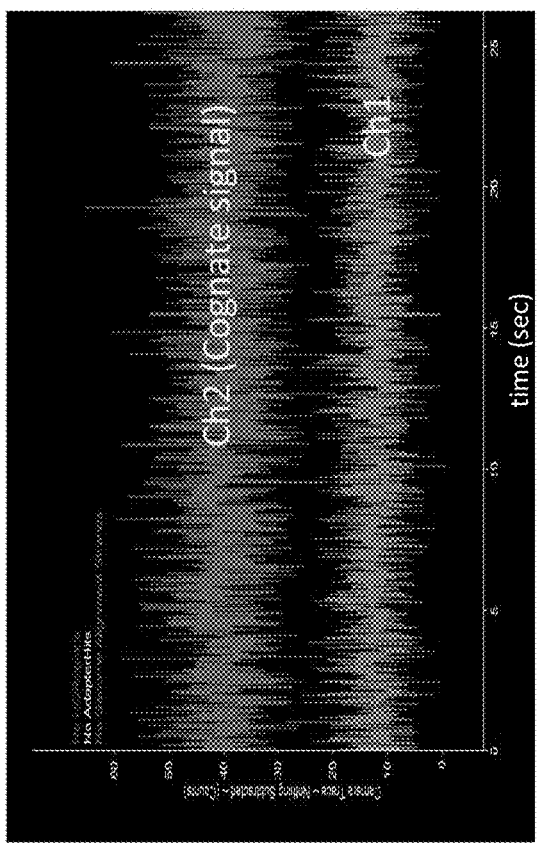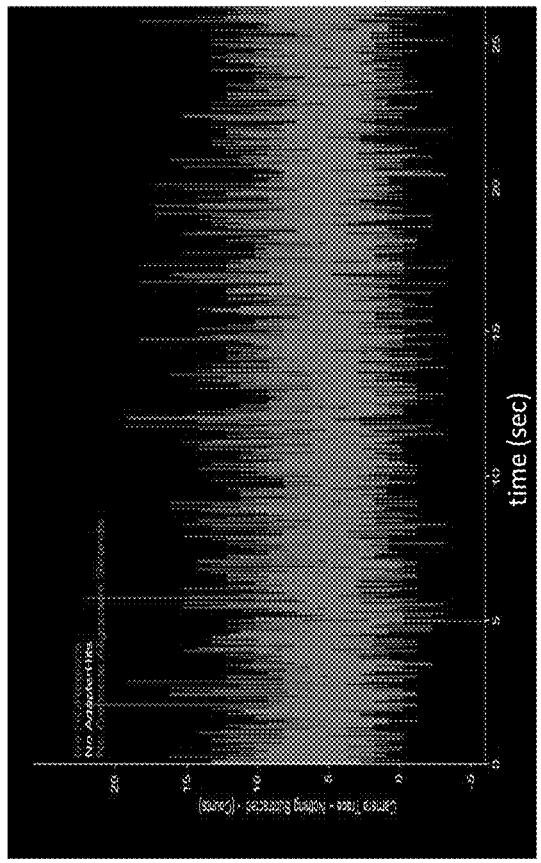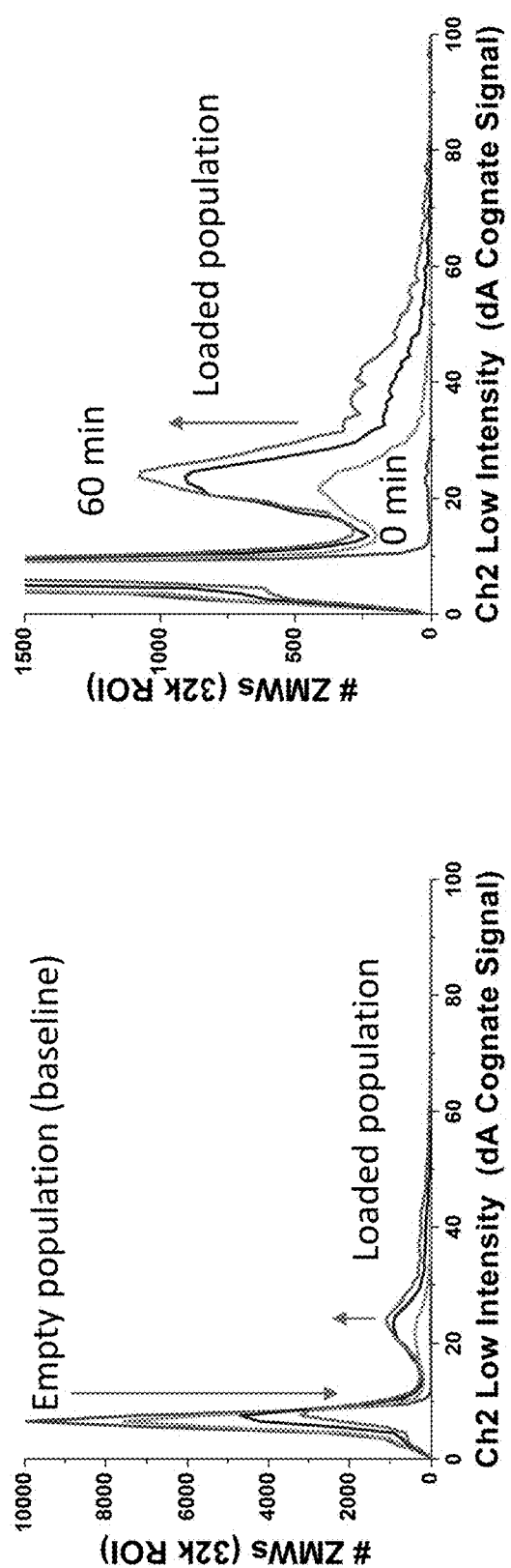
Fig. 12

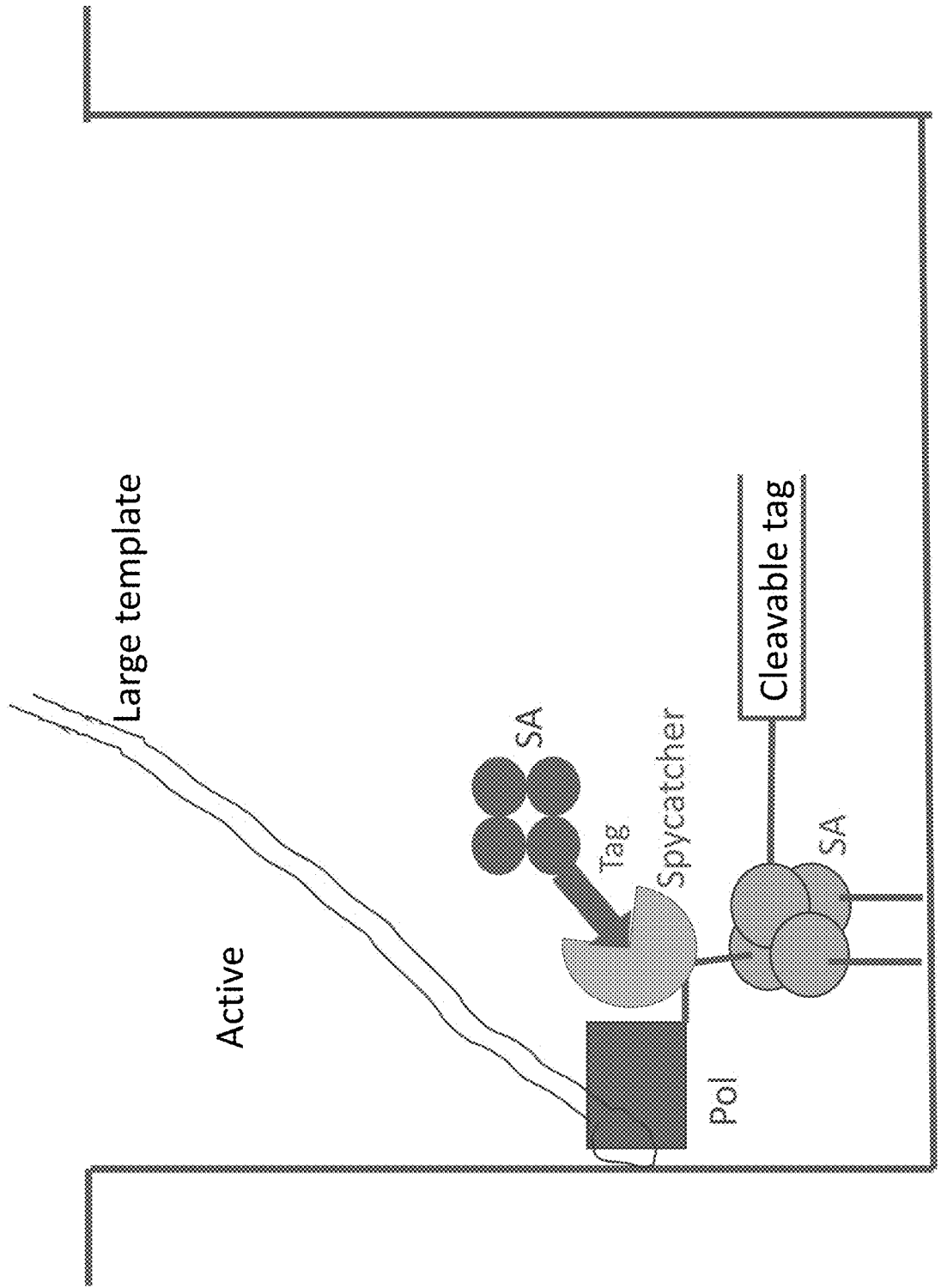

Sequencing yield from Sequel Dashboard:

Total loading: P1 + P2 = 98%

SEQUENCE LISTING

<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: synthetic oligopeptide linker

<400> SEQUENCE: 1

Gly Gly Gly Ser
1

<210> SEQ ID NO 2
<211> LENGTH: 8
<212> TYPE: PRT
<213> ORGANISM: Artificial Sequence
<220> FEATURE:
<223> OTHER INFORMATION: synthetic oligopeptide linker

<400> SEQUENCE: 2

Gly Gly Gly Ser Gly Gly Gly Ser
1               5

<210> SEQ ID NO 3
<211> LENGTH: 6
<212> TYPE: PRT
<213> ORGANISM: Artificial Sequence
<220> FEATURE:
<223> OTHER INFORMATION: oligopeptide thrombin site

<400> SEQUENCE: 3

Leu Val Pro Arg Gly Ser
1               5

<210> SEQ ID NO 4
<211> LENGTH: 6
<212> TYPE: PRT
<213> ORGANISM: Artificial Sequence
<220> FEATURE:
<223> OTHER INFORMATION: oligopeptide TEV site

<400> SEQUENCE: 4

Glu Asn Leu Tyr Phe Gln
1               5

METHODS AND COMPOSITIONS FOR DELIVERY OF MOLECULES AND COMPLEXES TO REACTION SITES

CROSS-REFERENCE TO RELATED APPLICATIONS

This application is a non-provisional utility patent application claiming priority to and benefit of the following prior provisional patent applications: U.S. Ser. No. 62/692,234, filed Jun. 29, 2018, entitled "Methods and compositions for delivery of molecules and complexes to reaction sites" by Jaime Juan Benitez-Marzan et al., and U.S. Ser. No. 62/837,159, filed Apr. 22, 2019, entitled "Methods and compositions for delivery of molecules and complexes to reaction sites" by Jaime Juan Benitez-Marzan et al., each of which is incorporated herein by reference in its entirety for all purposes.

INCORPORATION-BY-REFERENCE OF MATERIAL SUBMITTED BY U.S.P.T.O. eFS-WEB

The instant application contains a Sequence Listing which is being submitted in computer readable form via the United States Patent and Trademark Office eFS-WEB system and which is hereby incorporated by reference in its entirety for all purposes. The txt file submitted herewith contains a 2 KB file (Ser. No. 01/021,502_2019-09-12_SequenceListing.txt).

STATEMENT AS TO RIGHTS TO INVENTIONS MADE UNDER FEDERALLY SPONSORED RESEARCH AND DEVELOPMENT

Not applicable.

BACKGROUND OF THE INVENTION

Techniques in molecular biology and molecular medicine often rely on analysis of single biological molecules. Such techniques include DNA and RNA sequencing, polymorphism detection, the detection of proteins of interest, the detection of protein-nucleic acid complexes, and many others. The high sensitivity, high throughput and low reagent costs involved in single molecule analysis make this type of analysis an increasingly attractive approach for a variety of detection and analysis problems in molecular medicine, from low cost genomics to high sensitivity marker analysis.

The small observation volumes often used for single molecule analysis methods are typically provided by immobilizing or otherwise localizing molecules of interest within an optical confinement reaction/observation region, such as in an array of extremely small wells as in an array of Zero Mode Waveguides (ZMWs), and delivering molecules of interest (including, for example, a template, primers, enzymes etc.) to the reaction region. One difficulty in performing single molecule analyses occurs in loading a sufficient number of the reaction/observation regions of single molecule analysis devices with the molecules of interest (e.g., template or other analyte and/or enzyme). Entropic barriers to loading can be significant when attempting to load large reactant molecules into these nanoscale reaction sites.

It would be desirable to develop methods and compositions for allowing a predetermined number of reaction sites to be occupied by a molecule of interest. The present invention provides these and other features that will be apparent upon complete review of the following.

SUMMARY OF THE INVENTION

Accordingly, the present disclosure provides methods, compositions, and systems for monitoring and assessing the distribution of molecules of interest into a predetermined number of reaction sites.

One general class of embodiments provides methods for loading polymerase enzyme complexes into a predetermined number of nanoscale wells. In the methods, a surface comprising an array of nanoscale wells is provided. A loading solution that includes (i) one or more nucleotides and/or nucleotide analogs and (ii) polymerase enzyme complexes comprising a template nucleic acid and a polymerase enzyme is contacted to the surface. Interactions between the nucleotides and/or nucleotide analogs and the polymerase enzyme complexes result in generation of signal pulses. The array of nanoscale wells is monitored while the loading solution is in contact with the surface, to detect signal pulses from within the wells and thereby identify nanoscale wells that have been loaded with a polymerase enzyme complex. The loading solution is maintained in contact with the surface until the predetermined number of nanoscale wells have been loaded with a polymerase enzyme complex.

In one class of embodiments, the loading solution comprises one or more labeled nucleotide analogs, and the signal pulses are a result of non-incorporation events involving the labeled nucleotide analogs. For example, the loading solution can comprise one or more additives that maintain the polymerase enzymes in an inactive state, e.g., a divalent cation, e.g., strontium, cobalt, tin, calcium, nickel, europium, barium, iron, or zinc. In another example, the labeled nucleotide analog is a nonhydrolyzable labeled nucleotide analog.

In one class of embodiments, the array of nanoscale wells is part of a substrate that allows signal pulses to be detected only when a polymerase enzyme complex is within a nanoscale well, for example, within an observation volume at the base of the nanoscale well.

The template nucleic acids in the polymerase enzyme complexes are optionally hybridized to a primer. The template nucleic acids can have essentially any desired configuration. In one exemplary class of embodiments, the template nucleic acids comprise a hairpin loop at one or both ends, e.g., of a double-stranded central region.

The predetermined number of nanoscale wells occupied by a polymerase enzyme complex can be essentially any desired number. For example, in one class of embodiments, the predetermined number of nanoscale wells occupied by a polymerase enzyme complex is about 60-80% of the nanoscale wells in the array. In some embodiments, about 10-40% of the nanoscale wells in the array, e.g., about 20-35% of the nanoscale wells in the array, are occupied by a single polymerase enzyme complex.

After the predetermined number of nanoscale wells in the array are occupied by a polymerase enzyme complex, the surface can be washed to remove the loading solution. Optionally, the array is prepared for analyzing the polymerase enzyme complexes within the nanoscale wells. In one class of embodiments, a nucleotide sequence of the template nucleic acid is determined, for example, by providing one or more nucleotides or nucleotide analogs; performing a polymerization reaction in which the polymerase enzyme replicates at least a portion of the template nucleic acid in a template-dependent manner, whereby one or more of the nucleotides or nucleotide analogs are incorporated into the resulting nucleic acid; and identifying a time sequence of incorporation of the one or more nucleotide or nucleotide analogs into the resulting nucleic acid.

In some embodiments, the polymerase enzyme complexes are immobilized within the nanoscale wells, e.g., in an observation volume at the base of the nanoscale well. For example, in one class of embodiments, the polymerase enzyme complexes comprise a reactive element, and the immobilizing occurs through an interaction of the reactive element (e.g., streptavidin) and a binding site in the nanoscale well (e.g., biotin).

The loading solution can include at least one agent to mitigate photodamage. Suitable agents are known in the art and include, but are not limited to, triplet-state quenchers, reducing agents, singlet oxygen quenchers, and oxygen depleting enzymes, e.g., ascorbic acid, dithiothreitol, mercaptoethylamine, beta-mercaptoethanol, n-propyl gallate, p-phenylenediamine, hydroquinone, sodium azide, diazobicyclooctane, Trolox, butylated hydroxytoluene, cyclooctatetraene, super oxide dismutase, glucose oxidase, cholesterol oxidase, lactate oxidase, pyruvate oxidase, xanthine oxidase, and protocatechuate 3,4 dioxygenase.

In one class of embodiments, the array of nanoscale wells is monitored to detect signal pulses from within the wells (and thereby identify nanoscale wells that have been loaded with a polymerase enzyme complex) at one or more time points after contacting the loading solution to the surface, to obtain initial loading data, e.g., at 1-10, 2-10, or 2-5 time points, e.g., within 5-60 minutes or 10-30 minutes after loading is initiated. From this initial loading data, a predicted end time point at which the predetermined number of nanoscale wells will have been loaded with a polymerase enzyme complex is calculated. The loading solution is then maintained in contact with the surface until the predicted end time point is reached. At the predicted end time point (or as quickly thereafter as practical), the loading solution is removed from the surface, e.g., by washing.

Another general class of embodiments provides methods for loading polymerase enzyme complexes into a predetermined number of nanoscale wells, in which a surface comprising an array of nanoscale wells whose base comprises a capture moiety is provided. A loading solution that includes (i) one or more nucleotides and/or nucleotide analogs and (ii) polymerase enzyme complexes comprising a template nucleic acid and a polymerase enzyme is contacted to the surface. The polymerase enzyme complexes reversibly bind to the capture moiety in the nanoscale wells. Interactions between the nucleotides and/or nucleotide analogs and the polymerase enzyme complexes result in generation of signal pulses, and, while the loading solution is in contact with the surface, the array of nanoscale wells is monitored to detect signal pulses from within the wells and thereby identify nanoscale wells that have been loaded with a polymerase enzyme complex. The number or concentration of polymerase enzyme complexes in the loading solution is increased (e.g., by addition of more complexes) or reduced (e.g., by dilution or removal) as needed until the predetermined number of nanoscale wells have been loaded with a polymerase enzyme complex. Once the predetermined number of nanoscale wells have been loaded with a polymerase enzyme complex, the polymerase enzyme complexes are covalently attached to the capture moiety.

In one class of embodiments, the one or more nucleotides and/or nucleotide analogs are labeled and the signal pulses are generated by interactions between the polymerase enzyme complexes and the labeled nucleotides and/or nucleotide analogs. In one class of embodiments, the array of nanoscale wells is part of a substrate that allows signal pulses to be detected only when a polymerase enzyme complex is within a nanoscale well, for example, within an observation volume at the base of the nanoscale well.

In some embodiments, the polymerase enzyme is desthiobiotinylated. In such embodiments, the capture moiety can comprise streptavidin, and the polymerase enzyme complexes can be reversibly immobilized to the nanoscale wells through interactions between the desthiobiotin on the polymerase enzymes and the streptavidin in the nanoscale wells.

The polymerase enzyme complexes can be covalently attached to the capture moiety by adding a crosslinker to the loading solution to covalently crosslink the polymerase enzyme to the streptavidin. In one exemplary class of embodiments, the polymerase enzyme comprises a reactive cysteine in proximity to the desthiobiotin, the streptavidin comprises a reactive cysteine, and covalently attaching the polymerase enzyme complexes to the capture moiety comprises applying a bismaleimide reagent to crosslink the reactive cysteines on the polymerase enzymes to the streptavidin in the nanoscale wells.

Another general class of embodiments provides methods for establishing single active polymerase enzyme complexes within a predetermined number of nanoscale wells. In the methods, an array of nanoscale wells is provided. Two or more polymerase enzyme complexes (comprising a polymerase enzyme complexed to a template nucleic acid) are delivered to a majority of the nanoscale wells. A portion of the polymerase enzyme complexes are inactivated. Signals from the polymerase enzyme complexes are monitored, and the inactivating step is continued until a level of signals is reached that indicates that a predetermined number of the nanoscale wells contain only a single active polymerase enzyme complex, thereby establishing single active polymerase enzyme complexes within a predetermined number of nanoscale wells. Optionally, the array of nanoscale wells is part of a substrate that allows signals to be detected only when the polymerase enzyme complexes are within an observation volume within a nanoscale well.

In one aspect, complexes are inactivated by exposing polymerase enzyme complexes within the nanoscale wells to light to induce photodamage in a portion of the polymerase enzyme complexes; active polymerase enzyme complexes are able to generate signals and photodamaged polymerase enzyme complexes are unable to generate signals. The array can be exposed to oxygen to accelerate photodamage to the polymerase enzyme complexes. In some embodiments, the nanoscale wells comprise one or more labeled nucleotide analogs. Typically, the signals are generated by interactions between the polymerase enzyme complexes and the labeled nucleotide analogs. In some embodiments, the polymerase enzyme replicates at least a portion of the template nucleic acid in a template-dependent manner, whereby one or more of the nucleotide analogs are incorporated into the resulting nucleic acid, thereby generating the signals. The nanoscale wells optionally also include one or more agents that decrease processivity of the polymerase enzyme as compared to processivity of the polymerase enzyme in the absence of the agents.

In another aspect, the signals generated by the polymerase enzyme complexes are from extension of the template nucleic acids by the polymerase enzymes, and complexes are inactivated by addition of an extension-terminating reagent to the nanoscale wells. Suitable extension terminating reagents are known in the art and include, but are not limited to, one or more dideoxynucleotide triphosphates (ddNTPs). In some embodiments, inactivation occurs over a period of time from about 10 to about 30 minutes. Once a predetermined number of nanoscale wells contains a single active polymerase enzyme complex, the extension terminating reagent can be removed by washing the array of nanoscale wells. In some embodiments, the nanoscale wells comprise one or more labeled nucleotide analogs, and the polymerase enzyme replicates at least a portion of the template nucleic acid in a template-dependent manner, whereby one or more of the nucleotide analogs are incorporated into the resulting nucleic acid, thereby generating the signals.

Regardless of how inactivation is achieved, after the predetermined number of nanoscale wells contain a single active polymerase enzyme complex, the array is optionally prepared for conducting reactions for analyzing the polymerase enzyme complexes. For example, a nucleotide sequence of the template nucleic acid can be determined, e.g., by providing one or more nucleotides or nucleotide analogs; performing a polymerization reaction in which the polymerase enzyme replicates at least a portion of the template nucleic acid in a template-dependent manner, whereby one or more of the nucleotides or nucleotide analogs are incorporated into the resulting nucleic acid; and identifying a time sequence of incorporation of the one or more nucleotide or nucleotide analogs into the resulting nucleic acid.

In some embodiments, monitoring signals from the polymerase enzyme complexes includes calculating the average number of active complexes per well based on an average level of signals detected from at least a plurality of the nanoscale wells.

In some embodiments, the polymerase enzyme complexes are immobilized within the nanoscale wells, e.g., in an observation volume at the base of the nanoscale well. For example, in one class of embodiments, the polymerase enzyme complexes comprise a reactive element, and the immobilizing occurs through an interaction of the reactive element (e.g., streptavidin) and a binding site in the nanoscale well (e.g., biotin).

The predetermined number of nanoscale wells occupied by a single active polymerase enzyme complex can be essentially any desired number. For example, in one class of embodiments, the predetermined number of nanoscale wells occupied by a single active polymerase enzyme complex is at least about 30% of the nanoscale wells in the array.

One general class of embodiments provides methods for establishing single active polymerase enzyme complexes within a predetermined number of nanoscale wells. In the methods, an array of nanoscale wells is provided, and polymerase enzyme complexes are delivered to a majority of the nanoscale wells. The polymerase enzyme complexes comprise a polymerase enzyme complexed to a template nucleic acid, and the polymerase enzyme is inhibited during the delivering step. The polymerase enzyme complexes are immobilized within the nanoscale wells. Inhibition of at least a plurality of polymerase enzymes that are within the nanoscale wells is released, thereby allowing the disinhibited polymerase enzyme complexes to generate signals. Signals from disinhibited polymerase enzyme complexes are monitored, and the releasing step is continued until a level of signals is reached that indicates that a predetermined number of the nanoscale wells contain a single active polymerase enzyme complex, thereby establishing single active polymerase enzyme complexes within a predetermined number of nanoscale wells.

In some embodiments, the releasing step is concomitant with the immobilizing step. In some embodiments, the releasing step follows the immobilizing step.

In one class of embodiments, the polymerase enzyme complexes comprise a primer hybridized to the template nucleic acid, and the primer is linked to a nonhydrolyzable nucleotide analog by a photocleavable tether. The nanoscale wells are illuminated, such that immobilization of the polymerase enzyme complex within the nanoscale well results in cleavage of the tether to release the nonhydrolyzable nucleotide analog and thereby release the inhibition of the polymerase enzyme.

In one class of embodiments, the polymerase enzyme complexes comprise a primer hybridized to the template nucleic acid and linked to a nonhydrolyzable nucleotide analog by a tether, and the releasing step comprises cleaving the tether to release the nonhydrolyzable nucleotide analog and thereby release the inhibition of the polymerase enzyme. In one class of embodiments, the tether is cleavable by a cleavage agent, and the releasing step includes exposing the immobilized polymerase enzyme complexes to the cleavage agent until the level of signals is reached that indicates that a predetermined number of the nanoscale wells contain a single active polymerase enzyme complex. In an exemplary class of embodiments, the tether comprises a protease site and the cleavage agent is a protease. Suitable proteases and their corresponding cleavage sites are known in the art and include, but are not limited to, thrombin, Tobacco Etch Virus (TEV) protease, enterokinase, 3C rhinovirus protease, and trypsin. In another exemplary class of embodiments, the tether comprises DNA and the cleavage agent is an endonuclease. For example, the tether can comprise a restriction site and the cleavage agent can be a restriction enzyme. In another exemplary class of embodiments, the tether comprises RNA and the cleavage agent is an RNAse.

In one class of embodiments, the polymerase enzyme is inhibited by binding of a polyphosphate moiety to the polymerase enzyme. In some embodiments, the releasing step comprises exposing the polymerase enzyme complexes to a phosphatase. In other embodiments, the polyphosphate moiety is linked to the polymerase enzyme by a tether, and the releasing step comprises cleaving the tether to release the polyphosphate group and thereby release the inhibition of the polymerase enzyme. In one class of embodiments, the tether is cleavable by a cleavage agent, and the releasing step includes exposing the polymerase enzyme complexes to the cleavage agent until the level of signals is reached that indicates that a predetermined number of the nanoscale wells contain a single active polymerase enzyme complex. In an exemplary class of embodiments, the tether comprises a protease site and the cleavage agent is a protease, e.g., thrombin, Tobacco Etch Virus (TEV) protease, enterokinase, 3C rhinovirus protease, or trypsin. In another exemplary class of embodiments, the tether comprises DNA (e.g., a restriction site) and the cleavage agent is an endonuclease (e.g., a restriction enzyme). In another exemplary class of embodiments, the tether comprises RNA and the cleavage agent is an RNAse.

In one class of embodiments, the polymerase enzyme complexes comprise a primer hybridized to the template nucleic acid. The primer comprises a reversible terminating group at its 3' end, and the releasing step comprises removing the terminating group from the primer.

The predetermined number of nanoscale wells occupied by a single active polymerase enzyme complex can be essentially any desired number. For example, in one class of embodiments, the predetermined number of nanoscale wells occupied by a single active polymerase enzyme complex is at least about 30% of the nanoscale wells in the array.

In some embodiments, the nanoscale wells contain labeled nucleotide analogs, and the signals generated by the disinhibited polymerase enzyme complexes represent interactions between the polymerase enzyme complexes and the labeled nucleotide analogs.

Once the predetermined number of nanoscale wells is reached, the array can be prepared for conducting reactions for analyzing the polymerase enzyme complexes. In one class of embodiments, a nucleotide sequence of the template nucleic acid is determined, for example, by providing one or more nucleotides or nucleotide analogs; performing a polymerization reaction in which the polymerase enzyme replicates at least a portion of the template nucleic acid in a template-dependent manner, whereby one or more of the nucleotides or nucleotide analogs are incorporated into the resulting nucleic acid; and identifying a time sequence of incorporation of the one or more nucleotide or nucleotide analogs into the resulting nucleic acid.

A related general class of embodiments provides methods for providing active polymerase enzyme complexes in nanoscale wells. In the methods, an array of nanoscale wells is provided, and polymerase enzyme complexes are delivered to a plurality of the nanoscale wells. The polymerase enzyme complexes comprise a polymerase enzyme complexed to a template nucleic acid, and the polymerase enzyme is inhibited during delivery. The polymerase enzyme complexes are immobilized within the nanoscale wells. Inhibition of at least a plurality of polymerase enzymes that are immobilized within the nanoscale wells is released, thereby establishing active polymerase enzyme complexes within the nanoscale wells.

In some embodiments, a portion of the polymerase enzymes remain inhibited during the releasing and analyzing steps, and the releasing step is repeated after the analyzing step. The analyzing step can then also be repeated.

In some embodiments, uninhibited polymerase enzyme complexes are delivered to the nanoscale wells and immobilized along with the inhibited complexes. The uninhibited polymerase enzyme complexes are analyzed, then inhibition of the dormant inhibited complexes is relieved and the newly active polymerase enzyme complexes are analyzed.

In some embodiments, the polymerase enzyme complexes include an uninhibited polymerase enzyme that is complexed to a barcode nucleic acid and that is connected (covalently or noncovalently) to the inhibited polymerase enzyme through a cleavable linker. In such embodiments, the uninhibited polymerase enzyme/barcode nucleic acid complexes are analyzed, and then the uninhibited polymerase enzyme complexes are exposed to a cleavage agent. The uninhibited polymerase complexes can be removed from the wells, e.g., by washing or diffusion. Inhibition of the inhibited polymerase enzymes is released, and the resulting active polymerase enzyme complexes are then analyzed.

Essentially all of the features noted above apply to these embodiments as well, as relevant, e.g., with respect to inhibition of the polymerase and relief of inhibition, number of wells, subsequent analysis, and/or the like. For example, the polymerase enzyme complexes can comprise a primer hybridized to the template nucleic acid and linked to a nonhydrolyzable nucleotide analog by a cleavable tether, and the releasing step can include cleaving the tether to release the nonhydrolyzable nucleotide analog and thereby release the inhibition of the polymerase enzyme, e.g., by exposing the immobilized polymerase enzyme complexes to a cleavage agent (e.g., a protease, an endonuclease, an RNase, or the like). The polymerase enzyme can be inhibited by binding of a polyphosphate moiety to the polymerase enzyme, and the polyphosphate can be removed by exposing the polymerase enzyme complexes to a phosphatase or by cleaving a tether linking it to the enzyme. The polymerase enzyme complexes can comprise a primer hybridized to the template nucleic acid and comprising a reversible terminating group at its 3' end, and the releasing step can include removing the terminating group from the primer.

Another related general class of embodiments provides methods for providing active polymerase enzyme complexes in nanoscale wells. In the methods, an array of nanoscale wells is provided. A portion (e.g., a majority) of the wells in the array have immobilized therein at least one inhibited polymerase enzyme complex comprising an inhibited polymerase enzyme complexed to a template nucleic acid. Inhibition of at least a portion of the polymerase enzymes is released, thereby establishing active polymerase enzyme complexes within the nanoscale wells.

The polymerases can be inhibited during their delivery to the wells, or inhibition can be applied after the complexes have been delivered to (and optionally immobilized in) the wells. In some embodiments, a mixture of active and inhibited polymerase enzyme complexes are immobilized in the wells. An active and an inhibited polymerase enzyme can be bound to the same template nucleic acid molecule or to different nucleic acid molecules, depending on the desired application of the methods.

Essentially all of the features noted above apply to these embodiments as well, as relevant, e.g., with respect to type of inhibitor and relief of inhibition, number of wells, subsequent analysis, and/or the like. For example, the polymerase enzyme complexes can comprise a primer hybridized to the template nucleic acid and linked to a nonhydrolyzable nucleotide analog by a cleavable tether, and the releasing step can include cleaving the tether to release the nonhydrolyzable nucleotide analog and thereby release the inhibition of the polymerase enzyme, e.g., by exposing the immobilized polymerase enzyme complexes to a cleavage agent (e.g., a protease, an endonuclease, an RNase, or the like). The polymerase enzyme can be inhibited by binding of a polyphosphate moiety to the polymerase enzyme, and the polyphosphate can be removed by exposing the polymerase enzyme complexes to a phosphatase or by cleaving a tether linking it to the enzyme. The polymerase enzyme complexes can comprise a primer hybridized to the template nucleic acid and comprising a reversible terminating group at its 3' end, and the releasing step can include removing the terminating group from the primer.

Another general class of embodiments provides an array of nanoscale wells, in which a plurality of the wells have immobilized therein at least one inhibited polymerase enzyme complex comprising an inhibited polymerase enzyme complexed to a template nucleic acid. The array is optionally present in a nucleic acid sequencing system.

Essentially all of the features noted for the methods above apply to these embodiments as well, as relevant, e.g., with respect to type of inhibitor, number of occupied wells, inclusion of active polymerase complexes, and/or the like. For example, in one class of embodiments, the inhibited polymerase enzyme complexes comprise a primer that is hybridized to the template nucleic acid and that is linked to a nonhydrolyzable nucleotide analog by a cleavable tether. In one class of embodiments, the polymerase enzyme is inhibited by binding of a polyphosphate moiety to the polymerase enzyme. In one class of embodiments, the inhibited polymerase enzyme complexes comprise a primer that is hybridized to the template nucleic acid and that comprises a reversible terminating group at its 3' end. In some embodiments, a plurality of the wells further comprise immobilized therein at least one active polymerase enzyme complex comprising an active polymerase enzyme. The active polymerase enzyme can be bound to the same template nucleic acid molecule as the inhibited polymerase enzyme or to a different nucleic acid molecule. In some embodiments, the inhibited polymerase enzyme is connected through a cleavable linker to an active polymerase enzyme, which active polymerase enzyme is complexed to a different template nucleic acid.

Another general class of embodiments provides a complex comprising a template nucleic acid to which are bound a first polymerase enzyme and a second polymerase enzyme. The first polymerase enzyme is active and the second polymerase enzyme is inhibited.

In one class of embodiments, a first primer is hybridized to the template nucleic acid and bound to the first polymerase enzyme, and a second primer is hybridized to the template nucleic acid and bound to the second polymerase enzyme. The second primer comprises a reversible terminating group at its 3' end.

In one class of embodiments, the template nucleic acid comprises a double-stranded central region and two single-stranded hairpin end regions. The first polymerase enzyme can be bound to one end region and the second polymerase enzyme can be bound to the other end region.

In one class of embodiments, the second polymerase enzyme is bound to the template nucleic acid 5' of and proximal to the first polymerase enzyme, wherein directionality is relative to a nascent strand produced by the first polymerase enzyme.

The complex is optionally present in a nucleic acid sequencing system. In one class of embodiments, the template nucleic acid is immobilized in a nanoscale well. In some embodiments, the first and second polymerases each comprise at least one biotin moiety through which the polymerase enzymes are immobilized in the observation region of the nanoscale well, whereby the template nucleic acid is immobilized in the nanoscale well.

Essentially all of the features noted for the methods above apply to these embodiments as well, as relevant, e.g., with respect to type of inhibitor, number of occupied wells in an array, and/or the like.

One general class of embodiments provides methods of sequence determination. In the methods, a complex is provided that comprises a template nucleic acid to which are bound a first polymerase enzyme and a second polymerase enzyme. The first polymerase enzyme is active and the second polymerase enzyme is inhibited. The template nucleic acid is subjected to a polymerization reaction in which the first polymerase enzyme replicates at least a portion of the template in a template-dependent manner, whereby one or more nucleotides and/or nucleotide analogs are incorporated into the resulting first nucleic acid product. A time sequence of incorporation of the one or more nucleotides and/or nucleotide analogs into the resulting first nucleic acid product is identified. The first polymerase enzyme is optionally inhibited, inactivated, or removed. Inhibition of the second polymerase enzyme is then released, and the template nucleic acid is subjected to a polymerization reaction in which the second polymerase enzyme replicates at least a portion of the template in a template-dependent manner, whereby one or more nucleotides and/or nucleotide analogs are incorporated into the resulting second nucleic acid product. A time sequence of incorporation of the one or more nucleotides and/or nucleotide analogs into the resulting second nucleic acid product is identified.

In some embodiments, the subjecting steps are performed in a nanoscale well, e.g., in the observation volume of a nanoscale well. Essentially all of the features noted for the methods above apply to these embodiments as well, as relevant, e.g., with respect to type of inhibitor and relief of inhibition, number of occupied wells in an array, and/or the like.

Another general class of embodiments provides methods of sequence determination. In the methods, a barcoded complex is provided that comprises a first polymerase enzyme complexed to a barcode nucleic acid and a second polymerase enzyme complexed to a template nucleic acid. The first polymerase enzyme is active and the second polymerase enzyme is inhibited. The barcode nucleic acid is subjected to a polymerization reaction in which the first polymerase enzyme replicates at least a portion of the barcode nucleic acid in a template-dependent manner, whereby one or more nucleotides and/or nucleotide analogs are incorporated into the resulting first nucleic acid product. A time sequence of incorporation of the one or more nucleotides and/or nucleotide analogs into the resulting first nucleic acid product is identified. The first polymerase enzyme is optionally inhibited, inactivated, or removed. Inhibition of the second polymerase enzyme is released, and the template nucleic acid is subjected to a polymerization reaction in which the second polymerase enzyme replicates at least a portion of the template in a template-dependent manner, whereby one or more nucleotides and/or nucleotide analogs are incorporated into the resulting second nucleic acid product. A time sequence of incorporation of the one or more nucleotides and/or nucleotide analogs into the resulting second nucleic acid product is identified.

In some embodiments, the first polymerase enzyme and the second polymerase enzyme are connected by a cleavable linker. After the first polymerization reaction and identification of the time sequence of incorporation of the one or more nucleotides and/or nucleotide analogs into the first nucleic acid product, the barcode complex is exposed to a cleavage agent to remove the first polymerase enzyme from the complex. The first polymerase enzyme can be removed from the wells, e.g., by washing or diffusion.

In some embodiments, the subjecting steps are performed in a nanoscale well, e.g., in the observation volume of a nanoscale well. Essentially all of the features noted for the methods above apply to these embodiments as well, as relevant, e.g., with respect to type of inhibitor and relief of inhibition, number of occupied wells in an array, and/or the like.

One general class of embodiments provides a complex comprising a first polymerase enzyme complexed to a first nucleic acid and a second polymerase enzyme complexed to a second nucleic acid, wherein the first and second polymerase enzymes are connected by a cleavable linker.

In some embodiments, the first polymerase enzyme is inhibited and the second polymerase enzyme is active. In some embodiments, the first nucleic acid is a target nucleic acid whose sequence is to be determined. One of the nucleic acids can be a barcode nucleic acid. For example, in some embodiments, the sequence of the second nucleic acid identifies the origin of the first nucleic acid.

The complex is optionally present in a nucleic acid sequencing system. In one class of embodiments, the template nucleic acid is immobilized in a nanoscale well.

One general class of embodiments provides methods for immobilizing polymerase enzyme complexes within a predetermined number of nanoscale wells. In the methods, an array of nanoscale wells is provided. Polymerase enzyme complexes comprising a template nucleic acid and a polymerase enzyme are immobilized in the nanoscale wells through a cleavable linker. Optionally, two or more polymerase enzyme complexes are immobilized in a majority of the nanoscale wells in the array. The immobilized polymerase enzyme complexes are exposed to a cleavage agent, and this exposing step is continued until the predetermined number of nanoscale wells contain a polymerase enzyme complex. Once the predetermined number of nanoscale wells contain a polymerase enzyme complex, the cleavage agent can be inactivated or removed.

In some embodiments, the nanoscale wells comprise one or more labeled nucleotide analogs, and interactions between the nucleotide analogs and the polymerase enzyme complexes result in generation of signal pulses. The array of nanoscale wells can be monitored to detect signal pulses from within the wells and thereby identify nanoscale wells containing a polymerase enzyme complex.

In one class of embodiments, the cleavable linker comprises a peptide and the cleavage agent comprises a protease, e.g., thrombin, Tobacco Etch Virus (TEV) protease, enterokinase, 3C rhinovirus protease, or trypsin. In one class of embodiments, the cleavable linker comprises DNA and the cleavage agent comprises an endonuclease (e.g., a restriction enzyme). In one class of embodiments, the cleavable linker comprises RNA and the cleavage agent comprises an RNase.

In one class of embodiments, before exposure to the cleavage agent, the template nucleic acid is subjected to a polymerization reaction in which the polymerase enzyme replicates at least a portion of the template in a template-dependent manner, whereby one or more nucleotides and/or nucleotide analogs are incorporated into resulting nucleic acid product. The polymerization reaction is then halted. The cleavage agent is tethered to a nucleobase, and thus can achieve a high effective local concentration near the polymerase complex.

In some embodiments, additional polymerase enzyme complexes are immobilized in the nanoscale wells through a linker that is not subject to cleavage by the cleavage agent. In some embodiments, different complexes are immobilized through linkers that are subject to cleavage by different cleavage agents.

The predetermined number of nanoscale wells occupied by a polymerase enzyme complex can be essentially any desired number. For example, in one class of embodiments, the predetermined number of nanoscale wells occupied by a polymerase enzyme complex is about 60-80% of the nanoscale wells in the array. In some embodiments, about 10-40% of the nanoscale wells in the array, e.g., about 20-35% of the nanoscale wells in the array, are occupied by a single polymerase enzyme complex.

After the predetermined number of nanoscale wells in the array are occupied by a polymerase enzyme complex, the array can be prepared for analyzing the polymerase enzyme complexes within the nanoscale wells. In one class of embodiments, a nucleotide sequence of the template nucleic acid is determined, for example, by providing one or more nucleotides or nucleotide analogs; performing a polymerization reaction in which the polymerase enzyme replicates at least a portion of the template nucleic acid in a template-dependent manner, whereby one or more of the nucleotides or nucleotide analogs are incorporated into the resulting nucleic acid; and identifying a time sequence of incorporation of the one or more nucleotide or nucleotide analogs into the resulting nucleic acid.

The methods described herein are applicable to essentially any type of molecule (including complexes that comprise the molecule) and any type of reaction site. Thus, one general class of embodiments provides methods for loading molecules of interest into a predetermined number of reaction sites. In the methods, a surface comprising an array of reaction sites is provided. A loading solution comprising the molecules of interest is contacted to the surface. While the loading solution is in contact with the surface, the array of reaction sites is monitored to identify reaction sites that have been loaded with a molecule of interest (e.g., by monitoring signals from the molecules of interest, including signals produced by their interaction with or passage through a nanopore, signals produced by their interaction with or proximity to a nanoFET gate, signals produced by interaction with substrates, or the like, e.g., electrical signals, optical signals, etc.). The loading solution is maintained in contact with the surface until the predetermined number of reaction sites have been loaded with a molecule of interest.

In some embodiments, the reaction sites are nanoscale wells. In some embodiments, the reaction sites are nanoFET gate regions. In some embodiments, the reaction sites are nanoscale wells supporting a membrane, microscale wells supporting a membrane, nanoscale apertures supporting a membrane, or microscale apertures supporting a membrane. In such embodiments, the molecule of interest can be associated with a nanopore previously inserted in the membrane, or a nanopore with which the molecule of interest is associated (e.g., covalently or noncovalently, using techniques known in the art) can be inserted into the membrane. The molecule of interest can be, e.g., a nucleic acid, a protein, a motor protein, a polymerase, a helicase, or an exonuclease, and is optionally part of a complex (e.g., a protein/nucleic acid complex). Essentially all of the features noted for the methods above apply to these embodiments as well, as relevant, e.g., with respect to number of occupied sites in an array and/or the like.

One general class of embodiments provides methods for loading molecules of interest into a predetermined number of reaction sites. In the methods, a surface comprising an array of reaction sites that comprise a capture moiety is provided. A loading solution comprising the molecules of interest is contacted to the surface, whereby the molecules of interest reversibly bind to the capture moiety. While the loading solution is in contact with the surface, the array of reaction sites is monitored to identify reaction sites that have been loaded with a molecule of interest. The number or concentration of molecules of interest in the loading solution is increased or reduced as needed until the predetermined number of reaction sites have been loaded with a molecule of interest. Once the predetermined number of reaction sites have been loaded with a molecule of interest, the molecules of interest are covalently or otherwise effectively irreversibly attached to the capture moiety.

In some embodiments, the reaction sites are nanoscale wells. In some embodiments, the reaction sites are nanoFET gate regions. In some embodiments, the reaction sites are nanoscale wells supporting a membrane, microscale wells supporting a membrane, nanoscale apertures supporting a membrane, or microscale apertures supporting a membrane. In such embodiments, the molecule of interest can be associated with a nanopore previously inserted in the membrane, or a nanopore with which the molecule of interest is associated (e.g., covalently or noncovalently, using techniques known in the art) can be inserted into the membrane. The molecule of interest can be, e.g., a nucleic acid, a protein, a motor protein, a polymerase, a helicase, or an exonuclease, and is optionally part of a complex (e.g., a protein/nucleic acid complex). Essentially all of the features noted for the methods above apply to these embodiments as well, as relevant, e.g., with respect to number of occupied sites in an array, crosslinkers, and/or the like.

One general class of embodiments provides methods for establishing single active molecules of interest within a predetermined number of reaction sites. In the methods, an array of reaction sites is provided. Two or more molecules of interest are delivered to a majority of the reaction sites. A portion of the molecules of interest are inactivated. The inactivating step is continued until a predetermined number of the reaction sites contain only a single active molecule of interest.

In some embodiments, the reaction sites are nanoscale wells. In some embodiments, the reaction sites are nanoFET gate regions. In some embodiments, the reaction sites are nanoscale wells supporting a membrane, microscale wells supporting a membrane, nanoscale apertures supporting a membrane, or microscale apertures supporting a membrane. In such embodiments, the molecule of interest can be associated with a nanopore previously inserted in the membrane, or a nanopore with which the molecule of interest is associated (e.g., covalently or noncovalently, using techniques known in the art) can be inserted into the membrane. The molecule of interest can be, e.g., a nucleic acid, a protein, a motor protein, a polymerase, a helicase, or an exonuclease, and is optionally part of a complex (e.g., a protein/nucleic acid complex). Essentially all of the features noted for the methods above apply to these embodiments as well, as relevant, e.g., with respect to number of occupied sites in an array, techniques for inactivation, and/or the like.

One general class of embodiments provides methods for providing active molecules of interest in reaction sites. In the methods, an array of reaction sites in which a majority of the sites have immobilized therein at least one inhibited molecule of interest is provided. Inhibition of at least a portion of the molecules of interest is released, thereby establishing active molecules of interest within the reaction sites.

In some embodiments, the reaction sites are nanoscale wells. In some embodiments, the reaction sites are nanoFET gate regions. In some embodiments, the reaction sites are nanoscale wells supporting a membrane, microscale wells supporting a membrane, nanoscale apertures supporting a membrane, or microscale apertures supporting a membrane. In such embodiments, the molecule of interest can be associated with a nanopore previously inserted in the membrane, or a nanopore with which the molecule of interest is associated (e.g., covalently or noncovalently, using techniques known in the art) can be inserted into the membrane. The molecule of interest can be, e.g., a nucleic acid, a protein, a motor protein, a polymerase, a helicase, or an exonuclease, and is optionally part of a complex (e.g., a protein/nucleic acid complex).

Essentially all of the features noted for the methods above apply to these embodiments as well, as relevant, e.g., with respect to techniques for inhibiting the molecule of interest and relieving the inhibition, timing of inhibition with respect to delivery, use of cleavage agents, number of occupied sites in an array, and/or the like.

One general class of embodiments provides methods for immobilizing molecules of interest within a predetermined number of reaction sites. In the methods, an array of reaction sites is provided, and molecules of interest are immobilized in the reaction sites through a cleavable linker. The immobilized molecules of interest are exposed to a cleavage agent. The exposing step is continued until the predetermined number of reaction sites contain a molecule of interest.

In some embodiments, the reaction sites are nanoscale wells. In some embodiments, the reaction sites are nanoFET gate regions. In some embodiments, the reaction sites are nanoscale wells supporting a membrane, microscale wells supporting a membrane, nanoscale apertures supporting a membrane, or microscale apertures supporting a membrane. In such embodiments, the molecule of interest can be associated with a nanopore previously inserted in the membrane, or a nanopore with which the molecule of interest is associated (e.g., covalently or noncovalently, using techniques known in the art) can be inserted into the membrane. The molecule of interest can be, e.g., a nucleic acid, a protein, a motor protein, a polymerase, a helicase, or an exonuclease, and is optionally part of a complex (e.g., a protein/nucleic acid complex).

Essentially all of the features noted for the methods above apply to these embodiments as well, as relevant, e.g., with respect to number of occupied sites in an array, type of cleavage agent, and/or the like.

BRIEF DESCRIPTION OF THE DRAWINGS

FIG. 2A shows signal traces from a nanoscale well during loading. FIG. 2B shows signal traces from a nanoscale well during a sequencing reaction.

FIG. 12 shows loading of a ZMW with a 48 kb template.

FIG. 14D schematically illustrates removal of the polymerase/barcode complex and relief of polymerase inhibition to activate the inhibited polymerase.

Figure 1:
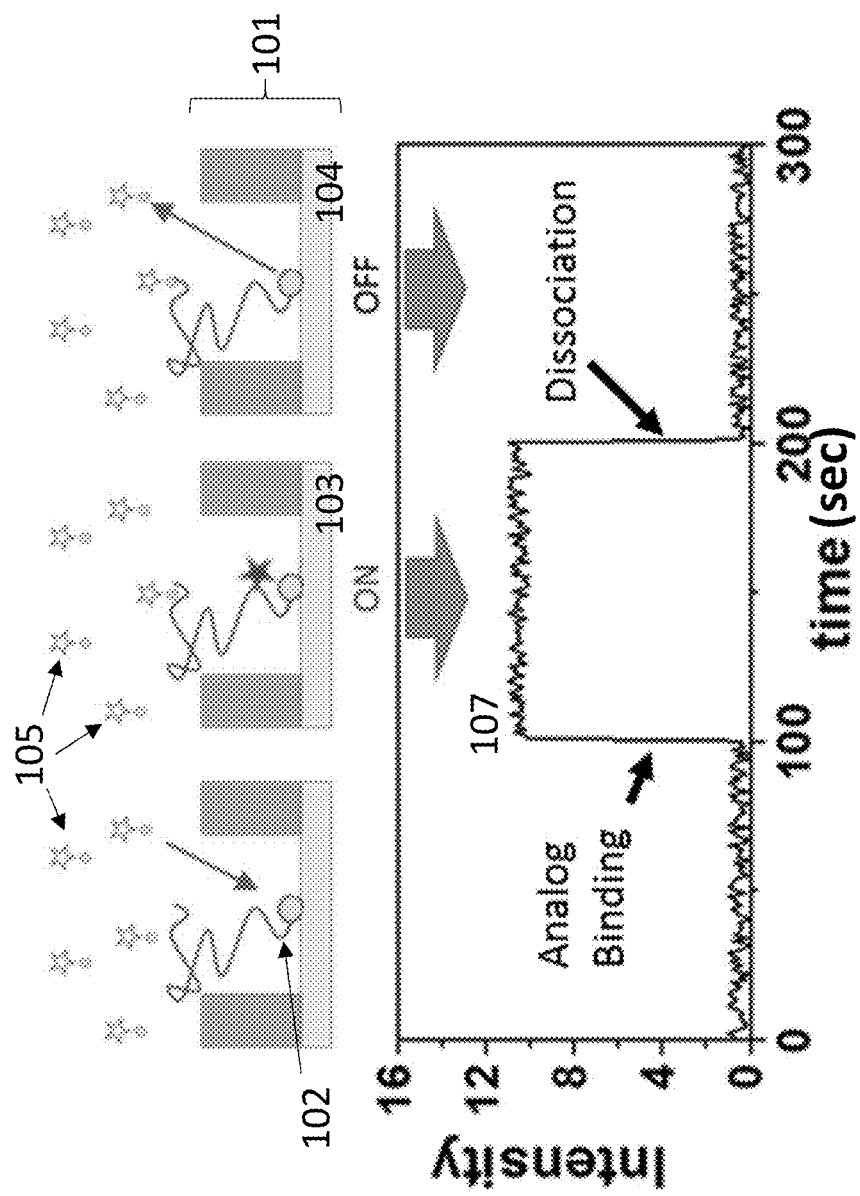
FIG. 1 is a schematic illustration of an exemplary loading method utilizing real-time monitoring of cognate sampling signals from a nanoscale well.

Schematic figures are not necessarily to scale.

DETAILED DESCRIPTION OF THE INVENTION

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include nucleic acid synthesis, isolation and/or manipulation, polymer array synthesis, hybridization, ligation, phage display, and detection using a label. Specific illustrations of suitable techniques can be had by reference to the examples herein below. However, other equivalent conventional procedures can, of course, also be used. Such conventional techniques and descriptions can be found in standard laboratory manuals such as Sambrook et al., Molecular Cloning—A Laboratory Manual (3rd Ed.), Vol. 1-3, Cold Spring Harbor Laboratory, Cold Spring Harbor, N.Y., 2000, Current Protocols in Molecular Biology, F. M. Ausubel et al., eds., Current Protocols, a joint venture between Greene Publishing Associates, Inc. and John Wiley & Sons, Inc., (supplemented through 2018), Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry 3rd Ed., W. H. Freeman Pub., New York, N.Y. and Berg et al. (2002) Biochemistry, 5th Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a molecule" includes a plurality of molecules, "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising), or alternatively including steps and compositions of no significance (consisting essentially of), or alternatively intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated, that all numerical designations are preceded by the term "about". The term "about" as used herein indicates the value of a given quantity varies by +/−10% of the value, or optionally +/−5% of the value, or in some embodiments, by +/−1% of the value so described. The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

"Nucleic acid," "polynucleotide," "oligonucleotide," or grammatical equivalents herein means at least two nucleotides covalently linked together. A nucleic acid of the present invention will generally contain phosphodiester bonds, although in some cases, nucleic acid analogs are included that may have alternate backbones, comprising, for example, phosphoramide, phosphorothioate, phosphorodithioate, and peptide nucleic acid backbones and linkages. Other analog nucleic acids include those with positive backbones, non-ionic backbones, and non-ribose backbones, including those described in U.S. Pat. Nos. 5,235,033 and 5,034,506. The nucleic acid may have other modifications, such as the inclusion of heteroatoms, the attachment of labels, such as dyes, or substitution with functional groups which will still allow for base pairing and for recognition by an enzyme. The length of a nucleic acid can be indicated in either nucleotides (measured on one strand of a single or double stranded nucleic acid) or base pairs (measured on both strands of a nucleic acid that is or that can be double stranded if hybridized to a complementary strand); units of nucleotides and base pairs thus can be used interchangeably to refer to an identical length, as will be clear to one skilled in the art.

As used herein, a "substantially identical" nucleic acid is one that has at least 80%, 85%, 90%, 95%, 96%, 97%, 98% or 99% sequence identity to a reference nucleic acid sequence. The length of comparison is preferably the full length of the nucleic acid, but is generally at least 20 nucleotides, 30 nucleotides, 40 nucleotides, 50 nucleotides, 75 nucleotides, 100 nucleotides, 125 nucleotides, or more.

I. Overview

Techniques for single molecule analysis typically require only very small amounts of sample. While this is overall a benefit of the techniques, accurately quantitating the limited amount of nucleic acids, proteins, or other molecules of interest in such small samples is challenging. To achieve optimal loading of a molecule of interest in an array of reaction sites when the molecule's concentration is only approximately known, a titration series is typically performed: different dilutions of the sample are added to different arrays to determine which dilution produces the best loading. This titration generally must be repeated for each new sample, consuming sample, reagents, and time. Methods for loading samples that result in optimal loading without requiring either accurate concentration of the molecule to be loaded or a titration series are therefore desirable. The present invention fulfills these and other needs, as will be apparent upon review of the following. In some aspects, the invention provides methods for loading reaction sites in which loading is monitored and/or adjusted, such that a desired loading level can be achieved with a single sample aliquot and a single reaction site array.

The disclosure herein provides methods, compositions and systems for loading a desired number of reaction sites in an array with one or more molecules of interest.

For any of the loading methods described in the sections below, the reaction sites will in some aspects comprise an array of reaction sites, including an array of nanoscale wells, and the molecules of interest include polymerase enzyme complexes, where the complexes comprise template nucleic acids complexed with polymerase enzymes. For ease of discussion, the majority of the disclosure herein is directed to the loading of an array of nanoscale wells (also referred to herein as "nanowells") with template nucleic acids and/or complexes that include template nucleic acids, but it will be appreciated that any of the methods described herein are applicable to other types of reaction sites and other types of molecules.

In general, the methods described herein include delivering template nucleic acids to the array in a loading solution. In some examples, the loading solution includes one or more of: template nucleic acids, polymerase enzymes, primers, and nucleotides. In some examples, the template nucleic acids, polymerase enzymes, and primers are present in the loading solution as a complex that includes a primer hybridized to the template nucleic acid, and the nucleotides are present in the nanoscale wells either through the loading solution or separately from the loading solution. The nucleotides can be labeled or otherwise capable of generating a signal.

For any of the loading methods described herein, the array of nanoscale wells can be part of a substrate that is configured to allow detection of signals only from molecules within the wells themselves. In such a configuration, even if signals are being generated throughout the loading process, those signals will not be detected unless a complex is located within the nanoscale well itself. Such substrates include substrates of ZMWs, such as those described for example in U.S. patent application Ser. Nos. 10/259,268, 14/187,198, 14/107,730, 13/920,037, and U.S. Pat. Nos. 8,994,946, 8,906,670, 8,993,307, 8,802,600, 7,907,800, and 7,302,146, which are incorporated herein by reference in their entirety for all purposes and in particular for all teachings related to substrates and arrays of nanoscale wells. Such configurations provide a way to monitor how many wells of the array are occupied by at least one molecule. Monitoring the loading of the wells in this manner provides a way to assess the loading rate and efficiency while using only a single substrate for the assessment, which is a distinct advantage over methods that require multiple loading runs across multiple substrates to titrate the best concentrations and other loading solution characteristics to use for effective loading. In some examples, the loading methods described herein deliver molecules of interest, such as polymerase enzyme complexes, to the observation volume of the nanoscale wells. The "observation volume" generally refers to that volume of the nanoscale wells that is observable by whatever detection methods are used to detect signals from the wells. For example, in the case of fluorescence based detection, it is that volume which is exposed to excitation radiation and/or from which emission radiation is gathered by an adjacent optical train/detector. In some embodiments, the observation volume is an extremely small volume proximal to the base of a nanoscale well, e.g., a ZMW. See, e.g., U.S. Pat. Nos. 7,906,284 and 6,917,726, hereby incorporated by reference in their entirety.

For any of the loading methods described herein, determining whether a predetermined number of nanoscale wells has been loaded with a polymerase enzyme complex generally involves detecting signals generated by the polymerase enzyme complexes within the wells. Such signals indicate the number of wells across the array that are occupied by at least one active polymerase enzyme complex, and the level of occupancy (e.g., by a single or by multiple complexes) can further be determined for individual nanoscale wells if desired, e.g., based on the level of signals observed. Any component(s) of the polymerase enzyme complex can be labeled, e.g., with a fluorescent label or other moiety capable of generating a signal. For example, at least one of the polymerase, template, and primer can bear a label. In a particularly useful aspect, at least one labeled nucleotide analog is provided. Detection of the complex can then be accomplished by monitoring signals from the labeled analog.

For example, during sequencing by incorporation, e.g., single molecule sequencing by synthesis (SMS), nucleotide (or nucleotide analog) incorporation events are detected in real-time as the bases are incorporated into the extension product. This can be accomplished by immobilizing a synthesis complex, which includes a polymerase enzyme, such as a DNA polymerase enzyme, a template nucleic acid sequence, and a primer sequence that is complementary to a portion of the template sequence, within an optically confined space (e.g., an observation volume) or otherwise resolved as an individual molecular complex. Some SMS methods employ nucleotide analogs that include fluorescent labels coupled to the polyphosphate chain of the analog, which are then exposed to the complex. Upon incorporation, the nucleotide—along with its fluorescent label—is retained by the complex for a time and in a manner that permits the detection by a sequencing system of a signal "pulse" from the fluorescent label at the incorporation site. The sequentially detected signal pulses are then interpreted by the sequencing system to generate a readout corresponding to the sequence of the template nucleic acid. For a discussion of preferred sequence by incorporation processes, see, e.g., U.S. Pat. Nos. 6,056,661, 7,052,847, 7,033,764, 7,056,676, 7,361,466, the full disclosures of which are hereby incorporated herein by reference in their entirety for all purposes. Detection of signal pulses during loading can be detected as described for sequencing by incorporation, although it will be evident that pulses need not be interpreted to generate nucleotide sequence information where only level of loading is desired to be monitored.

In some embodiments, the nucleotide analog and a component of the polymerase complex (e.g., the polymerase) bear labeling components that interact via FRET to produce a signal only when the labeling components are in close proximity (e.g., during incorporation of the analog). In other embodiments, the nucleotide analog bears a label that is capable of generating a signal regardless of the label's proximity to the complex (e.g., a fluorescent label). Although a fluorescently labeled nucleotide analog can generate a signal whenever exposed to excitation light, in preferred embodiments, detectable signals are generated only within the observation volume of a nanoscale well.

Figure 5A:
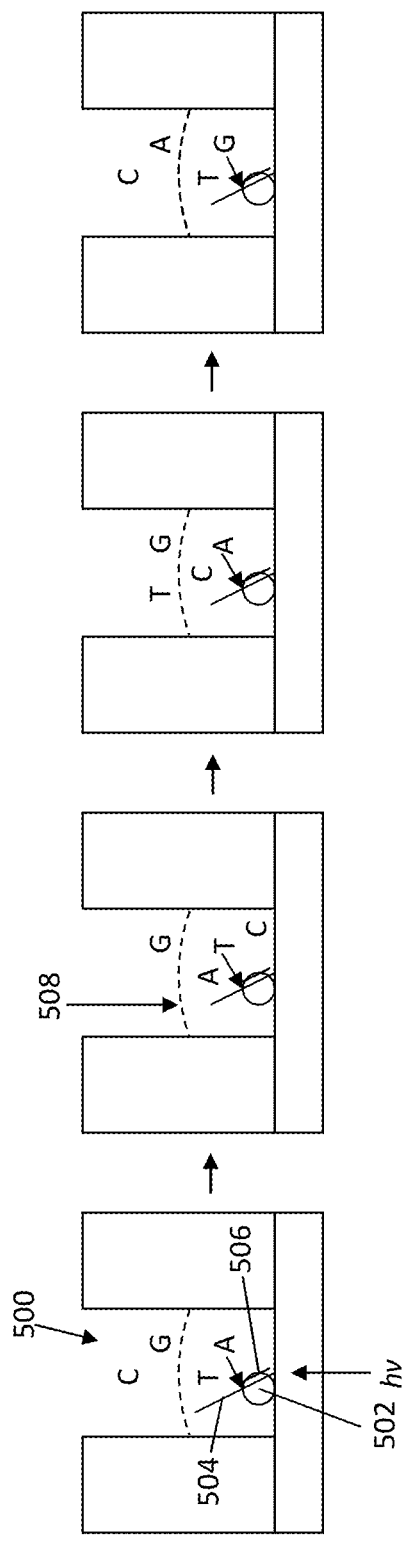
FIGS. 5A-5B schematically illustrate real-time monitoring of signals from a nanoscale well produced during incorporation of labeled nucleotide analogs.

As schematically illustrated in FIG. 5A, a nucleic acid synthesis complex, including a polymerase enzyme 502, a template sequence 504, and a complementary primer sequence 506, is provided immobilized within an observation region 500, that permits illumination (as shown by hv) and observation of a small volume that includes the complex without excessive illumination of the surrounding volume (as illustrated by dashed line 508). By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume.

Figure 5B:
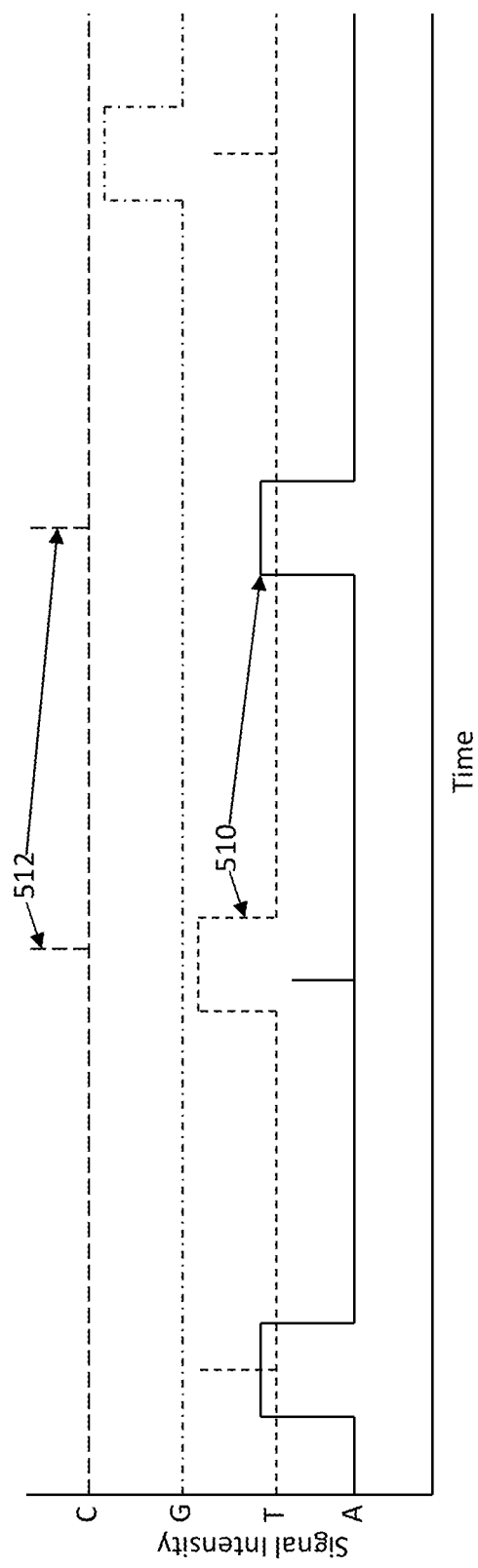

In particular, as shown in FIG. 5B, when a nucleotide, e.g., A, is incorporated into by the polymerase, it is retained within the observation volume for a prolonged period of time, and upon continued illumination generates a prolonged fluorescent signal (shown by pulse or peak 510). By comparison, randomly diffusing and not incorporated nucleotides remain within the observation volume for much shorter periods of time, and thus produce only transient signals (such as peak 512), many of which go undetected, due to their extremely short duration.

In particularly preferred exemplary systems, the confined illumination volume is provided through the use of arrays of optically confined apertures termed zero-mode waveguides (ZMWs), e.g., as shown by confined reaction region 500. See, e.g., U.S. Pat. No. 6,917,726, which is incorporated herein by reference in its entirety for all purposes. For sequencing applications, the DNA polymerase is typically provided immobilized upon the bottom of the ZMW. See, e.g., Korlach et al. (2008) PNAS U.S.A. 105(4):1176-1181, which is incorporated herein by reference in its entirety for all purposes. In operation, the fluorescently labeled nucleotides (shown as A, C, G and T) bear one or more fluorescent dye groups on a terminal phosphate moiety that is cleaved from the nucleotide upon incorporation. As a result, synthesized nucleic acids do not bear the build-up of fluorescent labels, as the labeled polyphosphate groups diffuses away from the complex following incorporation of the associated nucleotide, nor do such labels interfere with the incorporation event. See, e.g., Korlach et al. (2008) Nucleosides, Nucleotides and Nucleic Acids, 27:1072-1083.

Signal pulses can thus be generated by incorporation of labeled nucleotide analogs into a nascent strand. In other embodiments, signal pulses are generated as a labeled nucleotide analog is retained in the polymerase complex without being incorporated; such cognate sampling methods are described in greater detail below.

Determining the number of nanoscale wells loaded with a polymerase enzyme complex can be conducted by monitoring signals from the nanoscale wells continuously throughout the loading process or intermittently at different intervals during the loading process. For intermittent methods, the detection can be conducted at one or more fixed time points during the loading process or randomly as needed to ascertain the level of occupancy of the nanoscale wells. (Intermittent monitoring can be beneficial since minimizing the total time for which the complex is illuminated can minimize photodamage.) Similarly, determining the number of nanoscale wells loaded with a polymerase enzyme complex can involve monitoring signals from all of the wells in the array, or signals from a subset of the wells can be monitored and the fraction of wells in the that subset that are occupied by at least one complex can be determined. The fraction of occupied wells in the entire array is assumed to be equal to the fraction of occupied wells in the subset; the number of occupied wells in the entire array can thus be calculated.

In certain examples and as is described in further detail herein, methods of loading a predetermined number of nanoscale wells with polymerase enzyme complexes involve real-time monitoring as the loading solution is delivered to the array—e.g., the number and/or proportion of nanoscale wells loaded with a complex is monitored in real-time. The rate at which the loading solution is delivered to the array and/or the length of time that the loading solution remains in contact with the array can be altered as needed to continue to load the nanoscale wells until a predetermined number of wells are occupied. In certain examples of such real-time loading processes, the polymerase enzymes in the loading solution are maintained in an inactive state, such that the association of a cognate nucleotide (also referred to as a "cognate base") to the next available base on the template nucleic acid (the templating base) results in a detectable signal, but that cognate nucleotide is not added to a nascent strand by the inactive polymerase—e.g., a chemical linkage is not formed and the cognate base will eventually be released, but another cognate base will be able to associate with its complement on the template and generate a further signal. In related examples of real-time loading processes, an unincorporatable nucleotide analog is provided as the cognate nucleotide. Cognate interactions and the resultant signals from non-incorporation events are further described in the art, for example in U.S. Pat. Nos. 8,252,911 and 8,530,164, which are herein incorporated by reference in their entirety for all purposes and in particular for all teachings related to compositions and methods for use in reactions that involve interactions between incorporatable and non-incorporatable nucleotides and incorporation and non-incorporation events when such nucleotides interact with polymerases. In some examples, the polymerase can be maintained in an inactive state by including additives in the loading solution, such as divalent cations (including without limitation strontium or calcium) that act to inactivate the polymerase. Once the desired number of nanoscale wells is loaded, the loading solution can be washed away and replaced with a buffer that does not contain the inactivating cations or unincorporatable nucleotide analogs, allowing further use of the loaded complexes (for example in sequencing reactions).

In certain other examples and as described in further detail herein, methods of loading a predetermined number of nanoscale wells with polymerase enzyme complexes can involve loading multiple complexes into wells and then in a controlled manner inactivating and/or effectively removing active polymerase enzyme complexes until a predetermined number of nanoscale wells contain a single active complex. In such methods, the process includes steps of first loading the array with a concentration of polymerase enzyme complexes that is high enough to overload the wells—in other words, a concentration of complexes is used that statistically will result in multiple complexes loaded into the majority of nanoscale wells in the array. In some cases, a number of complexes are then inactivated by accelerating photodamage, generally by application of a light source such as a laser pulse. In other cases, complexes are inactivated through random termination of the processing ability of the polymerase enzymes, generally by adding extension terminating agents to the nanoscale wells. Regardless of the method of inactivation, the inactivation process is continued until a predetermined number of nanoscale wells contains a single active polymerase enzyme complex. At that point, the inactivation process is ceased and the array can then be further processed for downstream applications, such as sequencing reactions to identify the nucleotide sequence of template nucleic acids that are part of the polymerase enzyme complexes.

In certain other examples and as described in further detail herein, methods of loading a predetermined number of nanoscale wells with polymerase enzyme complexes involve modulating the activation state of the polymerase enzyme in the complex. In such examples, the polymerase enzyme complex contains a polymerase enzyme complexed to a template nucleic acid, and the polymerase enzyme is in an inhibited state during the loading process. Once the polymerase enzyme complex is within a nanoscale well, the inhibition is released and the polymerase enzyme complex is able to at that point start generating signals. The signals are monitored and the release of inhibition is continued across the array until the level of signaling indicates that a predetermined number of nanoscale wells contain a single active polymerase enzyme complex. Any mechanism by which a polymerase enzyme complex can be retained in an inhibited state that can then be controllably released once the complex is in a nanoscale well can be used in accordance with these exemplary loading methods. In some situations, the polymerase enzyme complex includes a polymerase enzyme complexed to a template nucleic acid, and the template nucleic acid is further hybridized to a primer. In some situations, the inhibition of the complex is modulated by a nonhydrolyzable nucleotide analog that is linked to the primer by a tether, and inhibition is released by cleaving that tether. In further examples, the tether may be photocleavable or susceptible to cleavage by agents such as proteases, restriction endonucleases, RNAses, and the like.

In certain other examples and as described in further detail herein, methods of loading a predetermined number of nanoscale wells with polymerase enzyme complexes involve altering the immobilization of complexes with the nanoscale wells. In such methods, the polymerase enzyme complexes are delivered to an array of nanoscale wells and immobilized within the wells through a cleavable linker. In general, such immobilization occurs within an observation volume of the nanoscale well. The polymerase enzyme complexes are then exposed to a cleavage agent for a period of time until a predetermined number of the nanoscale wells contain a polymerase enzyme complex.

The above aspects and further exemplary embodiments are described in further detail in the following discussion.

II. Real-Time Monitoring During Loading

In one aspect, the present disclosure provides methods for monitoring the loading of nanoscale wells with polymerase enzyme complexes in real time, allowing for control and adjustment of factors such as the length of time for which a substrate is exposed to a loading solution, the volume or concentration of loading solution provided to the substrate, and/or rate of loading to ensure that a predetermined number of nanoscale wells contain a polymerase enzyme complex.

In general, the methods described herein for real-time loading of the array of nanoscale wells result in a predetermined number of nanoscale wells being loaded with a polymerase enzyme complex. In such methods, a loading solution containing polymerase enzyme complexes is loaded onto the surface of an array of nanoscale wells under conditions that allow for signal pulses to be generated. In general, the polymerase enzyme complexes comprise a template nucleic acid complexed with a polymerase enzyme, and the signal pulses are generated during interactions between labeled nucleotides or nucleotide analogs and their cognate bases on the template nucleic acids. The labeled nucleotides or nucleotide analogs can, in some embodiments, be incorporated into a nascent strand. In other embodiments, the nucleotides or analogs are not incorporated. As the loading solution remains in contact with the surface of the array, the nanoscale wells can be monitored to detect signal pulses from within the wells, and detection of those signal pulses identifies nanoscale wells that have been loaded with a polymerase enzyme complex (i.e., at least one polymerase enzyme complex).

In some embodiments, the predetermined number of loaded nanoscale wells is achieved by maintaining contact of the loading solution with the array until signals can be detected from the predetermined number of nanoscale wells—in other words, time of loading is altered/extended to reach the goal percentage of loaded nanoscale wells. Contact time sufficient to reach the desired number of loaded wells can be determined, e.g., by continuous monitoring or intermittent monitoring, optionally along with comparison to a standard loading curve or a model. For example, in one class of embodiments, signals are monitored after loading is initiated, e.g., at one or more time points, typically soon after loading is initiated. (For example, the number of occupied wells can be determined at 1-10 time points, e.g., 2-10 or 2-5 time points, e.g., within 5-60 minutes or 10-30 minutes after loading is initiated, e.g., one at 10 minutes and one at 30 minutes.) A curve is fit to this initial loading data and used to predict the time needed to achieve the desired level of loading. (See, e.g., FIG. 19 and Example 1 hereinbelow.) Additional monitoring can but need not be performed to confirm achievement of this level. In some embodiments, the predetermined number of loaded nanoscale wells is achieved by adding additional polymerase enzyme complexes to the loading solution or removing excess complexes from the loading solution or from the wells. In certain embodiments, a combination of time of loading and supplementation (or removal) of polymerase enzyme complexes is used to load a predetermined number of nanoscale wells with polymerase enzyme complexes.

In some embodiments, the nanoscale wells are loaded with multiple polymerase enzyme complexes and the number of occupied nanoscale wells is further tuned by allowing the complexes to continue generating signals until a fraction of the complexes have gone inactive through dissociation, photodamage, or other time-related inactivation. In other words, the tuning of the loading is further geared toward singly-occupied nanoscale wells by allowing multiply loaded wells to revert to containing only a single active polymerase complex by passage of time.

In some embodiments, "cognate sampling" methods are used to detect whether a nanoscale well contains a polymerase enzyme complex. In such methods, a labeled cognate nucleotide or nucleotide analog is able to associate with the next available base on the template nucleic acid, thus generating a detectable signal pulse. However, the cognate nucleotide is not added to a nascent strand, and thus a chemical linkage is not formed and the cognate base will eventually release, but another cognate base will be able to associate with its complement on the template and generate a further signal. In some embodiments, this type of cognate sampling is achieved through non-incorporation of labeled nucleotide analogs by including additives such as noncatalytic divalent cations in the loading solutions to keep the polymerase enzyme unable to add a cognate nucleotide to a nascent strand. Such noncatalytic divalent cations can include one or more of strontium, cobalt, tin, calcium, nickel, europium, barium, iron, and zinc, which can act to retain the polymerase in the polymerase enzyme complex in an inactivated state, such that the association of a cognate nucleotide (also referred to as a "cognate base") to the next available base on the template nucleic acid produces a signal, but that cognate nucleotide is not added to a nascent strand by the inactive polymerase. Divalent cations are typically provided as a salt comprising the relevant cation, e.g., calcium acetate or strontium acetate. In some embodiments, the non-incorporation is achieved by using a nonhydrolyzable nucleotide analog that cannot be incorporated into a nascent strand. (Nucleotides that can be incorporated are optionally also provided, e.g., at substantially lower concentrations than the unincorporatable analog(s) and/or corresponding to other templating bases. In embodiments in which the unincorporatable nucleotide is labeled, any incorporatable nucleotides are typically unlabeled.) Such interactions and the resultant signals from non-incorporation events are further described in the art, for example in U.S. Pat. Nos. 8,252,911, 8,530,164, and 8,652,781, which are herein incorporated by reference in their entirety for all purposes and in particular for all teachings related to compositions and methods for use in reactions that involve interactions of polymerase enzyme complexes with incorporatable and non-incorporatable nucleotides as well as incorporation and non-incorporation events between such nucleotides and polymerases.

A schematic illustration of an exemplary embodiment of a real-time monitoring method employing cognate sampling is provided in FIG. 1. In such methods, a nanoscale well 101 has a polymerase enzyme complex (102) delivered into it. A labeled nucleotide analog (105) binds to its cognate base, as shown in (103), resulting in detection of a signal (107) during the time the analog occupies the site. When the analog leaves the site as shown in (104), the signal drops back to baseline. As more analogs occupy the cognate base site, more signal pulses will be generated, indicating occupancy of the nanoscale well. Similar signals are generated across the array, providing a way to monitor the level of occupancy across the nanoscale wells of the array. As will be appreciated, the level of occupancy can be monitored continuously throughout the loading process or intermittently. Intermittent monitoring may be accomplished at fixed time points during the loading process or sporadically or randomly as needed to determine the level of occupancy of the nanoscale wells.

Monitoring the signals generated during the interactions of the cognate bases with the template nucleic acids can include without limitation detection and measurement of characteristics such as signal intensity and pulse width. The signals generated from cognate sampling generally have a high signal to noise ratio that lasts for a relatively extended period of time, for example on the order of seconds (see FIG. 1 and FIG. 2A), which allows for a clear indication that a nanoscale well has been loaded with a complex.

In some embodiments, the cognate bases included in the loading solution include all four possible nucleotides (A, C, T, G) or analogs thereof, to allow for signals to be generated by interactions between the cognate bases and the template nucleic acids regardless of the identity of the next available base on the template nucleic acid (e.g., where, prior to loading, the polymerase has pre-extended a primer hybridized to the template). One, two, three, or all four of the nucleotides or analogs can be labeled or otherwise capable of generating a signal. In certain embodiments, the template nucleic acids have a structure that allows for control over the identity of the next available base on the template nucleic acids. For example, the template nucleic acids may include an adapter that includes a primer binding site positioned in such a way as to ensure that the next available base on the template is always a pre-defined base, such as a thymine. The population of cognate bases in the loading solution may then include all four bases, in which only the adenine (or an A-analog) is labeled or is otherwise capable of generating a signal, or the cognate bases may include only the labeled adenine or adenine analog. In either of these exemplary embodiments, a signal is detected when the proper labeled cognate base is associated with its complement on the template nucleic acid.

In some embodiments, the template nucleic acids include nucleic acids from multiple different sources, and the template nucleic acids are structured such that the next available base for interaction with a cognate base identifies the source of the template nucleic acid. In other words, the signals generated by interaction of a particular template nucleic acid with the appropriate cognate base not only indicates that a nanoscale well has been loaded, but also what the source of the loaded template nucleic acid is, based on the cognate base that generates the signal. For example, nucleic acids from a first source (or set of sources) can be prepared for sequencing using a first adapter in which the next base after the primer binding site is a T, while nucleic acids from a second source are prepared for sequencing using a second adapter in which the next base after the primer binding site is an A, those from a third source using a third adapter in which the next base after the primer binding site is a C, and those from a fourth source using a fourth adapter in which the next base after the primer binding site is a G. In such an embodiment, it will be appreciated that any combination of cognate bases and distinguishable labels useful for such a multiplex reaction can be used. In some embodiments, the template nucleic acids contain a hairpin loop at one or both ends or are circular constructs or SMRTbell™ constructs (circular nucleic acids having a double-stranded central region and single-stranded hairpin ends) as described herein.

In some embodiments, signal pulses produced while a labeled nucleotide is being incorporated into a nascent strand are used to detect whether a nanoscale well contains a polymerase enzyme complex. For example, at least one labeled nucleotide analog can be provided and signal pulses detected as the analog is retained in the observation volume during incorporation by the polymerase, as schematically illustrated in FIGS. 5A-5B. As for the embodiments above, monitoring the signals generated during incorporation of the cognate nucleotides can include without limitation detection and measurement of characteristics such as signal intensity and pulse width. In some embodiments, detection of pulses due to incorporation events can be facilitated by slowing the polymerase, for example, by decreasing nucleotide analog concentration or by including a nucleic acid condensing agent in the loading solution (e.g., polyethylene glycol and a divalent cation; see, e.g., US patent application publication 2017/0136433), or broadening pulse width by inclusion of $Li^{2+}$ in the loading solution (see, e.g., U.S. Pat. No. 8,986, 930).

As will be appreciated, the methods described herein for loading and monitoring the loading of arrays can be altered and elaborated upon depending on the types and concentrations of molecules that are being loaded and the size and structure of the arrays. In general, there can be an inverse relationship between the concentration of molecules to be loaded and the time that is required to load enough of the reaction sites in the array to be of use for downstream applications such as sequencing reactions. Thus, larger concentrations of molecules in the loading solution will generally result in shorter loading times needed to occupy a predetermined number of reaction sites. In some embodiments, the concentration of molecules (such as polymerase enzyme complexes that include a polymerase enzyme complexed to a template nucleic acid, which is optionally further associated with a primer) in the loading solution is about 1 fM-50 pM, e.g., 10 fM-20 pM, 100 fM-30 pM, 1 pM-5 pM, 1 pM-10 pM, 5 pM-40 pM, 10 pM-35 pM, 15 pM-30 pM, or 20 pM-25 pM. As discussed above, an advantage of the methods described herein, which allow monitoring of loading in real time based on the signal generated by polymerase enzyme complexes within the nanoscale wells, is that use of a single array provides information on how best to load a particular array in terms time for loading where concentration may not be accurately known. Such information in other systems that do not allow this level of assessment often requires a titration across multiple arrays. Thus these described methods provide a way to increase efficiency and speed in terms of loading an array and having it be ready for use for downstream applications.

The real-time monitoring/loading method can be carried out in the presence of one or more agents that function to block or otherwise minimize the pathways that lead to photodamage from prolonged illumination. The agents can be present in the loading solution or in nanoscale wells prior or subsequent to delivery of the loading solution to the array. Such agents include reducing agents or anti-fade agents that prevent the formation of triplet state fluorophores (also referred to as triplet state quenchers), as well as oxygen scavenging agents that remove oxygen and reactive oxygen species from the reaction mixture, thus preventing downstream damage to enzymes within the system. In general, the photodamage mitigating agents are present at levels sufficient to provide beneficial impact, e.g., reduced photodamage, but are not present at such levels as to interfere with the reaction of interest, e.g., the generation of signal pulses as described above.

A variety of reducing agents or anti-fade agents may be used as triplet state quenchers, including, for example, ascorbic acid, dithiothreitol (DTT), mercaptoethylamine (MEA), β-mercaptoethanol (BME), n-propyl gallate, p-phenylenediamene (PPD), hydroquinone, sodium azide ($NaN_3$), and diazobicyclooctane (DABCO), as well as commercially available anti-fade agents, such as Fluoroguard (available from BioRad Laboratories, Inc., Hercules, Calif.), Citifluor antifadants (Citifluor, Ltd., London, UK), ProLong, Slow-Fade, and SlowFade Light (Invitrogen/Molecular Probes, Eugene, Oreg.).

Likewise, a number of singlet oxygen quenchers may be used to eliminate or reduce reactive oxygen species, including, for example, enzymatic systems, e.g., superoxide dimutase, glucose oxidase/catalase (GOD/CAT), oxidase/ peroxidase enzyme systems, e.g., glucose oxidase, alcohol oxidases, cholesterol oxidases, lactate oxidases, pyruvate oxidases, xanthine oxidases, and the like, in combination with peroxide depleting enzymes, like horseradish peroxidase (HRP), glutathione peroxidase, or combinations of these with other enzymes, protocatechuate 3,4 dioxygenase (PCD), or thiol based quenchers, e.g., ergothioneine, methionine, cysteine, beta-dimethyl cysteine (penicillamine), mercaptopropionylglycine, MESNA, glutathione, dithiothreitol (as noted above for a reducing agent), N-acetyl cysteine and captopril (see, e.g., Biochem Soc. Trans. 1990 December; 18(6): 1054-6). Any additional substrates needed for oxygen depleting enzyme systems are also provided, e.g., glucose for glucose oxidase, lactate for lactate oxidase, protocatechuic acid (PCA) for protocatechuate 3,4 dioxygenase, and the like. Also, biological singlet oxygen quenchers may be employed such as lycopene, gamma-carotene, astazanthin, canthazanthin, alpha-, beta-, and gamma-carotene and their analogs (see, e.g., Carcinogenesis vol. 18 no. 1 pp. 89-92, 1997), bixin, zeaxanthin, lutein, bilirubin, biliverdin, and tocopherols (see, e.g., Biochem Soc Trans. 1990 December; 18(6): 1054-6 ref.), as well as polyene dialdehydes (Carcinogenesis vol. 18 no. 1 pp. 89-92, 1997)

melatonin, and vitamins E (alpha-tocopheryl succinate and its analogs) and B6 (pyridoxine) and its derivatives). Other chemical oxygen scavengers are also available, e.g., hydrazine ($N_2H_4$), sodium sulfite ($Na_2SO_3$), hydroxylamine, glutathione, N-acetylcysteine, and the like. In addition to the foregoing, in many cases, the amount of singlet oxygen quenchers or scavengers may be reduced or eliminated by physically excluding oxygen from the reaction of interest by, e.g., degassing reagents, perfusion with inert gases, or the like. In addition to the foregoing, as an additional or alternative to the foregoing compounds, anti-oxidants may also be provided in the reaction mixture, including, e.g., Trolox and its analogs U-78715F and WIN62079, a soluble form of vitamin E, having a carboxyl substitution, or in the case of analogs, other substitutions, in place of the vitamin E phytyl side chain, ascorbic acid (or ascorbate), butylated hydroxytoluene (BHT), and the like. In certain aspects, the loading methods may be carried out in the presence of combinations of agents, including one or more of a reducing agent, such as DTT, MEA, or BME, and an oxygen scavenger, such as GO-Cat. Additional exemplary photodamage mitigating agents and suitable combinations thereof are described, e.g., in U.S. Pat. Nos. 7,998,717, 8,071,346, 9,637,782, and 7,993,895 and U.S. Patent Application Publication Nos. 20100003765, 20100136592, 20120052488, and 20170145494, which are hereby incorporated by reference in their entirety.

In some embodiments, the polymerase enzyme complexes are immobilized in the nanoscale wells (e.g., in the observation volume). Such immobilization may be a continuous process that occurs throughout the time that the loading solution is in contact with the array. In other embodiments, immobilization takes place after the predetermined number of nanoscale wells has been determined to contain a polymerase enzyme complex. In some embodiments, the polymerase enzyme complexes comprise a reactive element, and immobilizing occurs through an interaction of the reactive element and a binding site in the nanoscale well. Exemplary reactive elements include streptavidin and other biotin-binding proteins such as avidin, deglycoslylated avidin (NeutrAvidin), traptavidin, tamavidin, rhizavidin, or a variant, mutant, or derivative thereof, and exemplary binding sites comprise biotin or a biotin analog such as a biotin sulfoxide, iminobiotin, desthiobiotin (also known as dethiobiotin), oxybiotin, carbobiotin, selenobiotin, carboxybiotin, homobiotin, norbiotin, diaminobiotin, biotin sulfone, epibiotin, 5-hydroxybiotin, 2-thiobiotin, azabiotin, methylated derivatives of biotin (e.g., biotin methyl ester), and/or ketone biotin. Additional useful reactive element/binding site pairs include the many specific binding partners known in the art, e.g., where one member of a specific binding pair is the binding site attached to the surface (or is attached to a coupling group that is attached to the surface), and the other member of the binding pair is the reactive group attached to or integral with the polymerase complex. Such binding pairs can include small molecule coupling groups and/or macromolecular coupling groups, e.g., antibodies, antibody fragments, epitopes, binding peptides, lectins, complementary nucleic acids, or any of a variety of other binding groups.

Figure 6:
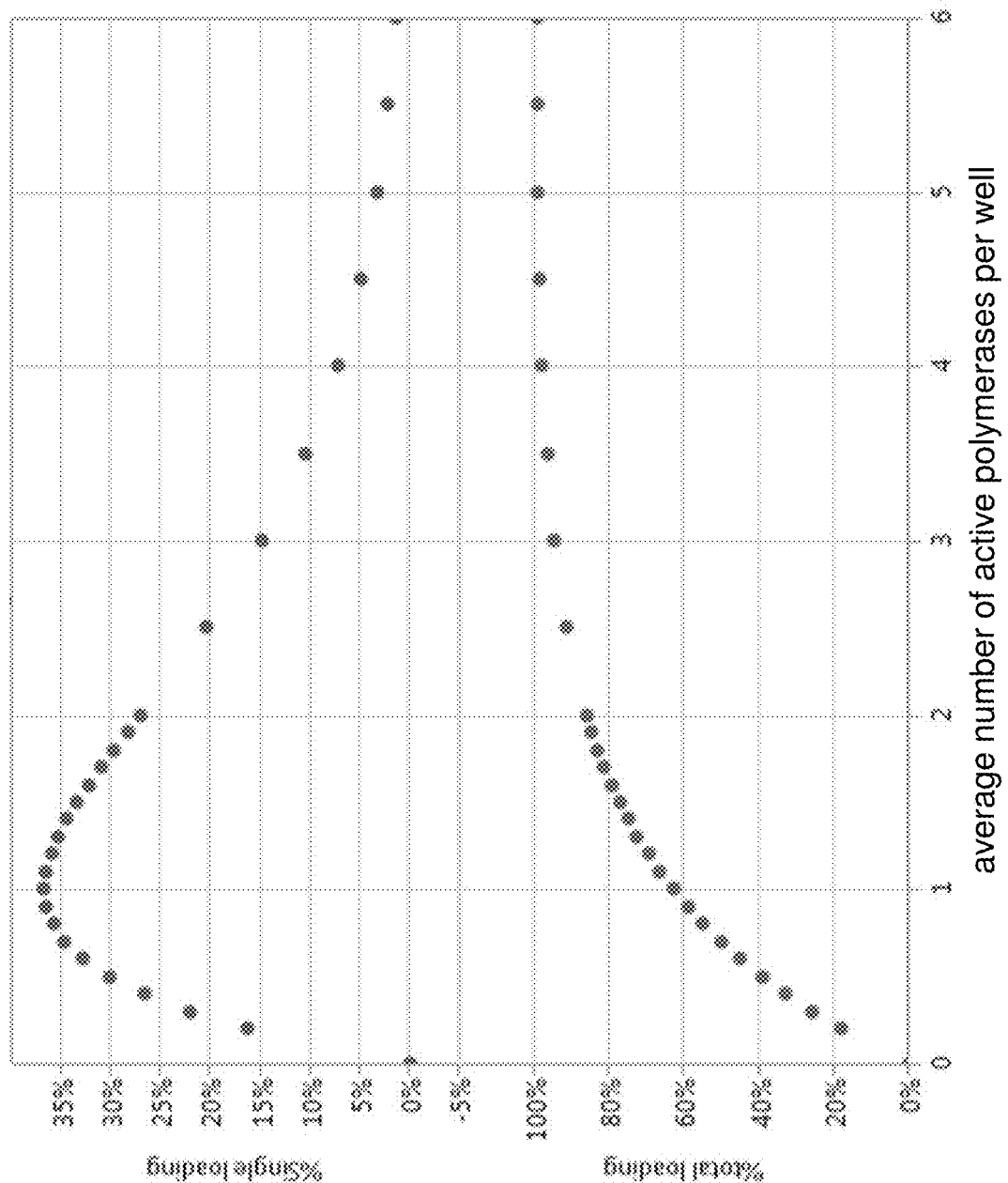
FIG. 6 presents graphs showing the percentage of wells calculated to be occupied by a single polymerase enzyme complex (top) and the percentage of wells calculated to be occupied by at least one polymerase enzyme complex (bottom) as the average number of polymerase enzymes per well increases.

As discussed above, methods involving real-time monitoring of loading utilize changing factors such as time of loading as well as optional addition of further reagents to load a predetermined number of nanoscale wells with a polymerase enzyme complex. Without limitation to any particular mechanism, as illustrated in FIG. 6, the Poisson distribution generally governs passive diffusion loading techniques. As the average number of polymerase complexes per well in an array increases, the fraction of wells in the array that are occupied by at least one polymerase enzyme complex also increases, from 0 to 100%, e.g., as shown in the bottom graph in FIG. 6. The fraction of wells in the array that are occupied by a single complex initially increases as well, but then decreases again as the wells are more heavily loaded, e.g., as shown in the top graph in FIG. 6. In some embodiments, the number of wells occupied by a polymerase enzyme complex (that is, by at least one complex) is counted, while in other embodiments, the number of wells occupied by a single polymerase enzyme complex is counted. As shown in FIG. 6, these two quantities are both related to the average number of polymerase complexes per well. Either the number of wells occupied, the number of wells occupied by a single active complex, and/or the average number of active polymerase complexes per well can thus be monitored, as convenient or as desired for a particular application. Thus, for example, references herein to determining the number of wells containing a single active polymerase enzyme complex explicitly includes performing the determination by determining the average number of polymerases per well and/or by determining the number of wells occupied by at least one active polymerase enzyme complex (since the average single loaded occupancy can be calculated from the total number of loaded wells using the Poisson distribution). Distinguishing between multiply loaded and singly loaded wells can be accomplished, e.g., by monitoring the level of signal from the wells and/or analyzing the signal traces. Optionally, the average number of active complexes per well can be calculated based on an average level of signals detected from at least a plurality of the nanoscale wells.

In some embodiments, the methods described herein for real-time loading of nanoscale wells are conducted until a predetermined number of the nanoscale wells in the array contain a polymerase enzyme complex (whether a single complex or more than one complex). For example, the predetermined number of nanoscale wells in the array occupied by a polymerase enzyme complex can be at least about 10%, at least about 20%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the nanoscale wells in the array. In some embodiments, the predetermined number of nanoscale wells occupied by a polymerase enzyme complex is about 10-100% of the nanoscale wells in the array, e.g., about 30-95%, about 35-90%, about 40-80%, about 45-85%, about 50-75%, about 55-70%, or about 60-80% of the nanoscale wells in the array. In some embodiments, at least a majority of the predetermined number of nanoscale wells are occupied by a single polymerase enzyme complex.

In some embodiments, the methods described herein for real-time loading of the nanoscale wells are conducted until a predetermined number of the nanoscale wells in the array contain a single polymerase enzyme complex (typically, a single active polymerase enzyme complex). For example, the predetermined number of nanoscale wells in the array occupied by a single polymerase enzyme complex can be at least about 10%, at least about 20%, at least about 25%, at least about 30%, or at least about 35% of the nanoscale wells in the array. In some embodiments, the predetermined number of nanoscale wells occupied by a single polymerase enzyme complex is about 10-40% of the nanoscale wells in the array, e.g., about 20-35% of the nanoscale wells in the array.

In some embodiments, the methods described herein for real-time loading of the nanoscale wells are conducted until the average number of active polymerase complexes per well is about 0.7, about 0.8, about 0.9, about 1, about 1.1, about 1.2, about 1.3, about 1.4, about 1.5, about 1.6, about 1.7, about 1.8, about 1.9, or about 2 or more. In some embodiments, the methods described herein for real-time loading of the nanoscale wells are conducted until the average number of active polymerase complexes per well is about 0.8-2, e.g., about 1-1.8 or about 1.2-1.6.

In some embodiments, the loading solution comprises polymerase enzyme complexes including template nucleic acids from a single source or sample. In other embodiments, the polymerase enzyme complexes to be loaded on the array include template nucleic acids from multiple different samples or sources (e.g., from different individuals, tissues, time points, collection sites, treatment types, and/or the like). The different templates can be uniquely identified through use of barcoded adapters, barcoded primers, or the like as is well known in the art. The polymerase enzyme complexes can be mixed in a single loading solution which is applied as detailed herein, for subsequent multiplex analysis of the different templates. As another example, however, loading solutions comprising different templates (or different mixtures of templates) can be applied iteratively. For example, a first loading solution comprising polymerase enzyme complexes including a first template (or first mixture of templates) can be applied as detailed above. Once a predetermined number of the wells have been loaded with these complexes (e.g., 10% of the wells), the array can be washed to remove the first loading solution. A second loading solution comprising polymerase enzyme complexes including a second template (or second mixture of templates) can then be applied. Again, once a predetermined number of the wells have been loaded (e.g., 20% of the wells), the array can be washed to remove the second loading solution. A third loading solution comprising polymerase enzyme complexes including a third template (or third mixture of templates) can then be applied. Again, when a predetermined number of the wells have been loaded (e.g., 30% of the wells), the array can be washed to remove the third loading solution, and so on as desired.

The techniques described herein can be combined with other techniques for loading molecules or complexes into nanoscale wells, including techniques for achieving "Super-Poisson" loading in which a greater number of wells contain a single active polymerase than in techniques governed solely by the Poisson distribution. See, e.g. U.S. Pat. No. 8,906,831 and U.S. Patent Application Publication 20160310926. Thus, in certain embodiments, more than 37% of the nanoscale wells contain a single active polymerase enzyme. Similarly, loading techniques involving nucleic acid condensing agents (e.g., polyethylene glycol and a divalent cation), magnetic beads, high density solutions, or the like can be employed in combination with any of the methods of the invention. See, e.g., U.S. Pat. No. 8,715,930 and U.S. Patent Application Publications 20170136433 and 20170159119.

Once the predetermined number of nanoscale wells are occupied by polymerase enzyme complexes, the array can then be washed and further processed to prepare the array for downstream applications, such as sequencing reactions. For use in sequencing-by-synthesis reactions, the wash steps can include washing with buffers to remove any metal ions maintaining the polymerases in an inactive state, unincorporatable nucleotide analogs, additives that slow the polymerase, and/or like reagents employed during loading, thus allowing incorporation of nucleotides and nucleotide analogs and the generation of sequencing signals as the polymerases form nascent strands. The wash and further processing steps can include any steps useful for any of the sequencing reactions described herein and known in the art. In certain exemplary embodiments, the sequencing reactions include the steps of providing one or more nucleotides or nucleotide analogs (e.g., labeled analogs); performing a polymerization reaction in which the polymerase enzyme replicates at least a portion of the template nucleic acid in a template-dependent manner, whereby one or more of the nucleotides or nucleotide analogs are incorporated into the resulting nucleic acid; and identifying a time sequence of incorporation of the one or more nucleotide or nucleotide analogs into the resulting nucleic acid.

III. Tuning Single Molecule Loading by Inactivating Polymerase Complexes

In one aspect, the present disclosure provides methods for establishing active polymerase enzyme complexes (e.g., single active polymerase enzyme complexes) in a predetermined number of nanoscale wells through controlled, progressive inactivation of polymerase enzyme complexes to result in singly occupied wells. In general, such methods include the step of delivering multiple complexes into a plurality of the nanoscale wells and then, in a controlled manner, inactivating enough polymerase enzymes across an average number of the nanoscale wells to result in a predetermined number of the nanoscale wells containing at least one active polymerase enzyme complex, optionally a single active polymerase enzyme complex. In certain aspects, the polymerase enzyme complexes are delivered to the array of nanoscale wells at a concentration that overloads the array, e.g., results in a majority of nanoscale wells containing two or more polymerase enzyme complexes. Subsequent methods to inactivate a portion of the complexes, which are described in further detail below, can then be used to tune the level of occupancy such that a predetermined number of the nanoscale wells contain a single active complex.

In some aspects, the methods include inactivating the polymerase enzymes by inducing photodamage through exposure to light. In other aspects, the polymerase enzymes are inactivated by adding extension terminating reagents (such as dideoxy nucleotides) to the reaction sites to randomly inactivate a fraction of the active complexes in the nanoscale wells. Regardless of the method of inactivation used, the result is that a sufficient average number of polymerase enzymes are inactivated such that a predetermined number of the nanoscale wells have a single active polymerase enzyme complex remaining.

In certain embodiments, prior to the methods of inactivation described in further detail below, the polymerase enzyme complexes are delivered to observation volumes within nanoscale wells. In some embodiments, the polymerase enzyme complexes are immobilized within the observation volumes prior to or simultaneously with the procedures described in further detail herein regarding inactivating a plurality of the polymerase enzymes to result in a predetermined number of nanoscale wells containing a single complex. The immobilizing can be accomplished using any methods known in the art and described herein. In certain embodiments, the polymerase enzyme complexes comprise a reactive element and the immobilizing occurs through an interaction of that reactive element and a binding site in the nanoscale well. In some embodiments, the reactive element comprises streptavidin and the binding site comprises biotin. Additional exemplary reactive elements and binding sites have been described hereinabove.

The progress of inactivating the polymerase enzyme complexes can be monitored by detecting signals from within the nanoscale wells, e.g., from the observation volume of the nanoscale wells. In some embodiments, as detailed above, such signals are generated by interactions occurring within the loaded wells between the polymerase enzyme complexes and labeled nucleotides and/or nucleotide analogs that are also located within the nanoscale wells. In exemplary embodiments, the labeled nucleotide analog is added to a nascent strand complementary to the complexed template nucleic acid. Signal is detected as the labeled analog is retained in the complex during incorporation. In other embodiments, signals are a result of cognate sampling, also as described above. While active polymerase complexes can generate signals, e.g., through incorporation or cognate sampling, inactive complexes (e.g., photodamaged complexes, complexes inactivated by termination, etc.) are unable to generate signals. The progress of the inactivation can be monitored continuously or intermittently by detecting signals from the remaining active polymerase enzyme complexes.

In certain aspects, the polymerase enzyme complexes are inactivated by inducing photodamage to the polymerase enzyme complexes, particularly the polymerase enzymes of those complexes. Such methods can include any methods of inducing photodamage to enzymes, including for example the application of laser pulses. Such laser pulses can damage or inactivate polymerase enzymes and thus interfere with their ability to generate signals by detracting from their ability to add labeled nucleotides or nucleotide analogs to a nascent strand. In some embodiments, the array of nanoscale wells is exposed to oxygen to accelerate photodamage inflicted on the polymerase enzyme complexes. For example, loading can be conducted in the absence of photodamage mitigating agents such as reducing agents, oxygen scavengers, and/or nitrogen.

The level of inactivation through photodamage can be tuned by altering the illumination level. For embodiments in which laser pulses are used, the tuning can be accomplished by tuning the level of the laser power. Laser power (or optical power from another light source) can be increased to accelerate or decreased to retard the rate of photodamage. Optionally, the methods include monitoring signals from the polymerase enzyme complexes and, depending on how the signal changes over time, altering the optical power to adjust the rate of photodamage.

In some embodiments, monitoring of the level of inactivation of the complexes (and thus the level of occupancy) comprises calculating the average number of active complexes per well based on the average level of signals that are detected from at least a plurality of the wells. In some embodiments, signals generated by the complexes are monitored in real-time while the light (e.g., a laser pulse) is applied, allowing for adjustment of the intensity of the incident light (e.g., of the active laser power ("ALP")) to lead to the desired number of nanoscale wells containing a single reaction complex. In embodiments in which signals are generated during incorporation of labeled nucleotide analogs, the number of signal pulses observed per unit time can be counted. This represents the number of nucleotides incorporated per unit time, i.e., the base rate. Since the polymerization rate is known (or can be determined under relevant conditions as well known in the art for the particular polymerase employed), the base rate can be used to calculate the average number of active polymerase enzyme complexes per nanoscale well (A, as in the Poisson distribution). Monitoring A while continuing to apply the laser pulse (or other light) allows for nuanced control over the ALP such that the ALP (or optical power or intensity) can be increased or decreased as needed to ultimately result in the desired number of wells containing a single active complex. In some embodiments, the light used to induce photodamage also serves as excitation light for a fluorescent label, e.g., on labeled nucleotide analogs.

In some embodiments, additional tuning of the level of inactivation can be accomplished by allowing the polymerase enzyme to process the template nucleic acid (e.g., produce a complementary nascent strand) in the absence of illumination. Such "dark extension" activity will in general cause a certain fraction of the polymerase enzyme complexes to inactivate simply by virtue of time of reaction, e.g., through dissociation of the complex.

In some embodiments, the nanoscale wells contain one or more agents that decrease processivity of the polymerase enzyme as compared to the processivity in the absence of such agents. A reduction in processivity can include a reduction in the rate or efficiency at which the polymerase enzyme incorporates analogs into a nascent strand. Agents to reduce polymerase enzyme processivity can include, without limitation, noncatalytic divalent ions (e.g., strontium, cobalt, tin, calcium, nickel, europium, barium, iron, and/or zinc, optionally while reducing the concentration of catalytic metal ions such as magnesium or manganese), nonhydrolyzable nucleotide analogs, and agents to lower pH. Reducing the processivity of the polymerase enzyme can be helpful in further tuning the level of active polymerase enzyme complexes that remain in the array of nanoscale wells by providing an additional method of slowing or inactivating the complexes to result in a predetermined threshold level of nanoscale wells containing a single complex.

In some aspects, the polymerase enzyme complexes are inactivated through random termination. In such aspects, a fraction of the active polymerase enzyme complexes in an array of nanoscale wells are randomly terminated, generally by adding extension terminating reagents to the nanoscale wells. Exemplary extension terminating reagents include one or more dideoxynucleotide triphosphates (ddNTPs). Other suitable extension terminating reagents include 3'-blocked nucleotides (nucleotides or analogs without a free 3'-hydroxyl group), for example, 3'-O-azido dNTPs (e.g., 3'-O-azido-dTTP), 3'-O-amino dNTPs (e.g., 3'-O-amino-dTTP), 3'-deoxy-UTP, and 3'-O-methyl-UTP. Optionally, a single type of 3'-blocked nucleotide (e.g., a single ddNTP) is employed. In other embodiments, mixtures of two or more types of 3'-blocked nucleotides are employed (e.g., two ddNTPs (e.g., ddATP and ddTTP), three ddNTPs, or four ddNTPs, one corresponding to each of the four bases, e.g., ddATP, ddGTP, ddCTP, and ddTTP). Optionally, reversible extension terminating reagents can be used to provide further control over the level of inactivation seen among the loaded complexes. Such additional control can be useful, for example, if too many complexes are terminated, resulting in fewer wells than desired containing a single active complex; in such instances, termination can be reversed (either entirely before the termination process is repeated, or more typically in part until the desired number of wells is reached). As another example, termination can be reversed (in whole or part) even in cases where the desired number is initially attained in the termination reaction, at a later point (e.g., following a period of analysis, e.g., single molecule sequencing) to provide a fresh supply of active polymerase complex. Suitable reversible extension terminating reagents are known in the art and include, but are not limited to, 3'-O-azidomethyl dNTPs (e.g., 3'-O-azidomethyl dTTP) and 3'-O-allyl dNTPs (e.g., 3'-O-allyl dTTP). For discussion and examples of reversible terminators, see, e.g., U.S. Pat. No. 9,175,342 and Chen et al. (2013) "The history and advances of reversible terminators used in new generations of sequencing technology" Genomics Proteomics Bioinformatics 11:34-40, each of which is hereby incorporated by reference in its entirety.

In some embodiments, the inactivating through use of extension terminating agents occurs over a period of time from about 5 to about 90 minutes. For example, the inactivating can occur over a period of time from about 10-30, 15-85, 20-80, 25-75, 30-70, 35-65, 40-60, or 45-55 minutes.

For a given terminating agent such as ddNTPs, the probability of incorporation of the terminating agent is generally fixed and dependent on concentration (e.g., of the ddNTPs as well as any dNTPs or other nucleotide analogs that may be present). A suitable termination percentage in a given time period of inactivation can thus be determined to result in the desired level of inactivation of polymerase enzyme complexes (e.g., by controlling the concentration of the ddNTP(s)). For example, if a ddNTP and the corresponding incorporatable nucleotide analog are incorporated equally well by the particular polymerase enzyme that is part of the polymerase enzyme complex, then a specified percentage of the active polymerases can be terminated in a given amount of time by introducing the ddNTP at the appropriate fraction of the total nucleotides, based on the known polymerization rate of the polymerase enzyme. For example, without limitation to any particular mechanism, if a ddNTP and the corresponding dNTP are incorporated equally by the polymerase, about 50% of active polymerases will terminate in 10 minutes when the ddNTP is introduced at approximately 1/900 the concentration of the total nucleotides, assuming a polymerization rate of 1.5 b/s. The level of inactivation of the polymerase enzyme complexes can thus be tuned by providing the extension terminating agent at a concentration that results in the appropriate level of inhibition over a given amount of time. It will be evident that either or both the concentration of the extension terminating reagent and the reaction time can be controlled to produce the desired degree of inactivation.

In some embodiments, steps can be taken to ensure that inactive complexes do not produce signals through cognate sampling that would introduce noise into any subsequent sequencing reactions utilizing the active complexes. Such steps can include using a ddNTP that has a reactive moiety on it to terminate extension and inactivate the complex, as described above. That reactive moiety can then be reacted with an additional agent that is large enough to block the cognate base site. Thus, the inactivated complex will not be able to generate any noise in later sequencing reactions through cognate sampling, because the site for such sampling is unavailable. Similarly, the terminating agent can include a large moiety, e.g., on the base, that does not prohibit incorporation of the agent but that blocks the cognate base site. Examples include, but are not limited to, analogs having a bulky group on the 5-methyl group of a dT (e.g., an alkyl linker and a polyphosphate, or a linker tethered to streptavidin or another polypeptide).

As for the embodiments above, monitoring signals from the polymerase enzyme complexes can include calculating the average number of active complexes per well based on an average level of signals detected from at least a plurality of the nanoscale wells. Once the predetermined number of nanoscale wells contains a single active polymerase enzyme complex, the extension terminating reagent can be removed by washing the array of nanoscale wells. As noted, the array can be monitored continuously or intermittently until the desired number of wells is seen to be occupied by a single active complex, or one or more initial measurement can be taken and used to calculate an extension terminating reagent concentration and/or reaction time required to achieve the desired number of occupied wells and the wash can be performed at this calculated time (with or without additional measurements of the number of occupied wells as confirmation).

In another aspect, the polymerase includes a protease cleavage site. Inactivation of the polymerase complex is achieved by adding the relevant protease, e.g., at a concentration and for a time to result in a desired number of single active complexes remaining.

In some embodiments, the methods described herein can be conducted until a predetermined number of the nanoscale wells in the array contain an active polymerase enzyme complex (whether a single complex or more than one complex). For example, the predetermined number of nanoscale wells in the array occupied by a polymerase enzyme complex can be at least about 10%, at least about 20%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the nanoscale wells in the array. In some embodiments, the predetermined number of nanoscale wells occupied by a polymerase enzyme complex is about 10-100% of the nanoscale wells in the array, e.g., about 30-95%, about 35-90%, about 40-80%, about 45-85%, about 50-75%, about 55-70%, or about 60-80% of the nanoscale wells in the array. In some embodiments, at least a majority of the predetermined number of nanoscale wells are occupied by a single polymerase enzyme complex.

As will be appreciated and in accordance with any of the above methods for inactivating loaded polymerase enzyme complexes, including methods involving inducing photodamage or random termination, the methods can be conducted until a predetermined number of the nanoscale wells in the array contain a single active polymerase enzyme complex. The predetermined number of nanoscale wells occupied by a single active polymerase enzyme complex can be any number that is of use for downstream applications, such as sequencing reactions. In certain embodiments, the predetermined number of nanoscale wells is at least about 10%, at least about 20%, at least about 25%, at least about 30%, or at least about 35% of the nanoscale wells in the array. In some embodiments, the predetermined number of nanoscale wells occupied by a single polymerase enzyme complex is about 10-40% of the nanoscale wells in the array, e.g., about 20-35% of the nanoscale wells in the array.

In some embodiments, the methods described herein for inactivating loaded polymerase enzyme complexes are conducted until the average number of active polymerase complexes per well is about 0.7, about 0.8, about 0.9, about 1, about 1.1, about 1.2, about 1.3, about 1.4, about 1.5, about 1.6, about 1.7, about 1.8, about 1.9, or about 2 or more. In some embodiments, the methods described herein are conducted until the average number of active polymerase complexes per well is about 0.8-2, e.g., about 1-1.8 or about 1.2-1.6.

As will be appreciated and in accordance with any of the above, including methods involving inducing photodamage or random termination, once the predetermined number of nanoscale wells is occupied by a single active polymerase enzyme complex, the array of nanoscale wells can be prepared for conducting reactions for analyzing the polymerase enzyme complexes. In certain embodiments, the polymerase enzyme complexes comprise a polymerase enzyme complexed to a template nucleic acid, and the analysis of the polymerase enzyme complexes involves sequencing reactions to determine the nucleotide sequence of the template nucleic acid. Such sequencing reactions can include any reactions known in the art and described in further detail herein. In exemplary embodiments, the sequencing reactions include the steps of (i) providing one or more nucleotides or nucleotides analogs; (ii) performing a polymerization reaction in which the polymerase enzyme replicates at least a portion of the template nucleic acid in a template-dependent manner in which one or more of the nucleotides or nucleotide analogs are incorporated into the resulting nucleic acid; and (iii) identifying a time sequence of incorporation of the one or more nucleotide or nucleotide analogs into the resulting nucleic acid.

IV. Tuning Single Molecule Loading by Modulating Polymerase Complex Inhibition In one aspect, the present disclosure provides methods for establishing active polymerase enzyme complexes (e.g., single active polymerase enzyme complexes) in a predetermined number of nanoscale wells by modulating the activation state of the polymerase enzyme in the complex. In such aspects, the polymerase enzyme complex contains a polymerase enzyme complexed to a template nucleic acid (and optionally a primer hybridized to the template nucleic acid), and the polymerase enzyme is maintained in an inhibited state during the loading process (or in some embodiments is inhibited after loading). That inhibited state prevents the complex from being able to generate signals. Once the polymerase enzyme complex is within a nanoscale well, the inhibition is released and the polymerase enzyme complex is able to start generating signals. The signals are monitored and the release of inhibition is continued across the array until the level of signaling indicates that a predetermined number of nanoscale wells contain a single active polymerase enzyme complex, e.g., in the observation volume.

Inhibition of the polymerase enzyme can be accomplished in essentially any convenient manner. Various ways of inhibiting polymerases are known in the art and can be adapted to the practice of the present invention. For example, a polymerase inhibitor (typically, a reversible inhibitor such as a competitive, uncompetitive, or noncompetitive inhibitor, a substrate or product mimic, or the like) can be employed. Suitable inhibitory moieties include, e.g., a nonhydrolyzable analog, a polyphosphate (e.g., including two, three, four, five, or more phosphate groups), and an antibody (e.g., that blocks access to the active site when bound to the polymerase). In some embodiments, an inhibitor is connected to the polymerase through a cleavable tether. For example, the polymerase can be bound (covalently or noncovalently) to a first moiety to which an inhibitor is connected through a cleavable tether. Inhibition can then be relieved by exposing the inhibited polymerase to the corresponding cleavage agent. As an example, a tether containing a protease site can be cleaved by exposure to the corresponding protease. Suitable proteases, as well as their recognition sites and digestion conditions, are well known in the art and include, but are not limited to, thrombin, Tobacco Etch Virus (TEV) protease, enterokinase, 3C rhinovirus protease, and trypsin. As another example, a tether containing RNA can be cleaved by exposure to RNase. In yet another example, a DNA tether contains a restriction site, and the cleavage agent is the corresponding restriction enzyme. In some embodiments, the tether is photocleavable. In other embodiments, inhibition is relieved by degradation or removal of the inhibitor rather than by cleavage of a tether. For example, a polyphosphate group can be cleaved by a phosphatase (e.g., an alkaline phosphatase such as calf intestinal phosphatase (CIP)), or a protease-sensitive antibody can be digested with protease. In other embodiments, inhibition is relieved by modification of the inhibitor. For example, a primer whose 3' end is blocked with a reversible terminator can be modified to produce a free and accessible 3' hydroxyl group on the primer (e.g., by exposure to light to remove a photolabile group or by exposure to a suitable chemical removal agent, e.g., TCEP).

Figure 7:
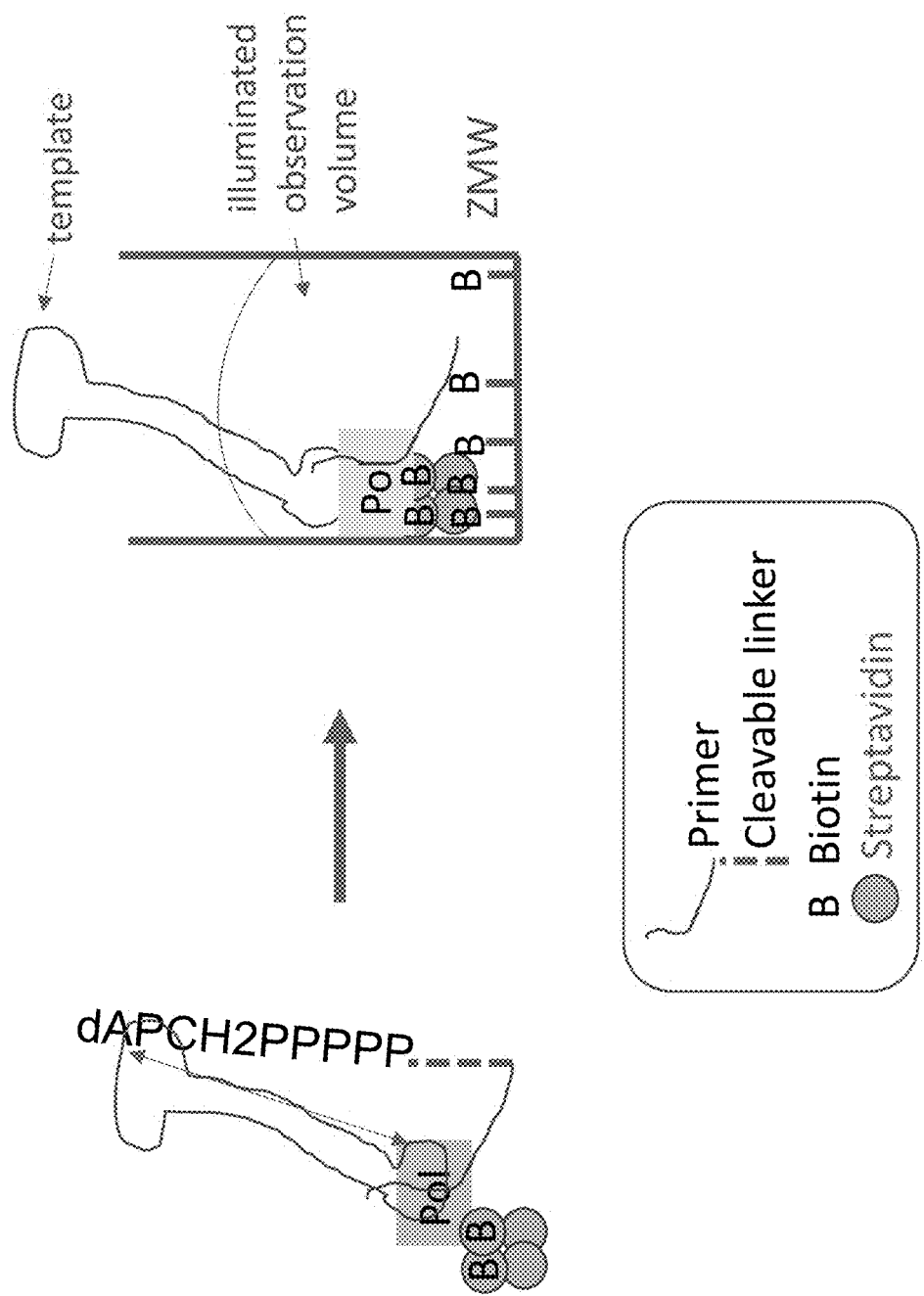
FIG. 7 schematically illustrates relief of polymerase inhibition concomitant with immobilization in a nanoscale well.

In one exemplary class of embodiments, the polymerase complex includes a primer hybridized to the template nucleic acid. The primer is linked to a nonhydrolyzable nucleotide analog by a cleavable tether, e.g., at the 5' end of the primer as schematically illustrated in FIG. 7. Optionally, the nonhydrolyzable analog is complementary to the next available base on the template nucleic acid. Binding of the nonhydrolyzable analog to the polymerase complex prevents extension. Cleavage of the tether releases the nonhydrolyzable analog from the complex and restores activity. Exemplary cleavable tethers and cleavage agents have been described above.

Figure 8A:
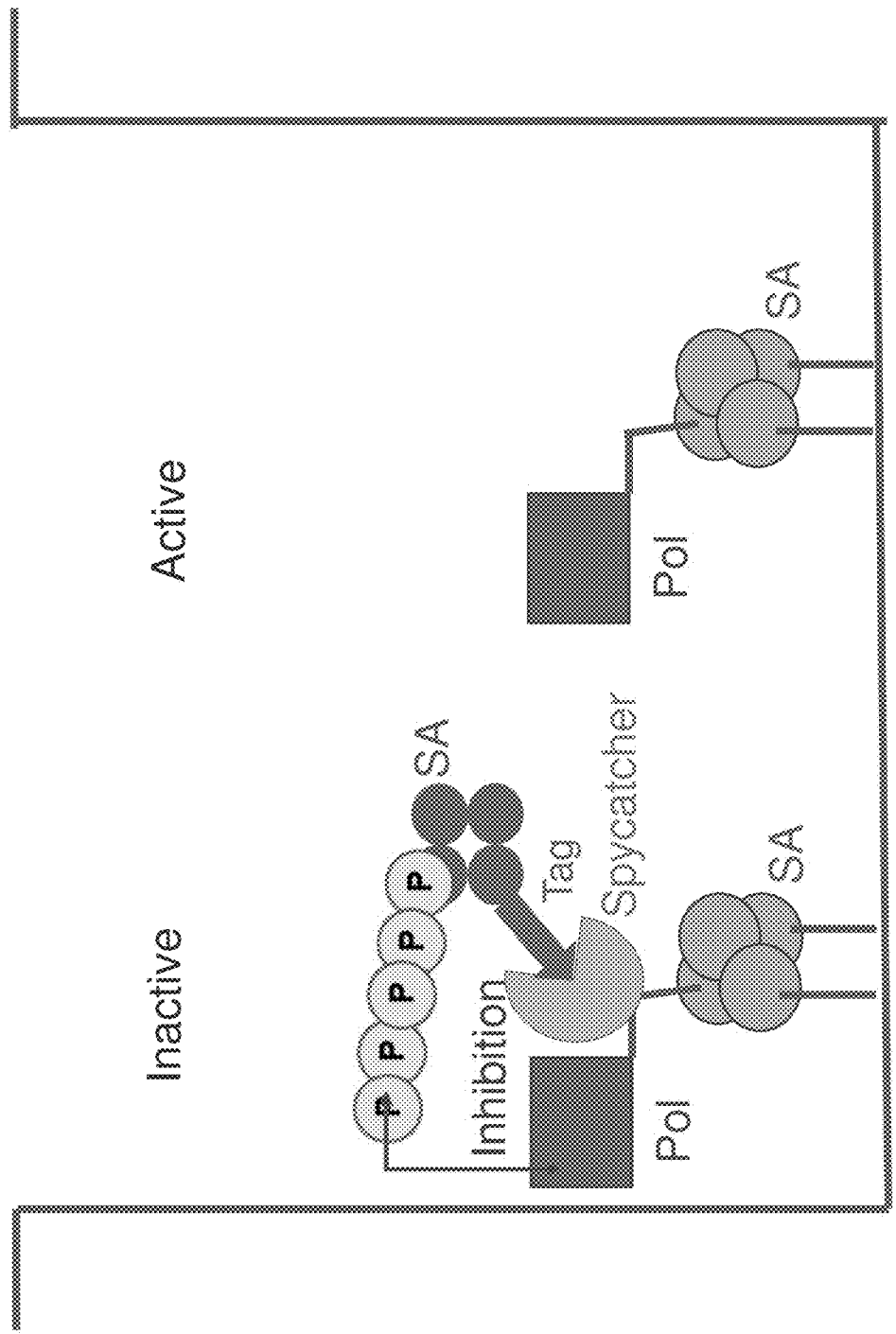
FIG. 8A schematically illustrates loading of a mixture of inhibited and active polymerase enzyme complexes.

In another exemplary class of embodiments, the polymerase enzyme is fused to a SpyCatcher domain as schematically illustrated in the left side of FIG. 8A. A streptavidin tetramer fused to a SpyTag is connected to the SpyCatcher-fused polymerase through an isopeptide bond. (SnoopCatcher/SnoopTag and similar systems can also be employed. For discussion of the SpyTag/SpyCatcher and SnoopTag/SnoopCatcher systems, see, e.g., Zakeri et al. (2012) "Peptide tag forming a rapid covalent bond to a protein, through engineering a bacterial adhesin" Proc Natl Acad Sci USA 109(12):E690-7; Fairhead et al. (2014) J. Am. Chem. Soc. 136: 12355-12363; U.S. Pat. No. 9,547,003; Veggiani et al. (2016) "Programmable polyproteams built using twin peptide superglues" Proc Natl Acad Sci USA 113(5):1202-7; and Brune et al. (2017) "Dual Plug-and-Display Synthetic Assembly Using Orthogonal Reactive Proteins for Twin Antigen Immunization" Bioconjugate Chem. 28:1544-1551.) A polyphosphate group (e.g., a pentaphosphate) is also linked to the streptavidin, e.g., through a bis-biotin moiety on the terminal phosphate. Binding of the polyphosphate to the polymerase inhibits the polymerase. Inhibition can be relieved by application of CIP. In a related example, the SpyCatcher domain is fused to the polymerase through a linker containing a protease site, and inhibition is relieved by application of the protease; see, e.g., FIG. 16C.

In another exemplary class of embodiments, the polymerase enzyme complex includes a primer hybridized to the template nucleic acid. The 3' end of the primer is blocked by a reversible terminator. Suitable reversible terminators are well known in the art and include, but are not limited to, 3'-O-blocked reversible terminators in which a blocking group is attached to the 3' oxygen atom of a nucleotide (e.g., 3'-ONH$_2$, 3'-O-azidomethyl, and 3'-O-allyl dNTPs) and 3'-unblocked reversible terminators in which a blocking group is attached, e.g., to the base. For either type of terminator, removal of the blocking group (also referred to as a reversible terminating group herein) makes the 3' hydroxyl group free and accessible for extension of the primer. For discussion and examples of reversible terminators, see, e.g., U.S. Pat. No. 9,175,342 and Chen et al. (2013) Genomics Proteomics Bioinformatics 11:34-40, previously incorporated by reference in their entirety. The primer can be synthesized including the reversible terminator, or a reversible terminator can be provided in solution and added to a primer by extension activity of the polymerase. Presence of the reversibly terminated primer in the polymerase enzyme complex prevents any further extension by the polymerase. Removal of the blocking group (e.g., by chemical treatment or exposure to light as appropriate for the particular terminator employed and as known in the art) restores activity.

In some embodiments, the release of inhibition of the polymerase enzyme is concomitant with immobilization of the complex within the nanoscale well, e.g., within the observation volume of the well. In one class of embodiments, the polymerase enzyme complex comprises an inhibitory moiety linked to the polymerase complex by a cleavable tether.

For example, as schematically illustrated in FIG. 7, the polymerase complex can include a primer linked to a nonhydrolyzable nucleotide analog through a photocleavable tether. The primer is hybridized to the template. The polymerase enzyme complex in solution is inactive due to binding of the nonhydrolyzable analog. Upon immobilization of the complex, e.g., through binding of a streptavidin tetramer to which the bis-biotinylated polymerase is bound to the biotinylated bottom of a ZMW, the complex is exposed to light that illuminates the observation volume of the ZMW. The illuminated volume is indicated by the curved line in FIG. 7. Cleavage of the photolabile linker releases the nonhydrolyzable analog and restores polymerase activity. The illumination of the wells can occur throughout the loading process or at a fixed time point after the polymerase enzyme complexes have been delivered to the arrays. Illumination time can be controlled to achieve the desired level of loading (e.g., the desired number of wells containing a single active complex). Photocleavable linkers are known in the art and include 2-nitrobenzyl linkers as well as others, including for example those described in Rodebaugh, et al., Tetrahedron Lett. 1997, 38, 7653-7656; Glatthar et al., 2000, Org. Lett. 2(15):2315-2317; Yan et al., 2004, Bioconjugate Chem., 15(5): 1030-1036; U.S. Pat. Nos. 7,476,504; 8,906,831; 8,975,216; each of which is herein incorporated by reference in its entirety for all purposes and in particular for all teachings related to the use of photocleavable groups and linkers. Immobilization can optionally be halted at any point, e.g., by use of a linker that also includes a stretch of RNA (or another cleavable linker); when the desired level of loading is achieved, application of RNase (or another cleavage agent) releases inhibition of polymerase enzyme complexes that are at the surface of the array and not yet loaded into the nanoscale wells, allowing those polymerase enzymes to produce nascent strands and thus generate structures that load poorly into nanoscale wells.

As another example, the polymerase complex can include a primer linked to a nonhydrolyzable nucleotide analog through an RNA tether. An RNase is immobilized on the bottom of the ZMW, e.g., prior to loading of the polymerase complex. Immobilization of the polymerase complex to the ZMW bottom thus exposes the RNA tether to the RNase, resulting in degradation of the tether, release of the nonhydrolyzable analog into solution, and restoration of polymerase activity. Optionally, the ZMW bottom is biotinylated, and the RNase and polymerase complex are independently immobilized through binding to streptavidins. It will be evident that other cleavable tethers and cleavage agents can be similarly employed, as can degradable inhibitors and their corresponding removal agents (e.g., a polyphosphate and a phosphatase).

In some embodiments, the inhibition of the polymerase enzyme complex is released after immobilization of the complex. The release of inhibition can be conducted in a controlled manner, allowing for the release of inhibition to continue until a desired level of occupancy is reached. For such controlled release methods, the inhibited complexes are generally loaded onto the array of nanoscale wells at a concentration that results in overloading of the nanoscale wells, e.g., by delivering two or more polymerase complexes to at least a plurality of the wells (e.g., to a majority of the wells). Rather than releasing inhibition of a number of complexes at one or more distinct time points, release of inhibition can be continuous. For example, a low concentration of cleavage or removal agent can be provided, e.g., added to the loading solution, to occasionally provide newly disinhibited complexes as analysis is being performed.

In one class of embodiments, an inhibitor is connected to the polymerase enzyme through a cleavable tether; for example, the polymerase enzyme can be bound (covalently or noncovalently) to a first moiety to which the inhibitor is connected through the cleavable tether. Inhibition of the immobilized inhibited polymerase can be relieved by addition of the corresponding cleavage agent to the nanoscale wells (e.g., to a solution covering the surface of the array). Contact time of the cleavage agent with the complexes can be controlled to achieve the desired degree of disinhibition. Suitable inhibitors, cleavable linkers, and cleavage agents have been described above. For example, the polymerase complex can include a primer linked to a nonhydrolyzable nucleotide analog through a cleavable tether (e.g., a tether containing a protease site, RNA, or a restriction site). The primer is hybridized to the template. The polymerase enzyme complex in solution is inactive due to binding of the nonhydrolyzable analog. After immobilization of the complex, e.g., through binding of a streptavidin tetramer to which the bis-biotinylated polymerase is bound to the biotinylated bottom of a ZMW, the complex is exposed to the cleavage agent (e.g., a protease, RNase, or restriction enzyme). In another class of embodiments, inhibition is relieved by degradation or removal of the inhibitor rather than by cleavage of a tether. For example, the polymerase enzyme can be bound to a polyphosphate group that can be cleaved by a phosphatase (e.g., an alkaline phosphatase) or to a protease-sensitive antibody that can be digested with protease. In another class of embodiments, inhibition is relieved by removal of a reversible terminating group from a reversibly blocked primer, for example, by chemical modification of the primer. Once the desired number of nanoscale wells contain a single active polymerase enzyme complex, the cleavage, removal, or modifying agent can be inactivated or removed (e.g., by washing the array).

In any of the concomitant release, controlled release, or continuous release methods, the level of occupancy can be monitored by detecting signals from the disinhibited polymerase enzyme complexes. Such monitoring can be conducted continuously during the loading and releasing process, or it may take place at regular or irregular or random intervals of time to determine if a predetermined/threshold level of occupancy has been reached. Once the predetermined level of occupancy is reached, the disinhibition process can be halted and any downstream reactions conducted with the loaded complexes. For example, once the predetermined number of nanoscale wells occupied either by a single active polymerase or by at least one active polymerase is reached, the array of nanoscale wells can be prepared for conducting reactions for analyzing the polymerase enzyme complexes. In certain embodiments, the analysis of the polymerase enzyme complexes involves sequencing reactions in accordance with methods known in the art and described in further detail herein.

Optionally, modulating polymerase complex inhibition can be accomplished in the presence of photodamage mitigating agents, including those known in the art and described in further detail herein. In exemplary embodiments, such photodamage mitigating agents can include reducing agents, anti-fade agents, oxygen scavenging agents, and/or the like, thus preventing downstream damage to enzymes within the system during the detection of the level of occupancy of the nanoscale wells as well as any downstream applications such as sequencing reactions.

In some embodiments, the methods described herein can be conducted until a predetermined number of the nanoscale wells in the array contain an active polymerase enzyme complex (whether a single complex or more than one complex). For example, the predetermined number of nanoscale wells in the array occupied by a polymerase enzyme complex can be at least about 10%, at least about 20%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the nanoscale wells in the array. In some embodiments, the predetermined number of nanoscale wells occupied by a polymerase enzyme complex is about 10-100% of the nanoscale wells in the array, e.g., about 30-95%, about 35-90%, about 40-80%, about 45-85%, about 50-75%, about 55-70%, or about 60-80% of the nanoscale wells in the array. In some embodiments, at least a majority of the predetermined number of nanoscale wells are occupied by a single polymerase enzyme complex.

As will be appreciated, the methods can be conducted until a predetermined number of the nanoscale wells in the array contain a single active polymerase enzyme complex. The predetermined number of nanoscale wells occupied by a single active polymerase enzyme complex can be any number that is of use for downstream applications, such as sequencing reactions. In certain embodiments, the predetermined number of nanoscale wells is at least about 10%, at least about 20%, at least about 25%, at least about 30%, or at least about 35% of the nanoscale wells in the array. In some embodiments, the predetermined number of nanoscale wells occupied by a single polymerase enzyme complex is about 10-40% of the nanoscale wells in the array, e.g., about 20-35% of the nanoscale wells in the array.

In some embodiments, the methods are conducted until the average number of active polymerase complexes per well is about 0.7, about 0.8, about 0.9, about 1, about 1.1, about 1.2, about 1.3, about 1.4, about 1.5, about 1.6, about 1.7, about 1.8, about 1.9, or about 2 or more. In some embodiments, the methods are conducted until the average number of active polymerase complexes per well is about 0.8-2, e.g., about 1-1.8 or about 1.2-1.6.

As discussed herein, the number of nanoscale wells occupied by an active complex can be monitored by monitoring signals generated by the polymerase enzyme complexes once the inhibition of the polymerase enzyme is released. In certain embodiments, the nanoscale wells contain labeled nucleotide analogs, and the signals generated by the disinhibited polymerase enzyme complexes represent interactions between the complexes and the labeled nucleotide analogs. In exemplary embodiments, as described above, the labeled nucleotide analog is added to a nascent strand complementary to the complexed template nucleic acid, and signal is detected as the labeled analog is retained in the complex during incorporation. In other embodiments, signals are a result of cognate sampling, also as described above. While active polymerase complexes can generate signals, e.g., through incorporation or cognate sampling, inhibited complexes are unable to generate signals.

As detailed above, modulating the activation state of polymerase enzymes can be beneficial in achieving the desired degree of single molecule loading. Modulating the activation state of polymerases, e.g., through controlled relief of enzyme inhibition, is also beneficial in other situations. For example, this technique is generally useful in any application in which initiation of enzyme activity at one or more time points during or after loading is desired.

Accordingly, in one aspect, the present disclosure provides methods for providing active polymerase enzyme complexes in nanoscale wells. In the methods, an array of nanoscale wells is provided, and polymerase enzyme complexes are delivered to a plurality of the nanoscale wells. The polymerase enzyme complexes comprise a polymerase enzyme complexed to a template nucleic acid. The polymerase enzyme complexes are immobilized within the nanoscale wells (e.g., in the observation volume of the wells). In some embodiments, the polymerase enzyme is inhibited during the delivering step. In other embodiments, the polymerase enzyme is inhibited following its delivery to (and optionally immobilization in) the nanoscale well. After inhibited complexes are established in the wells (whether through delivery of inhibited complexes or inhibition of some or all of the complexes after delivery of the complexes), inhibition of at least a plurality of polymerase enzymes that are immobilized within the nanoscale wells is released, thereby establishing active polymerase enzyme complexes within the nanoscale wells. Inhibition can be achieved and released using any suitable technique, for example, an inhibitor with a cleavable tether, a reversible terminating group, or the like as detailed herein.

In some embodiments, the methods are employed to delay initiation of polymerase activity until sometime after immobilization of the complex. In such embodiments, after the polymerase complexes have been immobilized and inhibition of the polymerases is been released, the active polymerase enzyme complexes can be analyzed (for example, by performing sequencing reactions to determine the nucleotide sequence of the template nucleic acid).

Delaying polymerase activity is useful for a variety of applications. As one example, "hot start" nucleic acid sequencing can be performed by immobilizing inhibited polymerase complexes in the nanoscale wells, preparing the wells for sequencing reactions, and then releasing the inhibition to start the reactions.

As another example, delayed activation can provide an on-demand pool of reagents during analysis. In one example, inhibited polymerase complexes are immobilized in nanoscale wells. Inhibition of a portion of the complexes is relieved. These active complexes are analyzed (e.g., in nucleic acid sequencing reactions) while the remaining portion of the complexes remain inhibited. At a later time, for example, after a number of the initially active complexes have suffered photodamage, dissociation, and/or template damage and are no longer useful for analysis (or after analysis of these initially active complexes has been completed), the release step can be repeated to provide a fresh supply of active, undamaged complexes for analysis.

In a related example, a mixture of uninhibited, active polymerase complexes and inhibited polymerase enzyme complexes are delivered to and immobilized in nanoscale wells. The uninhibited complexes are analyzed. At a later time (e.g., after analysis of the uninhibited complexes is complete or after the uninhibited complexes have suffered photodamage or otherwise become inactive), inhibition of the inhibited complexes is released, providing a fresh supply of active complexes for analysis.

Figure 8B:
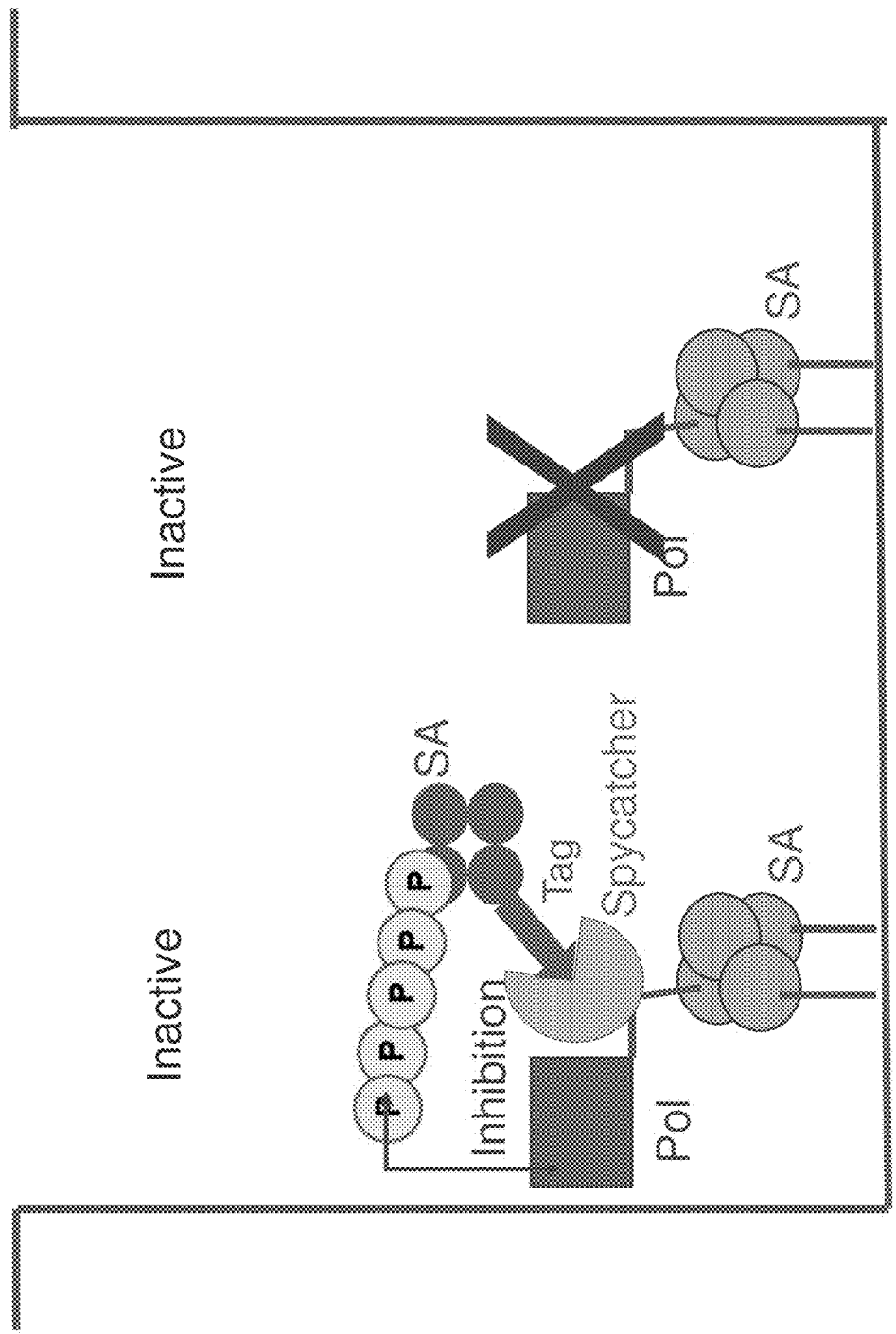
FIG. 8B schematically illustrates subsequent inactivation of the active complex, e.g., by photodamage.
Figure 8C:
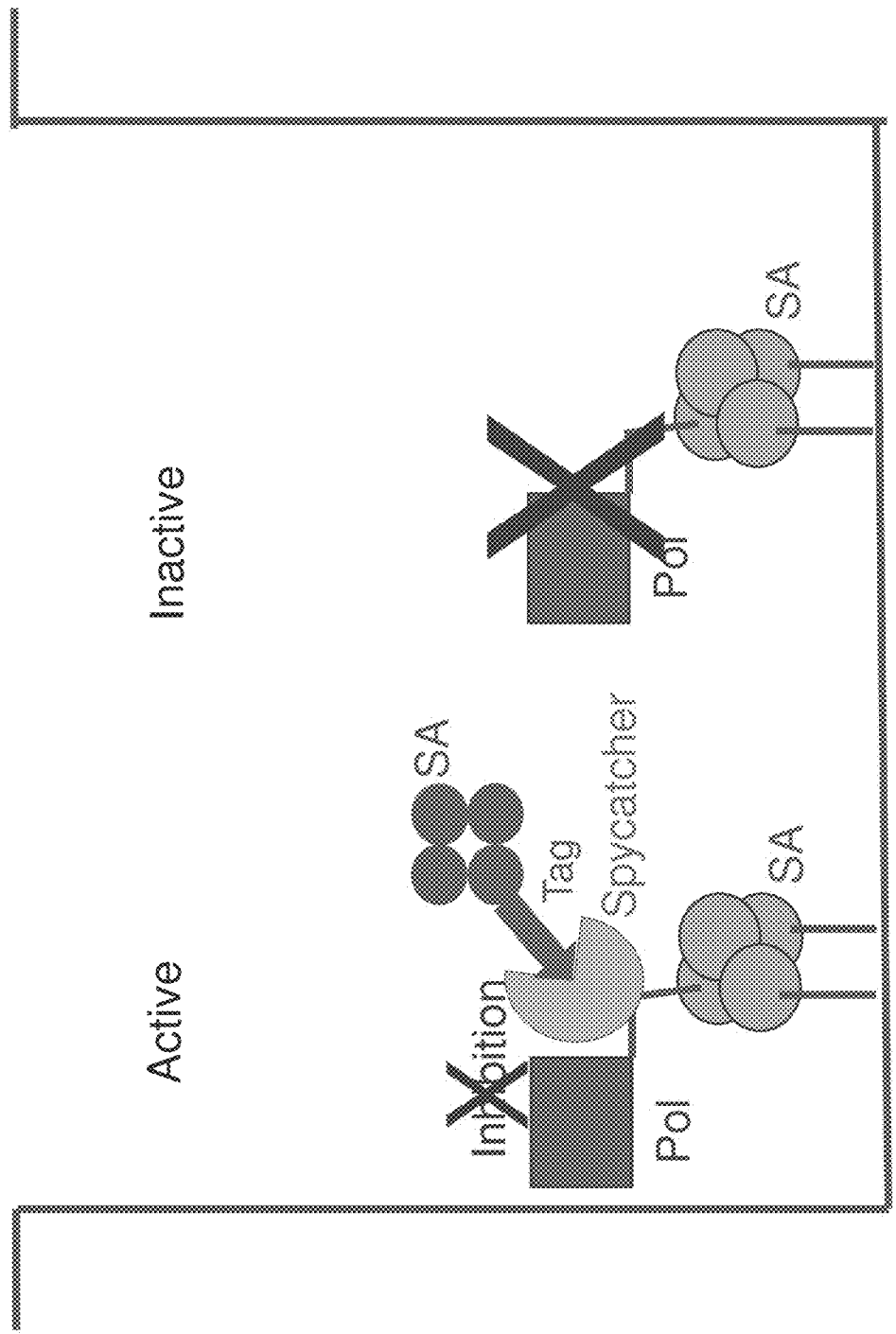
FIG. 8C schematically illustrates relief of polymerase inhibition to activate the inhibited polymerase.

An exemplary embodiment is illustrated in FIGS. 8A-8C. As shown in FIG. 8A, a mixture of active polymerase complexes and inhibited polymerase complexes is immobilized in a nanoscale well. As shown on the left side of FIG. 8A, a polymerase-SpyCatcher fusion is connected to a streptavidin-SpyTag construct (in which one of the four streptavidin monomers bears a SpyTag) through an isopeptide bond formed by the SpyCatcher/SpyTag pair. A pentaphosphate group that is also linked to the streptavidin binds to and inhibits the polymerase. The polymerase is biotinylated (e.g., bis-biotinylated) and immobilized to the biotinylated bottom of the nanoscale well through another streptavidin tetramer. As shown on the right side of FIG. 8A, another polymerase molecule is biotinylated and immobilized on the bottom of the nanoscale well through yet another streptavidin tetramer; this polymerase is active. Nucleic acid templates and optional primers bound to the polymerases are omitted from the illustration for clarity. The active polymerase complex can be analyzed, e.g., in a single molecule sequencing reaction. The active polymerase complex can suffer photodamage or the like during this analysis, rendering it inactive as shown in FIG. 8B. Inhibition of the complex on the left can be relieved by removal of the polyphosphate group as shown in FIG. 8C, for example, by addition of CIP. The newly active polymerase complex can then be analyzed, e.g., by single molecule sequencing.

It will be evident that inhibition can be achieved using any of the techniques described herein or known in the art, including, but not limited to, by attachment of a polyphosphate group as in the previous example, provision of a primer whose 3' end is blocked by a reversible terminator, reversible chemical modification of the polymerase, inhibition of the polymerase by a removable binding partner (e.g., a reversibly bound inhibitor similar to the aptamer-based inhibitor employed with Taq DNA polymerase in hot start PCR), inhibition by a moiety linked to the polymerase through a cleavable tether, or the like.

Although in the preceding example the active and inhibited complexes are provided and immobilized separately, in other examples, an active complex and an inhibited complex can be physically associated to ensure immobilization of the complexes in a defined ratio. For example, an active and an inhibited complex can be joined by a linker. In some embodiments, the linker is subject to cleavage by a cleavage agent (e.g., a protease, RNase, etc. as detailed herein). In such embodiments, the methods can include addition of the cleavage agent, e.g., after immobilization and prior to analysis where the two complexes are separately attached to the bottom of the nanoscale well, or after analysis of the active complex and prior to analysis of the inhibited complex where the active complex is attached to the well through the inhibited complex (see, e.g., FIGS. 14C and 15A-B).

It will be evident that release of inhibition can occur at one or more fixed time points during analysis (for example, analysis can be performed for a certain amount of time before a cleavage or removal agent is added to produce a fresh supply of active complexes), or release of inhibition can be continuous during analysis (for example, analysis can be performed in the presence of a low concentration of the cleavage or removal agent, such that freshly activated polymerases become available throughout the analysis, e.g., at a rate calculated to counteract or offset the rate at which polymerase complexes become inactivated due to dissociation, photodamage, and/or other damage).

In some embodiments in which a mixture of inhibited and uninhibited polymerase enzymes are provided, different polymerase molecules are bound to different template nucleic acid molecules. For example, polymerase enzymes can be bound to a mixture of different templates to be sequenced. Some of the resulting complexes can be inhibited (e.g., before or after delivery of the complexes to nanoscale wells). After the mixture of active and inhibited complexes is immobilized in the observation volume of nanoscale wells, the active complexes can be analyzed, inhibition can be released, and the previously inhibited complexes can be analyzed, as detailed above.

Figure 14A:
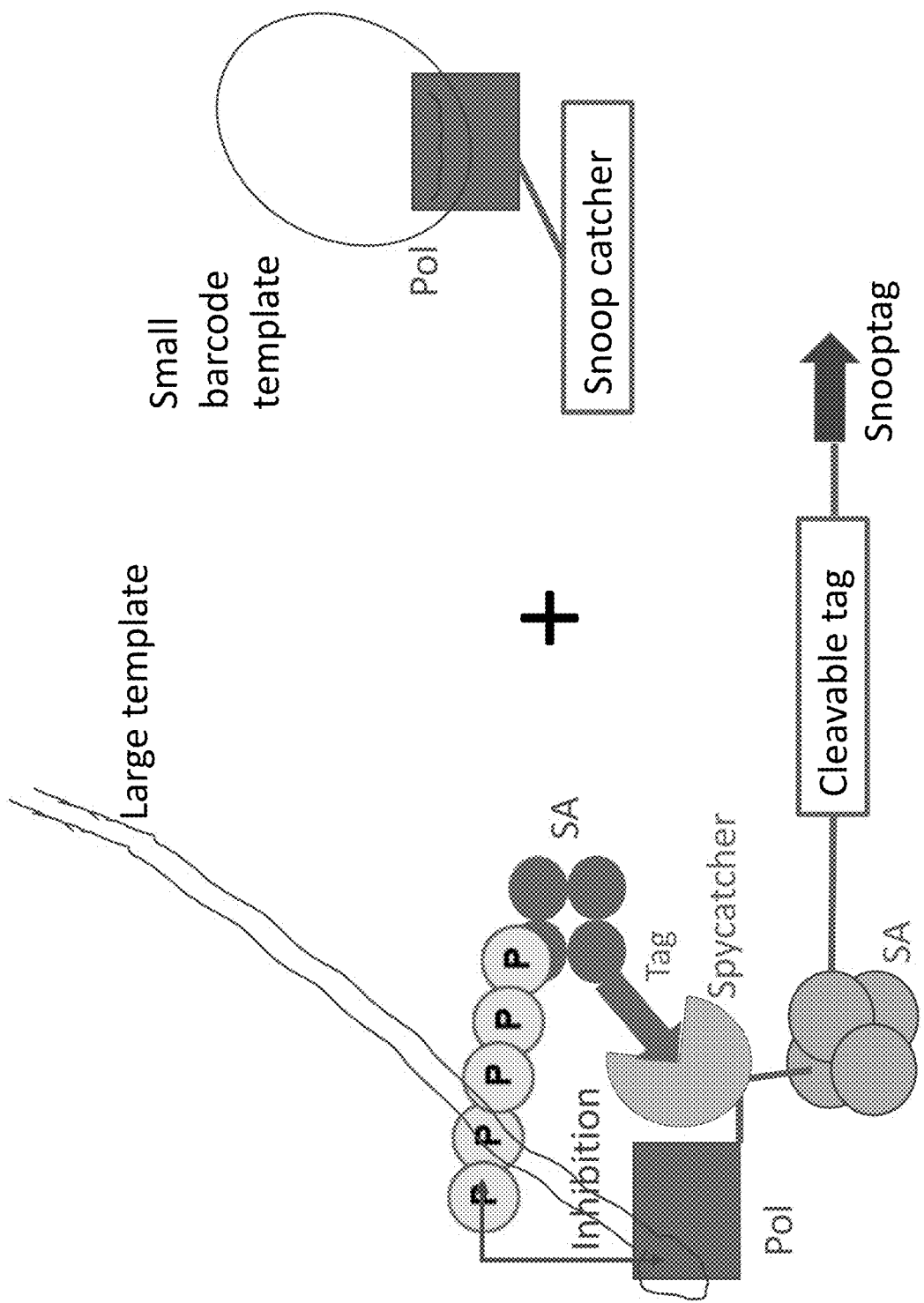
FIG. 14A schematically illustrates an active polymerase/barcode complex and an inhibited polymerase/template complex.
Figure 14B:
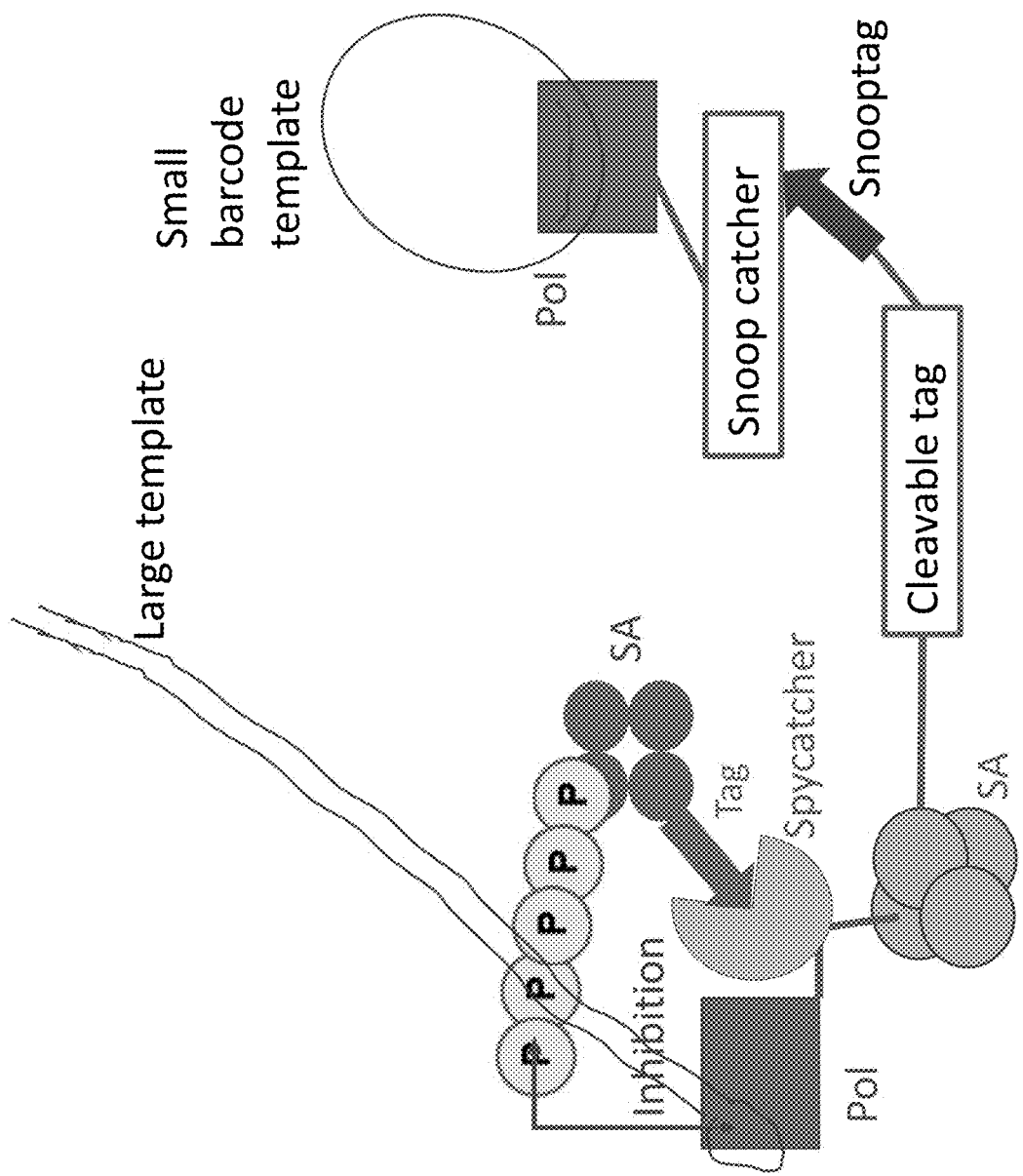
FIG. 14B schematically illustrates stable association of the two complexes.

As another example, a mixture of inhibited and uninhibited polymerases can be employed for barcoding. An exemplary embodiment is illustrated in FIGS. 14A-D. In this example, one complex comprising a template to be sequenced is associated with another complex comprising a barcode nucleic acid, e.g., a barcode sequence that conveys information about the template (for example, the source of the template, e.g., an organism, patient, population, location, time of sample collection, sample treatment type, and/or the like). As shown on the left side of FIG. 14A, a polymerase-SpyCatcher fusion is connected to a streptavidin-SpyTag construct (in which one of the four streptavidin monomers is fused to a SpyTag) through an isopeptide bond formed by the SpyCatcher/SpyTag pair. A pentaphosphate group that is also linked to the streptavidin binds to and inhibits the polymerase. This first polymerase is bound to a template nucleic acid and optionally a primer. The polymerase is biotinylated (e.g., bis-biotinylated) and associated with another streptavidin tetramer, which carries a SnoopTag fused to one of its subunits through a cleavable linker (e.g., a protease susceptible linker). As shown in the right side of FIG. 14A, a second polymerase molecule is fused with SnoopCatcher. This polymerase is bound to a barcode nucleic acid, preferably a small circular DNA (e.g., a minicircle DNA), and optionally also a primer. The barcode nucleic acid typically has a predetermined sequence, such that a particular barcode sequence can provide information about an associated template sequence (e.g., to uniquely identify the template's sample source in a multiplex format, etc.). The barcode nucleic acid can have essentially any convenient size. In some embodiments, the barcode nucleic acid is about 10 to about 500 nucleotides long, e.g., about 20 to about 200 nucleotides, about 30 to about 150 nucleotides, or about 40 to about 100 nucleotides. In some embodiments, the barcode nucleic acid is a minicircle of about 500 or fewer bp, e.g., less than about 300 bp, less than about 200 bp, or less than about 100 bp, e.g., about 70-75 bp. The polymerase/template complex is incubated with the polymerase/barcode complex. Typically, this incubation is performed in bulk; for example, polymerase complexes including large templates from a genomic library can be incubated with polymerase complexes including one type of barcode, while complexes formed from other libraries are individually incubated in parallel with polymerase complexes including other unique barcodes, prior to mixing the resulting barcoded complexes. The SnoopTag/SnoopCatcher reaction occurs, resulting in an isopeptide bond between the SnoopTag/SnoopCatcher pair. The barcodes are now stably associated with templates, as shown in FIG. 14B.

Figure 14C:
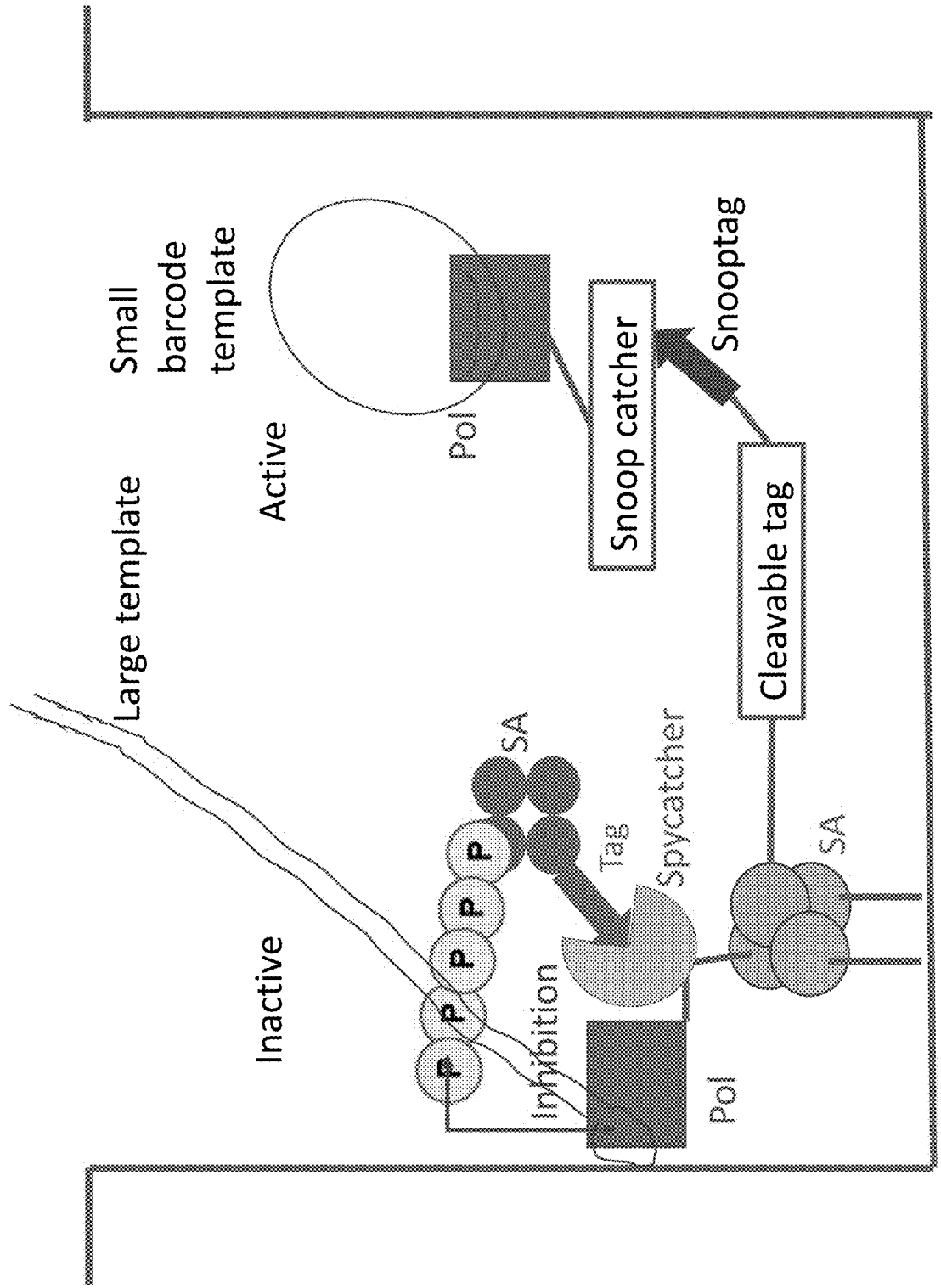
FIG. 14C schematically illustrates immobilization of the large complex including both the active polymerase/barcode complex and the inhibited polymerase/template complex on the bottom of a nanoscale well.

The entire barcoded complex is immobilized to the biotinylated bottom of a nanoscale well through the second streptavidin tetramer that is associated with the first polymerase, as shown in FIG. 14C. The active polymerase complex is analyzed, e.g., in a single molecule sequencing reaction. In embodiments in which the barcode nucleic acid is circular, multiple reads of the barcode can be obtained if desired to confirm the identity of the barcode. A suitable cleavage agent (e.g., a protease whose site is located in the cleavable linker) is added. Cleavage releases the second polymerase/barcode nucleic acid complex from the polymerase/template complex, and it can be removed, e.g., by diffusion or washing. Inhibition of the remaining complex is relieved by removal of the polyphosphate group as shown in FIG. 14D, for example, by addition of CIP. The now active polymerase/template complex is analyzed, e.g., by single molecule sequencing to determine the sequence of the large template nucleic acid.

In the previous example, release of the barcode/polymerase complex from the polymerase/template complex and relief of inhibition are accomplished by separate reagents. It is worth noting, however, that release of the barcode/second polymerase complex from the first polymerase/template complex and relief of inhibition of the first polymerase can occur simultaneously or sequentially in any desired order. As one example, in the system illustrated in FIGS. 14A-D, a protease can be supplied to release the barcode/second polymerase, and then CIP can be applied to relieve inhibition of the first polymerase. As another example, CIP and a protease having compatible reaction conditions can be supplied to accomplish the release and relief steps simultaneously. In yet another example, the pentaphosphate group (or other inhibitory moiety) is associated with the polymerase through a linker cleaved by the same agent that removes the barcode/second polymerase from the first polymerase/template. In an illustrative embodiment, a cleavable linker is placed between the polyphosphate group and the first polymerase (see, e.g., FIG. 16C). Exposure to the cleavage agent releases the polyphosphate group and thus releases inhibition of the polymerase. This cleavable linker and the cleavable linker between the streptavidin monomer and the SnoopTag in FIGS. 14A-C can include the same protease site (or other cleavage site), such that removal of the barcode complex and the polyphosphate are accomplished simultaneously using the same protease (or other cleavage agent).

Figure 15A:
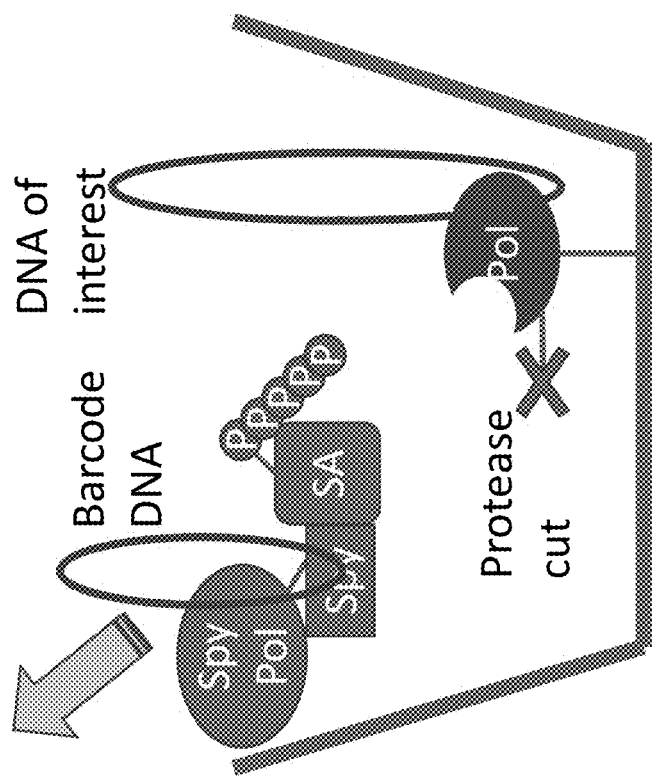
FIG. 15A schematically illustrates an active polymerase/barcode complex and an inhibited polymerase/template complex.
Figure 15B:
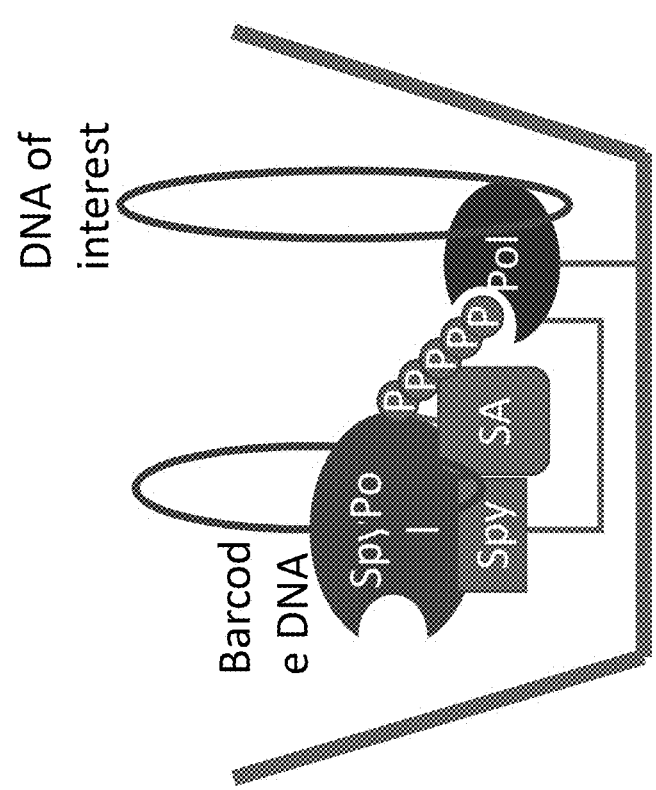
FIG. 15B schematically illustrates removal of the polymerase/barcode complex and relief of polymerase inhibition to activate the inhibited polymerase.

Yet another example is illustrated in FIGS. 15A-B. In this example, as shown in FIG. 15A, a first polymerase is bound to a nucleic acid of interest (e.g., a large DNA template). The first polymerase can be immobilized (e.g., bis-biotinylated and immobilized via binding to streptavidin that is in turn bound to a biotinylated surface). The first polymerase is connected to a second polymerase through a cleavable linker (e.g., a peptide linker containing a specific protease site). The second polymerase is fused to a SpyCatcher domain. A SpyTagged streptavidin bearing a pentaphosphate group is reacted with the SpyCatcher-polymerase fusion. A barcode nucleic acid is bound to the second polymerase. The relative position and orientation of the protease site, polymerases, and inhibitory polyphosphate are designed such that 1) the polyphosphate inhibits the first polymerase but not the second polymerase (e.g. by fusing the SpyCatcher C-terminal to the second polymerase) and 2) cleavage at the protease site removes both the inhibitory polyphosphate and the second polymerase/barcode complex. As seen in FIG. 15B, addition of protease results in release of the second polymerase/barcode complex and of the inhibitory polyphosphate, enabling the first polymerase to sequence.

For many applications, the barcode is read first and the nucleic acid of interest is read second as described above. When desired, however, it will be evident that the nucleic acid of interest can be complexed with an active polymerase and read first, while the barcode nucleic acid is complexed with an inhibited polymerase and read second.

Barcoding can be useful, for example, in single molecule sequencing. Accordingly, one class of embodiments provides methods of sequence determination in which a barcoded complex is provided that comprises a first polymerase enzyme complexed to a barcode nucleic acid and a second polymerase enzyme complexed to a template nucleic acid. The first polymerase enzyme is active and the second polymerase enzyme is inhibited. The barcode nucleic acid is subjected to a polymerization reaction in which the first polymerase enzyme replicates at least a portion of the barcode nucleic acid in a template-dependent manner, whereby one or more nucleotides and/or nucleotide analogs are incorporated into the resulting first nucleic acid product, and a time sequence of incorporation of the one or more nucleotides and/or nucleotide analogs into the resulting first nucleic acid product is identified. The first polymerase enzyme is optionally inhibited, inactivated, or removed. Inhibition of the second polymerase enzyme is then released, and the template nucleic acid is subjected to a polymerization reaction in which the second polymerase enzyme replicates at least a portion of the template in a template-dependent manner, whereby one or more nucleotides and/or nucleotide analogs are incorporated into the resulting second nucleic acid product. A time sequence of incorporation of the one or more nucleotides and/or nucleotide analogs into the resulting second nucleic acid product is identified. The subjecting steps can be performed in a nanoscale well or other reaction region, e.g., in which the polymerases are immobilized. Suitable approaches for inhibiting the second polymerase and releasing the inhibition have been detailed above. In one class of embodiments, the first polymerase enzyme and the second polymerase enzyme are connected by a cleavable linker. After the first polymerization step, the barcode complex is exposed to a cleavage agent to remove the first polymerase enzyme from the complex, e.g., by diffusion or washing.

In other embodiments in which a mixture of inhibited and uninhibited polymerase enzymes are provided, an inhibited and an uninhibited polymerase are bound to a single template nucleic acid. This configuration can be useful, for example, in single molecule sequencing. Accordingly, one class of embodiments provides methods of sequence determination in which a complex is provided that comprises a template nucleic acid to which are bound a first polymerase enzyme and a second polymerase enzyme. The first polymerase enzyme is active and the second polymerase enzyme is inhibited. The template nucleic acid is subjected to a polymerization reaction in which the first polymerase enzyme replicates at least a portion of the template in a template-dependent manner, whereby one or more nucleotides and/or nucleotide analogs are incorporated into the resulting first nucleic acid product, and a time sequence of incorporation of the one or more nucleotides and/or nucleotide analogs into the resulting first nucleic acid product is identified. The first polymerase enzyme is optionally inhibited, inactivated, or removed. Inhibition of the second polymerase enzyme is then released, the template nucleic acid is subjected to a polymerization reaction in which the second polymerase enzyme replicates at least a portion of the template in a template-dependent manner, whereby one or more nucleotides and/or nucleotide analogs are incorporated into the resulting second nucleic acid product, and a time sequence of incorporation of the one or more nucleotides and/or nucleotide analogs into the resulting second nucleic acid product is identified. The subjecting steps can be performed in a nanoscale well or other reaction region, e.g., in which the polymerases are immobilized. Suitable approaches for inhibiting the second polymerase and releasing the inhibition have been detailed above.

Figure 9:
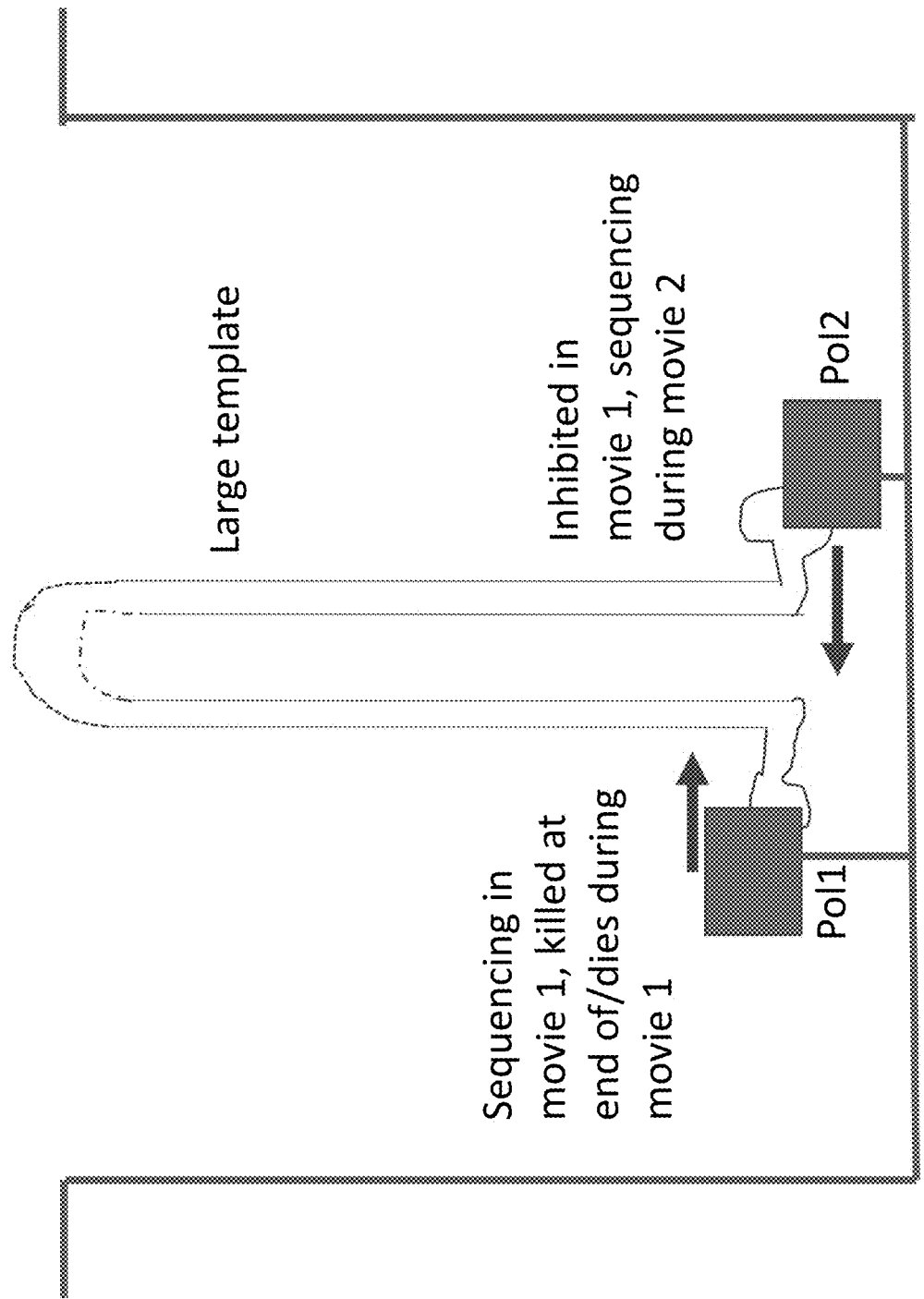
FIG. 9 schematically illustrates determination of the sequence of a nucleic acid template from both ends using an initially active and an initially inhibited polymerase.

Applications for these methods include sequencing long templates, for example, a template longer than the average read length achieved by a single polymerase molecule. In such embodiments, the first polymerase can sequence from one end of the template while the second polymerase sequences from the other end, e.g., of the complementary strand. Optionally, the two reads overlap in the middle of the template; in other embodiments, paired end reads are obtained. An exemplary embodiment is schematically illustrated in FIG. 9. A template containing a long double-stranded central region and two single-stranded hairpin end regions has a first, active polymerase bound to one end region and a second, inhibited polymerase bound to the other end region. The two end regions typically (but need not) differ in their sequence. Sequence is obtained from the first polymerase, which can be inactivated either intentionally or through photodamage during the sequencing process. Sequence is then obtained from the second polymerase. As shown in FIG. 9, the two polymerases are immobilized on the base of a nanoscale well, e.g., by binding of biotinylated polymerase to streptavidin that is in turn bound to the biotinylated base of the well. Including a crosslinker between the two polymerases can improve their immobilization. The crosslinker is optionally cleaved after immobilization is complete. Another application includes sequencing damaged templates, for example, a double-stranded template including a nick (or other damage that a polymerase cannot read through) on one strand. In this example, one polymerase can provide sequence until it encounters the damage on its strand, while the other polymerase provides additional sequence since its strand is not damaged. The two reads optionally overlap, and the other polymerase can optionally sequence the full length of its template strand.

Figure 10:
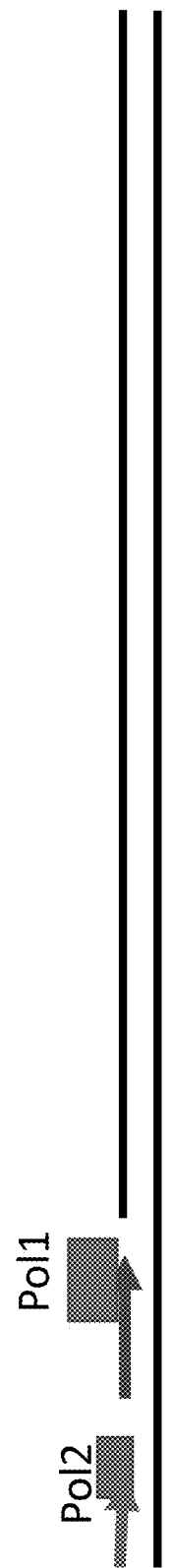
FIG. 10 schematically illustrates determination of the sequence of a nucleic acid template from one end using an initially active and an initially inhibited polymerase.

Another exemplary embodiment is schematically illustrated in FIG. 10. In this embodiment, an inhibited polymerase is bound to the template 5' of an active polymerase. Directionality is indicated relative to a nascent strand produced by the active polymerase. The template is optionally linear as illustrated in FIG. 10, but it can have other configurations (e.g., circular). The binding sites of the two polymerases (e.g., their primer binding sites and/or the sites at which they will initiate polymerization) are optionally proximal, e.g., within about 1 kb of each other (e.g., within about 500 nucleotides, 100 nucleotides, or 50 nucleotides of each other). Sequence information can be obtained from the first, active polymerase, which can be inactivated either intentionally or through photodamage during the sequencing process. Inhibition of the second polymerase can then be relieved and sequence information can be obtained from it, for example, for comparison with the first read or to obtain sequence not provided by the first polymerase (e.g., from a barcode located between the first and second polymerase binding sites).

For embodiments in which a single template is read with two different polymerases, optionally the two polymerases are selected to have different kinetic profiles and/or error modes (e.g., with respect to deletions and insertions), such that the combined read (incorporating information from both polymerases' reads) can have higher accuracy than would a combined read incorporating two reads produced by a single type of polymerase.

In another class of embodiments in which two polymerase enzymes are provided, one polymerase is employed to monitor loading, and the other polymerase is then used for analysis (e.g., sequencing). Different templates are typically provided for the two polymerases. In an exemplary embodiment, the first polymerase is bound to a nucleic acid of interest (e.g., one whose sequence is to be determined). The first polymerase is connected to a second, accessory polymerase through a cleavable linker (for example, the first polymerase can include a peptide linker containing a specific protease site followed by a SpyCatcher domain while the second polymerase includes a SpyTag). The second polymerase is bound to an accessory template having a different templating base than does the nucleic acid of interest (e.g., an A while the nucleic acid of interest has a T). The complex including both polymerases and nucleic acids is loaded and immobilized (for example, the first polymerase can be bis-biotinylated and immobilized via binding to streptavidin that is in turn bound to a biotinylated surface, thereby also immobilizing the second polymerase). Loading is monitored, e.g., by tracking cognate sampling signals from fluorescently labeled T nucleotides that interact with the accessory polymerase and its template. (As detailed above, both polymerases can be maintained in an inactive state, e.g., by provision of a suitable divalent cation, or the fluorescently labeled nucleotide can be an unincorporatable analog.) Photodamage that occurs during loading will thus affect the accessory, second polymerase rather than the first polymerase, primarily if not entirely. Once the desired loading level is achieved, the peptide linker connecting the first and second polymerases is cleaved to remove the second polymerase and accessory template. The first polymerase can then be employed for sequencing the nucleic acid of interest. The first polymerase can, but need not be, inhibited during loading (e.g., by polyphosphate binding) as detailed herein. While this example has been described with reference to use of one polymerase to track loading of another polymerase, it will be evident that a polymerase can be used to track loading of essentially any desired molecule of interest. Similarly, essentially any labeled species (a labeled peptide, protein, etc.) can be used to track loading of a polymerase and then removed to avoid interfering with subsequent analysis involving the polymerase.

Compositions, systems, and kits related to, produced by, or of use in the methods are another feature of the invention. For example, one class of embodiments provides an array of nanoscale wells, wherein a plurality of the wells have immobilized therein at least one inhibited polymerase enzyme complex comprising an inhibited polymerase enzyme complexed to a template nucleic acid. The wells can also include at least one active polymerase enzyme complex comprising an active polymerase enzyme complexed to a template nucleic acid (e.g., to the same or to a different template nucleic acid). In some embodiments, the inhibited polymerase enzyme is connected (covalently or noncovalently) through a cleavable linker to an active polymerase enzyme, which active polymerase enzyme is complexed to a different template nucleic acid (e.g., a barcode nucleic acid). Essentially all of the features noted above apply to these embodiments as well, as relevant, e.g., with respect to polymerase inhibition, template configuration, immobilization of the complex, and/or the like. For example, the polymerase enzyme complexes can comprise a primer hybridized to the template nucleic acid, wherein the primer is linked to a nonhydrolyzable nucleotide analog by a cleavable tether, or the polymerase enzyme can be inhibited by binding of a polyphosphate moiety to the polymerase enzyme, or the polymerase enzyme complexes can comprise a primer hybridized to the template nucleic acid, which primer comprises a reversible terminating group at its 3' end. The array is optionally employed in a nucleic acid sequencing system.

Another class of embodiments provides a complex comprising a template nucleic acid to which are bound a first polymerase enzyme and a second polymerase enzyme, wherein the first polymerase enzyme is active and the second polymerase enzyme is inhibited. Essentially all of the features noted above apply to these embodiments as well, as relevant, e.g., with respect to polymerase inhibition, template configuration, immobilization of the complex, and/or the like. For example, the complex can include a first primer hybridized to the template nucleic acid and bound to the first polymerase enzyme and a second primer hybridized to the template nucleic acid and bound to the second polymerase enzyme, wherein the second primer comprises a reversible terminating group at its 3' end. In some embodiments, the template nucleic acid comprises a double-stranded central region and two single-stranded hairpin regions, and the first polymerase enzyme is bound to one end region and the second polymerase enzyme is bound to the other end region. In some embodiments, the second polymerase enzyme is bound to the template nucleic acid 5' of and optionally proximal to the first polymerase enzyme, wherein directionality is relative to a nascent strand produced by the first polymerase enzyme. The template nucleic acid can be immobilized in a nanoscale well, e.g., in the observation volume, optionally through one or more biotin moieties on the polymerase. The composition is optionally present in a nucleic acid sequencing system.

Another class of embodiments provides a complex that includes a first polymerase enzyme complexed to a first nucleic acid and a second polymerase enzyme complexed to a second nucleic acid, wherein the first and second polymerase enzymes are connected by a cleavable linker. In some embodiments, the first polymerase enzyme is inhibited and the second polymerase enzyme is active; in other embodiments, the second polymerase enzyme is inhibited and the first polymerase enzyme is active. In some embodiments, the first nucleic acid is a target nucleic acid whose sequence is to be determined. Optionally, the sequence of the second nucleic acid identifies the origin of the first nucleic acid. For example, in one class of embodiments, the first polymerase enzyme is inhibited and the second polymerase enzyme is active, the first nucleic acid is a target nucleic acid whose sequence is to be determined, and the second nucleic acid is a barcode nucleic acid whose sequence identifies the origin of the first nucleic acid. The complex can be immobilized in a nanoscale well, e.g., in the observation volume, optionally through one or more biotin moieties on the polymerase. The complex is optionally present in a nucleic acid sequencing system.

V. Tuning Polymerase Enzyme Complex Loading by Modulating Immobilization

As noted, polymerase complexes are often immobilized in nanoscale wells (e.g., in the observation volume) or in other reaction regions to facilitate analysis. Controlling immobilization of the complexes can thus facilitate achievement of the desired degree of loading. Thus, in one aspect, the present disclosure provides methods for establishing polymerase enzyme complexes (e.g., single active polymerase enzyme complexes) in a predetermined number of nanoscale wells by altering the immobilization of complexes in the nanoscale wells.

In one aspect, the polymerase enzyme complexes are configured to allow reversible binding of the complex to a capture moiety in the wells, facilitating control and ability to tune during the real-time loading process. Accordingly, one class of embodiments provides methods for loading polymerase enzyme complexes into a predetermined number of nanoscale wells. In the methods, a surface comprising an array of nanoscale wells is provided. The base of the nanoscale wells comprises a capture moiety. A loading solution that includes polymerase enzyme complexes comprising a template nucleic acid and a polymerase enzyme is contacted to the surface. The polymerase enzyme complexes reversibly bind to the capture moiety in the nanoscale wells. Typically, the loading solution also includes one or more nucleotides and/or nucleotide analogs, and interactions between the nucleotides and/or nucleotide analogs and the polymerase enzyme complexes result in generation of signal pulses. As detailed above, in some embodiments, the labeled nucleotide analog is added to a nascent strand complementary to the complexed template nucleic acid and signal is detected as the labeled analog is retained in the complex during incorporation, while in other embodiments, signals are a result of cognate sampling. While the loading solution is in contact with the surface, the array of nanoscale wells is monitored to detect signal pulses from within the wells and thereby to identify nanoscale wells that have been loaded with a polymerase enzyme complex. The number or concentration of polymerase enzyme complexes in the loading solution can be increased (e.g., by addition of more complexes) or reduced (e.g., by removal of at least a portion of the loading solution, e.g., by washing the array, or by diluting the loading solution) as needed until the predetermined number of nanoscale wells have been loaded with a polymerase enzyme complex. As for the embodiments above, loading progress can be monitored continuously or intermittently. Once the predetermined number of nanoscale wells have been loaded with a polymerase enzyme complex, the polymerase enzyme complexes are covalently attached to the capture moiety, for example, through a crosslinker as known in the art. Any excess polymerase complexes that are not immobilized on the array can be removed, e.g., by washing the array, before or after the covalent attachment step.

The capture moiety can be essentially any group, molecule, etc. to which the polymerase enzyme complex can be reversibly bound. Examples include, e.g., streptavidin and other biotin-binding proteins such as avidin, deglycoslylated avidin (NeutrAvidin), traptavidin, tamavidin, rhizavidin, or a variant, mutant, or derivative thereof, biotin or a biotin analog such as a biotin sulfoxide, iminobiotin, desthiobiotin (also known as dethiobiotin), oxybiotin, carbobiotin, selenobiotin, carboxybiotin, homobiotin, norbiotin, diaminobiotin, biotin sulfone, epibiotin, 5-hydroxybiotin, 2-thiobiotin, azabiotin, methylated derivatives of biotin (e.g., biotin methyl ester), or ketone biotin, small molecule coupling groups, macromolecular coupling groups, antibodies, antibody fragments, binding peptides, lectins, complementary nucleic acids, or any of a variety of other binding groups. Typically, one member of a binding pair (biotin/streptavidin, two complementary oligonucleotides, epitope/antibody, etc.) is located on the polymerase and the other member of the pair is located in the well.

In one exemplary class of embodiments, the polymerase enzyme is desthiobiotinylated, and the well contains a biotin-binding protein such as streptavidin, avidin, deglycoslylated avidin (NeutrAvidin), traptavidin, tamavidin, rhizavidin, or a variant, mutant, or derivative thereof (e.g., immobilized in the observation volume). Desthiobiotin binds less tightly to avidin and streptavidin than does biotin and thus results in a shorter dwell time within the nanoscale well for a desthiobiotinylated than a biotinylated complex. In such embodiments, the number of polymerase enzyme complexes in the loading solution can be increased or reduced to tune loading until the predetermined number of nanoscale wells have been loaded with a polymerase enzyme complex. Once the predetermined number of nanoscale wells have been loaded, the polymerase enzyme complexes can be immobilized in the nanoscale wells, thereby fixing the number of polymerase enzyme complexes within the wells. That immobilization can be accomplished using any methods described herein and known in the art, including methods of covalently attaching the polymerase enzyme complexes to the capture moieties within the nanoscale wells. For example, the polymerase enzyme complexes can be covalently attached to the nanoscale wells by crosslinking the desthiobiotin moieties on the polymerases to streptavidin moieties in the nanoscale wells. In an exemplary embodiment, the polymerase enzyme comprises desthiobiotin, and also comprises a reactive cysteine in proximity to the desthiobiotin, while the nanoscale wells comprise a streptavidin moiety with a reactive cysteine. In such embodiments, covalently attaching the polymerase enzyme complexes to the capture moiety in the nanoscale wells can comprise applying a bismaleimide reagent to crosslink the reactive cysteine on the polymerase enzyme to the reactive cysteine on the streptavidin in the nanoscale well. Suitable crosslinking reagents are well known in the art. Useful bismaleimide reagents include, but are not limited to, 1,8-bismaleimido-diethyleneglycol (BM-PEG) 2 or 3, bis(maleimido)ethane (BMOE), 1,4-bis(maleimide)butane (BMB), and bis(maleimido)hexane (BMH).

In one aspect, an excess of polymerase enzyme complexes is immobilized in an array of nanoscale wells, and then complexes are removed from the array until the desired number of wells contain a single or at least one complex. Accordingly, one general class of embodiments provides methods for immobilizing polymerase enzyme complexes within a predetermined number of nanoscale wells, in which the polymerase enzyme complexes are delivered to an array of nanoscale wells and immobilized within the wells through a cleavable linker. In general, such immobilization occurs within an observation volume of the nanoscale well. The polymerase enzyme complexes are then exposed to a cleavage agent for a period of time until a predetermined number of the nanoscale wells contain a polymerase enzyme complex (e.g., a single polymerase enzyme complex).

As will be appreciated, after the polymerase enzyme complexes are delivered to the array of nanoscale wells, different wells within the array may contain no complexes, a single complex, or multiple complexes. In some embodiments, the polymerase enzyme complexes are delivered at a concentration such that a majority of the nanoscale wells contain (and/or have immobilized within their observation volume) two or more polymerase enzyme complexes. Regardless of the level of loading of the individual wells, as the complexes are exposed to the cleavage agent, a plurality of the singly and multiply occupied wells will "lose" complexes, meaning that one or more of the complexes will be released from immobilization and will diffuse out of the observation volume of the wells. Once a predetermined number of wells across the array contains a polymerase enzyme complex, exposure to the cleavage agent is ceased. For example, the cleavage agent can be inactivated (e.g., by addition of an inhibitor) or removed (e.g., by washing the array) to prevent any further modulation of the remaining immobilized polymerase enzyme complexes. If necessary, the level of occupancy of the wells can also be further tuned by adding additional polymerase enzyme complexes to the array as needed to reach the predetermined level of occupied nanoscale wells.

The level of loading across the array of nanoscale wells can be monitored by detecting signals generated by polymerase enzyme complexes. In certain embodiments, the nanoscale wells contain one or more labeled nucleotide analogs, and interactions between the nucleotide analogs and the polymerase enzyme complexes results in the generation of signal pulses. As detailed above, in some embodiments, the labeled nucleotide analog is added to a nascent strand complementary to the complexed template nucleic acid and signal is detected as the labeled analog is retained in the complex during incorporation, while in other embodiments, signals are a result of cognate sampling. In some embodiments, the array of nanoscale wells is configured such that only signals generated by polymerase enzyme complexes that are located within the wells (e.g., in an observation volume) can be detected. As such, the loading of individual wells can be monitored by monitoring the signals generated by the complexes within the wells. The monitoring can be continuous throughout the process of loading, immobilizing, and/or modulating the immobilization of the complexes, or the monitoring can be intermittent at fixed or random timepoints during one or more different aspects of the process. In one exemplary embodiment, monitoring is performed (continuously or intermittently) while the immobilized complexes are exposed to the cleavage agent, and the agent is removed or inactivated when the desired number of wells contain an active complex. Optionally, monitoring can be accomplished in the presence of photodamage mitigating agents, including those known in the art and described in further detail herein. In exemplary embodiments, such photodamage mitigating agents can include reducing agents, anti-fade agents, oxygen scavenging agents, and/or the like, thus preventing damage to enzymes during the detection of the level of occupancy of the nanoscale wells. In another exemplary embodiment, the level of loading is assessed, a suitable concentration of cleavage agent and exposure time are determined (e.g., from comparison to previously determined standards), and the array is exposed to the cleavage agent accordingly. The resulting level of loading can be subsequently determined to confirm that it reached the desired number of occupied wells. In such embodiments, potential for photodamage is minimized, since the array is not monitored during the exposure step. In another exemplary embodiment, two or more arrays are loaded under equivalent conditions. The number of wells containing at least one active complex is determined for one of the arrays, and a suitable time for treatment with the cleavage agent is established for that array by monitoring the cleavage process. The remaining arrays are then treated using the same conditions, and may or may not be monitored during such treatment.

In some embodiments, a first set of polymerase enzyme complexes are immobilized within the nanoscale wells through a cleavable linker (i.e., a linker that is subject to cleavage by a cleavage agent) and a second set of polymerase enzyme complexes are immobilized within the nanoscale wells through linkers that are not subject to cleavage by the cleavage agent. The first and second set of polymerase enzyme complexes can be delivered to the array of nanoscale wells simultaneously or separately. The use of complexes with and without cleavable linkers provides an ability to tune the level of loading of the nanoscale wells to arrive at the predetermined number of occupied sites, because application of the cleavage agent will only affect the complexes containing the susceptible linker. As discussed in further detail below, different combinations of types of cleavable of linkers can also be utilized in known ratios, such that application of the appropriate cleavage agent would only affect the immobilization of a defined fraction of the population of complexes (e.g., those immobilized through linkers susceptible to that particular cleavage agent). Thus, determining the level of occupancy (or over-occupancy) can inform which cleavage agent to use to remove a desired average number of immobilized complexes, depending on the fraction of the full population that contains a linker that is susceptible to a particular agent. It will be evident that mixtures including two or more complexes with linkers subject to cleavage by different agents and complexes with linkers not subject to cleavage by any of the agents can also be employed.

As will be appreciated, the complexes can immobilized in the nanoscale wells through any type of linker, with the caveat that linkers that are to be modified by a cleavage agent must contain the requisite site for the cleavage agent to act upon. Linkers of use for the methods described herein can include without limitation nucleic acid linkers, PNA, LNA, linkers containing phosphate or phosphonate groups, amino acid linkers, peptide linkers, substituted or unsubstituted alkyl (such as alkane or alkene linkers of from about C20 to about C30), substituted or unsubstituted heteroalkyl, substituted or unsubstituted aryl, substituted or unsubstituted heteroaryl, substituted or unsubstituted cycloalkyl, substituted or unsubstituted heterocycloalkyl, poly(ethylene glycol) (PEG) groups, and/or saturated or unsaturated aliphatic structures comprised of single or connected rings.

Figure 18:
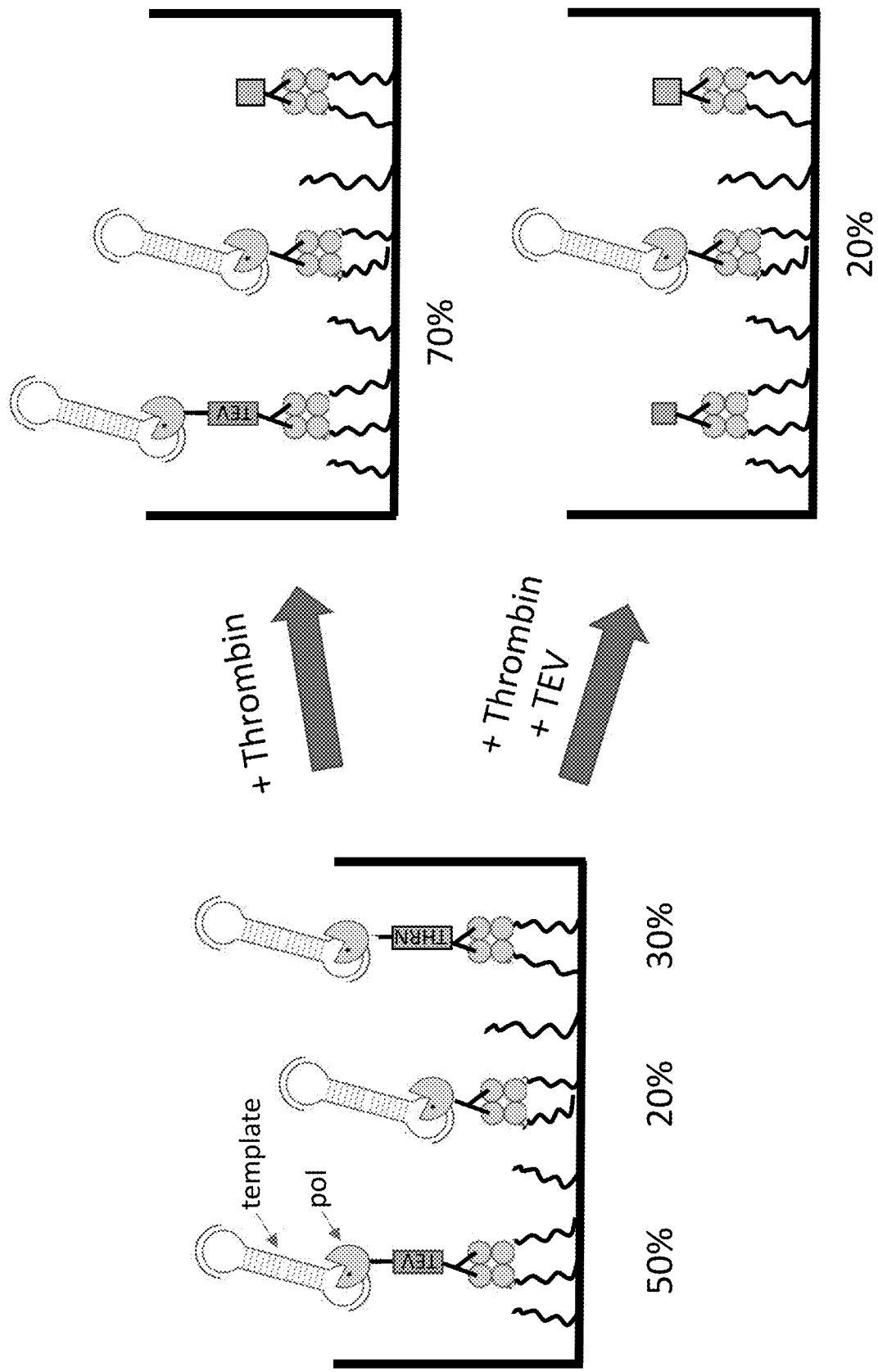
FIG. 18 schematically illustrates adjustment of loading level by tuning polymerase immobilization via protease digestion of susceptible linkers.

In some embodiments, the linker comprises a peptide and the cleavage agent is a protease to which the peptide is susceptible. Such proteases can include without limitation thrombin, Tobacco Etch Virus (TEV) protease, enterokinase, trypsin, rhinovirus protease (such as 3C rhinovirus protease), and the like. In some embodiments and as discussed above, a mixture of polymerase enzyme complexes can be used where part of the population is susceptible to a particular protease and part is not susceptible to that protease. Application of the protease would then affect the immobilization of only part of the population of loaded and immobilized complexes, thus allowing further tuning of the level of occupancy in the nanoscale wells. In some embodiments and as discussed above, combinations of linkers susceptible to different proteases can be utilized. For example, as illustrated in FIG. 18, if the population of polymerase enzyme complexes delivered to the nanoscale well array contain a ratio of 20 complexes with noncleavable linkers to 30 complexes with thrombin-cleavable linkers to 50 complexes with TEV-cleavable linkers, then an array that is somewhat overloaded can be tuned to the predetermined occupancy level by adding thrombin to effectively reduce the number of complexes in wells by 30%. Similarly, TEV can be added to modulate complex immobilization and effectively reduce the number of complexes in wells by 50%. If the array is quite overloaded, then addition of both thrombin and TEV results in the predetermined level of occupancy by reducing the number of complexes in wells by 70%. In this way, the level of modulation of immobilization can be tuned by constructing a population of polymerase enzyme complexes that contains a known distribution of linkers with defined sensitivities to particular cleavage agents. In such embodiments, cleavage can be performed essentially to completion, without requiring continuous monitoring of the reaction and timely removal or inactivation of the protease.

In some embodiments utilizing protease susceptible linkers, the time required to utilize the protease digest effectively can be determined by calibration experiments that are conducted separately from the loading process. Such calibration allows modulation of immobilization to be conducted separately from determination of the extent of loading. For example, the number of loaded nanoscale wells can first be determined, in some embodiments in an illuminated mode that allows signals to be generated from interactions between labeled nucleotides or nucleotide analogs and the polymerase enzyme complexes. Then the protease can be applied, in some embodiments in a non-illuminated mode to halt the generation of signals, for an amount of time sufficient to tune the number of occupied wells to the predetermined level. Such methods allow for the use of proteases that may not be efficient cleavage agents under conditions that allow the polymerase enzyme complexes to generate signals (e.g., sequencing reaction conditions). Such methods can also limit photodamage to the complexes.

In some embodiments, the cleavable linker comprises DNA and the cleavage agent comprises an endonuclease (e.g., a restriction enzyme). In some embodiments, the cleavable linker comprises RNA and the cleavage agent comprises an RNase.

In some embodiments, upon its addition the cleavage agent diffuses freely in the solution surrounding the polymerase complexes. For example, a protease can be added to the loading solution overlying the array of nanoscale wells. In other embodiments, the cleavage agent can be localized to the complexes, for example, by attaching it to a nucleotide analog. In one class of embodiments, before the complex is exposed to the cleavage agent, the template nucleic acid is subjected to a polymerization reaction in which the polymerase enzyme replicates at least a portion of the template in a template-dependent manner, whereby one or more nucleotides and/or nucleotide analogs are incorporated into resulting nucleic acid product, and then the polymerization reaction is halted, e.g., by replacing $Mg^{2+}$ with $Sr^{2+}$ (or another noncatalytic ion). The templating base will now be different for different polymerase complexes (e.g., about 25% A, 25% C, 25% G, and 25% T). Only a brief extension step is typically required, since the goal is randomization of the templating base. Extension can be performed prior to, during, and/or after immobilization of the complexes, as convenient. Following extension and immobilization, a cleavage agent tethered to a base is added, e.g., after initial loading of the array has been assessed. The base can associate with its cognate base on the template nucleic acid; the cleavage agent is therefore at a high local concentration, e.g., for approximately 25% of the complexes (i.e., those that include the complementary templating base). If two such bases with attached cleavage agent are used, approximately 50% of the complexes will be exposed to a high local concentration of the cleavage agent, while if three bases with attached cleavage agent are employed, approximately 75% of the complexes will be exposed to a high local concentration of the cleavage agent. The number of different base analogs having an attached cleavage agent can therefore be adjusted according to the degree of overloading of the array.

Alternatively or in addition, cleavage level can be modulated by inclusion of nucleotides or analogs complementary to the templating base but not including the cleavage agent. As just one example, a mixture that is 50% T analog and 50% protease-linked T analog can be provided when cleavage of less than 25% of the complexes is desired. It will be evident that the relative concentrations of analog and cleavage agent-linked analog can be adjusted to achieve the desired level of digestion. Although pre-extension of a primer bound to the template nucleic acid can randomize the templating base as described above, this pre-extension step can be omitted, particularly in embodiments in which a mixture of analog and cleavage agent-linked analog is employed. As one example, for a template/primer in which the templating base is a T, adding a mixture of dA analog and a small amount of protease-linked dA analog leads to a rate of cleavage that is proportional to the ratio of dA-protease and dA. The cleavage agent can be removed or effectively diluted, for example, by adding $Mg^{2+}$ and permitting incorporation of the nucleotide to break the linkage that holds the cleavage agent bound to the polymerase (e.g., where the cleavage agent is linked to the terminal phosphate of the analog). In a related class of embodiments, a protecting agent that prevents cleavage of the linker and that is tethered to a cognate base can be provided after the extension step and prior to addition of a free cleavage agent.

In some embodiments, the methods described herein can be conducted until a predetermined number of the nanoscale wells in the array contain an active polymerase enzyme complex (whether a single complex or more than one complex). For example, the predetermined number of nanoscale wells in the array occupied by a polymerase enzyme complex can be at least about 10%, at least about 20%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the nanoscale wells in the array. In some embodiments, the predetermined number of nanoscale wells occupied by a polymerase enzyme complex is about 10-100% of the nanoscale wells in the array, e.g., about 30-95%, about 35-90%, about 40-80%, about 45-85%, about 50-75%, about 55-70%, or about 60-80% of the nanoscale wells in the array. In some embodiments, at least a majority of the predetermined number of nanoscale wells are occupied by a single polymerase enzyme complex.

As will be appreciated, the methods can be conducted until a predetermined number of the nanoscale wells in the array contain a single active polymerase enzyme complex. The predetermined number of nanoscale wells occupied by a single active polymerase enzyme complex can be any number that is of use for downstream applications, such as sequencing reactions. In certain embodiments, the predetermined number of nanoscale wells is at least about 10%, at least about 20%, at least about 25%, at least about 30%, or at least about 35% of the nanoscale wells in the array. In some embodiments, the predetermined number of nanoscale wells occupied by a single polymerase enzyme complex is about 10-40% of the nanoscale wells in the array, e.g., about 20-35% of the nanoscale wells in the array.

In some embodiments, the methods are conducted until the average number of active polymerase complexes per well is about 0.7, about 0.8, about 0.9, about 1, about 1.1, about 1.2, about 1.3, about 1.4, about 1.5, about 1.6, about 1.7, about 1.8, about 1.9, about 2 or more. In some embodiments, the methods are conducted until the average number of active polymerase complexes per well is about 0.8-2, e.g., about 1-1.8 or about 1.2-1.6.

The methods can be combined with other methods described herein. For example, for multiplexed libraries, templates from one genomic library can be barcoded by association with a barcode/polymerase complex as detailed above and bound to a polymerase immobilized via a linker cleavable with a first agent, while templates from other libraries are associated with different barcodes and immobilized via linkers cleavable with other agents. The barcodes can be sequenced. If a particular library is overrepresented, it can be selectively depleted by addition of the corresponding cleavage agent.

In some embodiments, once the predetermined number of nanoscale wells are occupied by a polymerase enzyme complex, the array is further prepared for analyzing the polymerase enzyme complexes within the nanoscale wells. In certain embodiments, the array is prepared for conducting sequencing reactions in accordance with methods known in the art and described in further detail below.

Although the above embodiments have been described in reference to loading of polymerase complexes into nanoscale wells, it will be evident that the techniques can be applied to immobilization of essentially any desired molecule, complex, or reagent to essentially any surface. For example, a desired reagent can be reversibly bound to a capture moiety on a surface. The number, concentration, or the like of bound reagent is assessed, and once it reaches a desired level (e.g., over time or optionally at equilibrium), the reagent is covalently attached to the capture moiety.

VI. Compositions

The methods disclosed herein include processes for ensuring that a predetermined number of reaction sites in an array are occupied by a molecule of interest. In certain aspects, the array is an array of nanoscale wells, and the molecule of interest includes a complex of a polymerase enzyme and a template nucleic acid, where the template nucleic acid is in some aspects hybridized to a primer. Such complexes are able to under certain conditions generate signals that can be detected during the methods described herein—often, those signals are generated by a nucleotide or a nucleotide analog that is labeled or otherwise detectable associating with its cognate base on the template nucleic acid and/or being incorporated. The following sections provide details on different types of compositions and components of use in the methods described herein, including elements of the complexes that can be loaded into nanoscale wells. As will be appreciated, any of the compositions described herein can be used in any combination with each other and in any of the methods further detailed in the above sections.

VI.A. Template Molecules

The nucleic acids employed in the practice of the invention can be fully or partially double-stranded or can be single-stranded. Suitable nucleic acids include, but are not limited to, SMRTbells™ (circular nucleic acids having a double-stranded central region and single-stranded hairpin ends), double-stranded circular DNA molecules (e.g., nicked or gapped double-stranded circular DNA molecules, e.g., nicked or gapped plasmids), and linear molecules (e.g., genomic DNA fragments).

Nucleic acids, including template nucleic acids, can be prepared using techniques well known in the art, from essentially any desired sample. For further discussion of circular templates, including, e.g., simple circles and SMRTbells™ (circular nucleic acids having a double-stranded central region and single-stranded hairpin ends), see, e.g., U.S. Pat. No. 8,236,499 "Methods and Compositions for Nucleic Acid Sample Preparation," U.S. Pat. No. 8,153,375 "Compositions and Methods for Nucleic Acid Sequencing," and Travers et al. (2010) Nucl. Acids Res. 38(15):e159, each of which is incorporated herein by reference in its entirety for all purposes.

Any of the methods, compositions, systems, and complexes described herein can include template nucleic acid molecules, often as part of the polymerase enzyme complexes described herein. In general, a template nucleic acid is a molecule for which the complementary sequence is (or can be) synthesized in a polymerase reaction. As will be appreciated, template sequences can be of any length or structure. In some cases, the template nucleic acid is linear; in some cases, the template nucleic acid is circular. The template nucleic acid can be DNA, RNA, and/or a non-natural RNA or DNA analog. Any nucleic acid that is suitable for replication by a polymerase enzyme can be used as a template in the methods and systems described herein.

In some embodiments, the nucleic acids used in methods and compositions of the present invention comprise nucleic acids obtained from a sample. The sample may comprise any number of things, including, but not limited to, bodily fluids (including, but not limited to, blood, urine, serum, lymph, saliva, anal and vaginal secretions, perspiration and semen) and cells of virtually any organism, including, but not limited to, mammalian samples, e.g., human samples; environmental samples (including, but not limited to, air, agricultural, water and soil samples); biological warfare agent samples; research samples (e.g., in the case of nucleic acids, the sample may be the products of an amplification reaction, including both target and signal amplification, such as PCR amplification reactions; and purified samples, such as purified genomic DNA, RNA preparations, raw samples (bacteria, virus, genomic DNA, etc.). As will be appreciated by those in the art, virtually any experimental manipulation may have been done on the samples.

In some embodiments, nucleic acid molecules are obtained from a sample and fragmented for use in (or prior to use in) methods of the invention, e.g., as template nucleic acids. The fragments may be single or double stranded and may further be modified in accordance with any methods known in the art and described herein. Nucleic acids may be generated by fragmenting source nucleic acids, such as genomic DNA, using any method known in the art. In one embodiment, shear forces during lysis and extraction of genomic DNA generate fragments in a desired range. Also encompassed by the present disclosure are methods of fragmentation utilizing restriction endonucleases or transposases.

As will be appreciated, the nucleic acids may be generated from a source nucleic acid, such as genomic DNA, by fragmentation to produce fragments of a specific size. The nucleic acids can be, for example, from about 10 to about 50,000 nucleotides in length, e.g., 10-20,000, 50-1000, 10-100, 50-100, 50-300, 100-200, 200-300, 50-400, 50-600, 100-400, 200-400, 400-500, 300-600, 400-600, 500-600, 50-1000, 100-1000, 200-1000, 300-1000, 400-1000, 500-1000, 600-1000, 700-1000, 700-900, 700-800, 800-1000, 900-1000, 200-2000, 1500-2000, 1750-2000, 50-2000, 100-25000, 200-24000, 300-23000, 400-22000, 500-21000, 600-20000, 700-19000, 800-18000, 900-17000, 1000-16000, 1100-15000, 1200-14000, 1300-13000, 1400-12000, 1500-11000, 1600-10000, 1700-9000, 1800-8000, 1900-7000, 2000-6000, 2100-5000, 2200-4000, 2300-3000, 5000-20000, 10000-30000, 12000-28000, 14000-26000, 16000-24000, 18000-22000, or 19000-20000 nucleotides in length. In some embodiments, the nucleic acids are at least 5000, 10000, 15000, 20000, 25000, 30000, 40000, 50000, 60000, 70000, 80000, 90000, 100,000, 120,000, 130,000, 140,000, 150,000, 200,000, 500,000, or 1,000,000 nucleotides in length. In some embodiments, the nucleic acids are part of polymerase-template complexes. In some embodiments, the nucleic acid templates are themselves further hybridized to primers.

In some cases, the template sequence may be a linear single or double stranded nucleic acid sequence. In still other embodiments, the template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220,674, filed Jul. 25, 2008, and alternate functional circular constructs are also described in US Pat. App. Pub. No. 20090298075, the full disclosures of each of which are incorporated herein by reference in their entirety for all purposes and in particular for all teachings related to template nucleic acid constructs. Briefly, such alternate constructs include template sequences that possess a central double stranded portion that is linked at each end by an appropriate linking oligonucleotide, such as a hairpin loop segment (SMRTbells™). Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

In some aspects, the template nucleic acid used in the compositions of the present invention includes: a double stranded nucleic acid segment having a first and second end; a first hairpin oligonucleotide connecting each strand of the single template nucleic acid at the first end; and a second hairpin oligonucleotide connecting each strand of the single template nucleic acid at the second end. In some embodiments, the first hairpin and second hairpin oligonucleotide are identical. In other embodiments, the first hairpin and second hairpin oligonucleotides are not identical—in other words, the template nucleic acid, despite being an alternate circular construct, is nevertheless asymmetrical. In further embodiments, the first hairpin oligonucleotide includes a primer binding site whereas the second hairpin oligonucleotide includes a capture adapter (or vice versa). The capture adapter is generally of a sequence that can be used to enrich a population for the hairpins of choice—for example, in some embodiments, the capture adapter comprises a polyA sequence, thereby allowing capture using beads or column chromatography utilizing polyT sequences. In some embodiments, the capture adapter comprises at least one methoxy residue. In some embodiments, the capture adapter is complementary to an oligonucleotide attached to a bead, which can in further embodiments be a magnetic bead that can be used to enrich a population for template nucleic acids containing the capture adapter. In some embodiments in which the population of templates includes templates with different adapters or in which each template comprises a different adapter at each end, different beads can be used which contain oligonucleotides complementary to the different adapters. Thus, for templates with two different adapters, two different beads can be used. For populations containing a plurality of different adapters, a concomitant number of different types of beads can be used that are directed to those adapters. In other embodiments, the same bead can contain different oligonucleotides complementary to the different adapters in the population of templates, such that the same bead can capture different adapters (and their associated templates).

In some embodiments, the first or second hairpin comprises a self-primed adapter sequence in which the primer is part of the adapter. In such embodiments, an additional oligonucleotide primer is not needed to allow a polymerase molecule to begin replicating the template.

In some embodiments, the nucleic acid template contains only a single hairpin at one end or the other.

The polymerase enzymes of use in the methods and compositions described herein generally require a primer. While in most cases an oligonucleotide primer is used, in some cases a protein such as a terminal protein can acts as a primer. Oligonucleotide primers are generally complementary to a portion of the template nucleic acid. The primers can comprise naturally occurring RNA or DNA oligonucleotides. The primers may also be synthetic analogs. The primers may have alternative backbones as described above. The primers may also have other modifications, such as the inclusion of heteroatoms, the attachment of labels, such as dyes, or substitution with functional groups which will still allow for base pairing and for recognition by the enzyme. Primers can select tighter binding primer sequences, e.g., GC rich sequences, as well as employ primers that include within their structure non-natural nucleotides or nucleotide analogs, e.g., peptide nucleic acids (PNAs) or locked nucleic acids (LNAs), that can demonstrate higher affinity pairing with the template. The primers can also be selected to influence the kinetics of the polymerase reaction through the use of length, nucleotide content, and/or any of the modifications discussed above. In other embodiments, self-priming templates are employed. For example, a SMRTbell™ (circular nucleic acid having a double-stranded central region and single-stranded hairpin ends) including a self-primed adapter sequence can be employed, as noted above. As another example, a double-stranded template including at least one nick or gap can be employed (e.g., a nicked or gapped double-stranded plasmid).

VI.B. Nucleotides and Nucleotide Analogs

Nucleotides of use in the present invention include, e.g., naturally occurring nucleotides such as dATP, dCTP, dGTP, and dTTP. Various nucleotide analogs are also of use in the present invention, as described in further detail below. The analogs are optionally detectably labeled.

In certain aspects described herein, non-incorporatable nucleotide analogs can be used, particularly for methods that rely on monitoring loading by detecting signals generated by interactions between nucleotides and/or nucleotide analogs and the cognate base on a template nucleic acid where the nucleotide and/or nucleotide analog is not incorporated into a nascent strand. Suitable non-incorporatable analogs are known in the art. See, e.g., U.S. Pat. Nos. 8,252,911, 8,530,164, and 8,652,781, previously incorporated by reference, for exemplary nonhydrolyzable (and therefore non-incorporatable) analogs. Exemplary nonhydrolyzable/non-incorporatable nucleotide analogs include, but are not limited to, analogs in which the phosphoester linkage between the alpha and beta phosphate of a nucleoside polyphosphate is replaced with a nonhydrolyzable linkage. For example, the oxygen group between the alpha and beta phosphate groups can be replaced with an nonhydrolyzable linkage, such as an amino, alkyl (e.g., methyl), thio, or other linkage not hydrolyzed by polymerase activity.

In certain aspects described herein, nucleotides that terminate extension (reversibly or essentially irreversibly) can be used. Suitable extension terminating nucleotides and analogs are known in the art and include, but are not limited to, dideoxynucleotide triphosphates (ddNTPs), 3'-blocked nucleotides (nucleotides or analogs without a free 3'-hydroxyl group), for example, 3'-O-azidomethyl dNTPs, 3'-O-amino dNTPs, 3'-O-allyl dNTPs, and 3'-O-methyl-dNTPs, and 3'-unblocked terminators. For discussion and examples of reversible terminators, see, e.g., U.S. Pat. No. 9,175,342 and Chen et al. (2013) "The history and advances of reversible terminators used in new generations of sequencing technology" Genomics Proteomics Bioinformatics 11:34-40, previously incorporated by reference.

In certain aspects herein, nucleotides and/or nucleotide analogs that can be incorporated into a nascent strand without blocking incorporation of subsequent nucleotides and/or nucleotide analogs can be used.

As discussed, various polymerases can incorporate one or more nucleotide analogs into a growing oligonucleotide chain. Upon incorporation, the nucleotide analog can leave a residue that is the same as or different than a natural nucleotide in the growing oligonucleotide (the polymerase can incorporate any non-standard moiety of the analog, or can cleave it off during incorporation into the oligonucleotide). A "nucleotide analog" herein is a compound, that, in a particular application, functions in a manner similar or analogous to a naturally occurring nucleoside triphosphate (a "nucleotide"), and does not otherwise denote any particular structure. A nucleotide analog is an analog other than a standard naturally occurring nucleotide, i.e., other than A, G, C, T, or U, though upon incorporation into the oligonucleotide, the resulting residue in the oligonucleotide can be the same as (or different from) an A, G, C, T, or U residue.

In one useful aspect of the invention, nucleotide analogs can be modified to achieve any properties desired. For example, various linkers or other substituents can be incorporated into analogs that have the effect of reducing branching fraction, improving processivity, or altering rates. Modifications to the analogs can include extending the phosphate chains, e.g., to include a tetra-, penta-, hexa- or heptaphosphate group, and/or adding chemical linkers to extend the distance between the nucleotide base and the dye molecule, e.g., a fluorescent dye molecule. Substitution of one or more non-bridging oxygen in the polyphosphate, for example with S or $BH_3$, can change the polymerase reaction kinetics. Optionally, one or more, two or more, three or more, or four or more non-bridging oxygen atoms in the polyphosphate group of the analog has an S substituted for an O. While not being bound by theory, it is believed that the properties of the nucleotide, such as the metal chelation properties, electronegativity, or steric properties, can be altered by substitution of the non-bridging oxygen(s).

Many nucleotide analogs are available and can be incorporated by polymerases. These include analog structures with core similarity to naturally occurring nucleotides, such as those that comprise one or more substituent on a phosphate, sugar, or base moiety of the nucleoside or nucleotide relative to a naturally occurring nucleoside or nucleotide. In one embodiment, the nucleotide analog includes three phosphate containing groups; for example, the analog can be a labeled nucleoside triphosphate analog and/or an α-thiophosphate nucleotide analog having three phosphate groups. In one embodiment, a nucleotide analog can include one or more extra phosphate containing groups, relative to a nucleoside triphosphate. For example, a variety of nucleotide analogs that comprise, e.g., from 4-6 or more phosphates are described in detail in US patent application publication 2007-0072196, incorporated herein by reference in its entirety for all purposes. Other exemplary useful analogs, including tetraphosphate and pentaphosphate analogs, are described in U.S. Pat. No. 7,041,812, incorporated herein by reference in its entirety for all purposes.

For example, the analog can include a labeled compound of the formula:

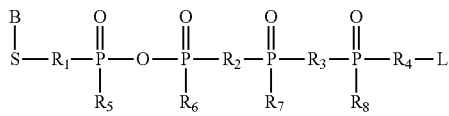

wherein B is a nucleobase (and optionally includes a label); S is selected from a sugar moiety, an acyclic moiety or a carbocyclic moiety (and optionally includes a label); L is an optional detectable label; $R_1$ is selected from O and S; $R_2$, $R_3$ and $R_4$ are independently selected from O, NH, S, methylene, substituted methylene, C(O), C(CH$_2$), CNH$_2$, CH$_2$CH$_2$, and C(OH)CH$_2$R where R is 4-pyridine or 1-imidazole, provided that $R_4$ may additionally be selected from

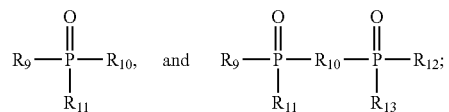

$R_5$, $R_6$, $R_7$, $R_8$, $R_{11}$ and $R_{13}$ are, when present, each independently selected from O, BH$_3$, and S; and $R_9$, $R_{10}$ and $R_{12}$ are independently selected from O, NH, S, methylene, substituted methylene, CNH$_2$, CH$_2$CH$_2$, and C(OH)CH$_2$R where R is 4-pyridine or 1-imidazole. In some cases, phosphonate analogs may be employed as the analogs, e.g., where one of $R_2$, $R_3$, $R_4$, $R_9$, $R_{10}$ or $R_{12}$ are not O, e.g., they are methyl etc. See, e.g., US patent application publication 2007-0072196, previously incorporated herein by reference in its entirety for all purposes.

The base moiety incorporated into the analog is generally selected from any of the natural or non-natural nucleobases or nucleobase analogs, including, e.g., purine or pyrimidine bases that are routinely found in nucleic acids and available nucleic acid analogs, including adenine, thymine, guanine, cytosine, uracil, and in some cases, inosine. As noted, the base optionally includes a label moiety. For convenience, nucleotides and nucleotide analogs are generally referred to based upon their relative analogy to naturally occurring nucleotides. As such, an analog that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogs, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

In the analogs, the S group is optionally a sugar moiety that provides a suitable backbone for a synthesizing nucleic acid strand. For example, the sugar moiety is optionally selected from a D-ribosyl, 2' or 3' D-deoxyribosyl, 2', 3'-D-dideoxyribosyl, 2', 3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties can be incorporated as the "S" group in place of a sugar moiety, including, e.g., those described in U.S. Patent Application Publication No. 2003/0124576, which is incorporated herein by reference in its entirety for all purposes.

For most cases, the phosphorus containing chain in the analogs, e.g., a triphosphate in conventional NTPs, is preferably coupled to the 5' hydroxyl group, as in natural nucleoside triphosphates. However, in some cases, the phosphorus containing chain is linked to the S group by the 3' hydroxyl group.

L generally refers to a detectable labeling group that is coupled to the terminal phosphorus atom via the $R_4$ (or $R_{10}$ or $R_{12}$ etc.) group. The labeling groups employed in the analogs employed in the invention may comprise any of a variety of detectable labels. Detectable labels generally denote a chemical moiety that provides a basis for detection of the analog compound separate and apart from the same compound lacking such a labeling group. Examples of labels include, e.g., optical labels, e.g., labels that impart a detectable optical property to the analog, electrochemical labels, e.g., labels that impart a detectable electrical or electrochemical property to the analog, and physical labels, e.g., labels that impart a different physical or spatial property to the analog, e.g., a mass tag or molecular volume tag. In some cases individual labels or combinations may be used that impart more than one of the aforementioned properties to the analogs of the invention.

A variety of labels are known in the art and can be adapted to the practice of the present invention. In one class of embodiments, the labels are optical labels, e.g., a fluorescent, a luminescent, a fluorogenic, a chemiluminescent, a chromophoric, or a chromogenic label, or another label that becomes detectable upon absorption of excitation radiation from an illumination source. Examples of preferred optically detectable labels include, e.g., organic fluorescent labels, such as cyanine-, fluorescein-, and/or rhodamine-based dyes, inorganic labels such as semiconductor nanocrystals, or quantum dots. In some embodiments, different labels share a fluorescent emission maximum but are nonetheless distinguishable by the amplitude of emission. Other examples of labels include particles that are optically detectable through their ability to scatter light. Such particles include any of the particle types described elsewhere, herein, and particularly, metal nanoparticles, e.g., gold, silver, platinum, cobalt, or the like, which may be detected based upon a variety of different light scatter detection schemes, e.g., Rayleigh/Mie light scattering, surface enhanced Raman scattering, or the like. Other suitable labels include, but are not limited to, electrically detectable labels, enzymatically detectable labels, electrochemically detectable labels, and labels detectable based upon their mass. Mass labels include, e.g., particles or other large moieties that provide detectable variations in mass of the molecule to which they are attached or vary the molecule's rotational diffusion. Electrochemical labels that detectably alter the charge of the molecule, magnetic labels, such as magnetic particles, or the like can be employed. Other examples of suitable labels include groups that affect the flow of current, i.e., groups that alter (e.g., enhance or reduce) impedance or conductance of the composition. Such labels are useful, e.g., in applications where incorporation is detected by changes in conductance or impedance, e.g., in nanopore-based nucleic acid sequencing applications or nanoFET-based nucleic acid sequencing applications. Examples of conductance impacting functional groups include, e.g., long alkane chains which optionally include solubility enhancing groups, such as amido substitutions; long polyethylene glycol chains; polysaccharides; particles, such as latex, silica, polystyrene, metal, semiconductor, or dendrimeric particles; branched polymers, such as branched alkanes, branched polysaccharides, branched aryl chains; highly charged groups or polymers; oligopeptides; and oligonucleotides. Useful labels may additionally or alternatively include electrochemical groups that may be detected or otherwise exploited for their electrochemical properties, such as their overall electric charge. For example, highly charged groups can be included, like additional phosphate groups, sulfate groups, amino acid groups or chains, e.g., polylysine, polyarginine, etc. Likewise, redox active groups, such as redox active compounds, e.g., heme, or redox active enzymes, can be included. Other label types may include, e.g., magnetic particles that may be sensed through appropriate means, e.g., magneto-tunnel junction sensors, etc.

Optionally, the labeling groups incorporated into the analogs comprise optically detectable moieties, such as luminescent, chemiluminescent, fluorescent, fluorogenic, chromophoric and/or chromogenic moieties, with fluorescent and/or fluorogenic labels being preferred. A variety of different label moieties are readily employed in nucleotide analogs. Such groups include, e.g., fluorescein labels, rhodamine labels, cyanine labels (i.e., Cy3, Cy5, and the like, generally available from the Amersham Biosciences division of GE Healthcare), and the Alexa family of fluorescent dyes and other fluorescent and fluorogenic dyes available from Molecular Probes/Invitrogen, Inc. and described in 'The Handbook—A Guide to Fluorescent Probes and Labeling Technologies, Eleventh Edition' (2010) (available from Invitrogen, Inc./Molecular Probes). A variety of other fluorescent and fluorogenic labels for use with nucleoside polyphosphates, and which would be applicable to the nucleotide analogs incorporated by polymerases, are described in, e.g., U.S. Patent Application Publication No. 2003/0124576, previously incorporated herein by reference in its entirety for all purposes.

Thus, in one illustrative example, the analog can be a phosphate analog (e.g., an analog that has more than the typical number of phosphates found in nucleoside triphosphates) that includes, e.g., an Alexa dye label. For example, an Alexa488 dye can be labeled on a delta phosphate of a tetraphosphate analog (denoted, e.g., A488dC4P or A488dA4P, for the Alexa488 labeled tetraphosphate analogs of C and A, respectively), or an Alexa568 or Alexa633 dye can be used (e.g., A568dC4P and A633dC4P, respectively, for labeled tetraphosphate analogs of C or A568dT6P for a labeled hexaphosphate analog of T), or an Alexa546 dye can be used (e.g., A546dG4P), or an Alexa594 dye can be used (e.g., A594dT4P). As additional examples, an Alexa555 dye (e.g., A555dC6P or A555dA6P), an Alexa 647 dye (e.g., A647dG6P), an Alexa 568 dye (e.g., A568dT6P), and/or an Alexa660 dye (e.g., A660dA6P or A660dC6P) can be used in, e.g., single molecule sequencing. Similarly, to facilitate color separation, a pair of fluorophores exhibiting FRET (fluorescence resonance energy transfer) can be labeled on a delta phosphate of a tetraphosphate analog (denoted, e.g., FAM-amb-A532dG4P or FAM-amb-A594dT4P).

As noted above, an analog can include a linker that extends the distance between the nucleotide base and the label moiety, e.g., a fluorescent dye moiety. Exemplary linkers and analogs are described in U.S. Pat. No. 7,968,702. Similarly, a protein or other moiety can be employed to provide spacing and/or shielding between the base and the label, e.g., as described in U.S. Pat. No. 9,062,091 "Polymerase Enzyme Substrates with Protein Shield," and U.S. Pat. No. 9,957,291 "Protected Fluorescent Reagent Compounds." Suitable polymerase substrates optionally include two or more nucleoside polyphosphates and/or two or more label moieties, e.g., as described in U.S. Pat. No. 9,062,091 "Polymerase Enzyme Substrates with Protein Shield," U.S. Pat. No. 9,957,291 "Protected Fluorescent Reagent Compounds," and US patent application publication 2009-0208957 Alternate Labeling Strategies for Single Molecule Sequencing.

Additional details regarding labels, analogs, and methods of making such analogs can be found in US patent application publication 2007-0072196, WO 2007/041342 Labeled Nucleotide Analogs and Uses Therefor, WO 2009/114182 Labeled Reactants and Their Uses, US patent application publication 2009-0208957 Alternate Labelling Strategies for Single Molecule Sequencing, U.S. Pat. No. 9,051,263 Functionalized Cyanine Dyes, U.S. Pat. No. 8,669,374 Functionalized Cyanine Dyes, U.S. Pat. No. 8,889,886 Cyanine Dyes, U.S. Pat. No. 8,906,612 Scaffold-Based Polymerase Enzyme Substrates, US patent application publication 2010-0167299 Phospholink Nucleotides for Sequencing Applications, US patent application publication 2010-0152424 Modular Nucleotide Compositions and Uses Therefor, U.S. Pat. No. 9,062,091 "Polymerase Enzyme Substrates with Protein Shield," U.S. Pat. No. 9,957,291 "Protected Fluorescent Reagent Compounds," U.S. Pat. Nos. 7,968,702 and 9,062,091, and U.S. patent application publications 2017/0145495, 2017/0145496, and 2017/0321268, each of which is incorporated herein by reference in its entirety for all purposes.

VI.C. Polymerases

Many of the methods and compositions of the present disclosure utilize polymerase enzymes (also referred to herein as "polymerases"). Any suitable polymerase enzyme can be used in the systems and methods disclosed herein, particularly as part of the polymerase enzyme complexes loaded into reaction sites in accordance with the above description. Suitable polymerases include DNA dependent DNA polymerases, DNA dependent RNA polymerases, RNA dependent DNA polymerases (reverse transcriptases), and RNA dependent RNA polymerases. In certain embodiments, the polymerases used in the methods and compositions of the present invention are strand-displacing polymerases.

As disclosed in further detail herein, polymerases of use in the presently disclosed methods can also include modifications that improve certain characteristics of the enzyme, including processivity, resistance to photodamage, and conduciveness to immobilization. In certain aspects, polymerases used in the methods and systems disclosed herein include a linker, motif (e.g., a biotin ligase recognition sequence), or domain through which the polymerases (and any other molecules they are complexed with, such as template nucleic acids and optionally replication initiating moieties) can be immobilized onto a surface e.g., through binding to a biotin-binding protein or other binding partner.

DNA polymerases are sometimes classified into six main groups based upon various phylogenetic relationships, e.g., with E. coli Pol I (class A), E. coli Pol II (class B), E. coli Pol III (class C), Euryarchaeotic Pol II (class D), human Pol beta (class X), and E. coli UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1): reviews 3002.1-3002.4; and Steitz (1999) "DNA polymerases: structural diversity and common mechanisms" J Biol Chem 274:17395-17398. The basic mechanisms of action for many polymerases have been determined. The three-dimensional structures of a large number of polymerases have been determined by x-ray crystallography and nuclear magnetic resonance (NMR) spectroscopy, including the structures of polymerases with bound templates, nucleotides, and/or nucleotide analogs. Many such structures are freely available for download from the Protein Data Bank, at (www(dot)rcsb(dot)org/pdb. Structures, along with domain and homology information, are also freely available for search and download from the National Center for Biotechnology Information's Molecular Modeling Data-Base, at www(dot)ncbi(dot)nlm(dot)nih(dot)gov/Structure/MMDB/mmdb(dot)shtml. The structures of Φ29 polymerase, Φ29 polymerase complexed with terminal protein, and Φ29 polymerase complexed with primer-template DNA in the presence and absence of a nucleoside triphosphate are available; see Kamtekar et al. (2004) "Insights into strand displacement and processivity from the crystal structure of the protein-primed DNA polymerase of bacteriophage Φ29" Mol. Cell 16(4): 609-618), Kamtekar et al. (2006) "The phi29 DNA polymerase:protein-primer structure suggests a model for the initiation to elongation transition" EMBO J. 25(6):1335-43, and Berman et al. (2007) "Structures of phi29 DNA polymerase complexed with substrate: The mechanism of translocation in B-family polymerases" EMBO J. 26:3494-3505, respectively. The structures of additional polymerases or complexes can be modeled, for example, based on homology of the polymerases with polymerases whose structures have already been determined. Alternatively, the structure of a given polymerase (e.g., a wild-type or modified polymerase), optionally complexed with a DNA or RNA (e.g., template and/or primer) and/or nucleotide analog, or the like, can be determined. information on structure determination and modeling is widely available in the art; see, e.g., U.S. Pat. No. 9,399,766 and references therein.

In addition to wild-type polymerases, chimeric polymerases made from a mosaic of different sources can be used. For example, Φ29 polymerases made by taking sequences from more than one parental polymerase into account can be used in methods described herein. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. For example, polymerases have been modified to confer improvements in specificity, processivity, and improved retention time of labeled nucleotides in polymerase-DNA-nucleotide complexes (e.g., WO 2007/076057 Polymerases For Nucleotide Analogue Incorporation by Hanzel et al. and WO 2008/051530 Polymerase Enzymes And Reagents For Enhanced Nucleic Acid Sequencing by Rank et al.), to alter branch fraction and translocation (e.g., US Pub. No. 20100075332 entitled "Engineering Polymerases And Reaction Conditions For Modified Incorporation Properties"), to increase photostability (e.g., US Pub. No. 20100093555 entitled "Enzymes Resistant to Photodamage"), and to improve surface-immobilized enzyme activities (e.g., WO 2007/075987 Active Surface Coupled Polymerases by Hanzel et al. and WO 2007/076057 Protein Engineering Strategies To Optimize Activity Of Surface Attached Proteins by Hanzel et al.). In some cases, the polymerase is modified in order to more effectively incorporate desired nucleotide analogs, e.g. analogs having four or more phosphates in their polyphosphate chain. Enzymes mutated to more readily accept nucleotide analogs having such properties are described, for example in the applications described above and in US 20120034602—Recombinant Polymerases for Improved Single Molecule Sequencing; US 20100093555—Enzymes Resistant to Photodamage; US 20110189659—Generation of Modified Polymerases for Improved Accuracy in Single Molecule Sequencing; US 20100112645—Generation of Modified Polymerases for Improved Accuracy in Single Molecule Sequencing; US 2008/0108082—Polymerase enzymes and reagents for enhanced nucleic acid sequencing; and US 20110059505—Polymerases for Nucleotide Analogue Incorporation. Each of these references is incorporated herein by reference in its entirety for all purposes.

Many polymerases that are suitable, e.g., for use in sequencing, labeling and amplification technologies, are available. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot) com provides comparisons of many different commercially available polymerases.

DNA polymerases that can be employed, e.g., in single molecule sequencing or other techniques of use with methods and compositions of the invention, include, e.g., Taq polymerases, exonuclease deficient Taq polymerases, $E.\ coli$ DNA Polymerase 1, Klenow fragment, reverse transcriptases, Φ29-related polymerases including wild type Φ29 polymerase and derivatives of such polymerases such as exonuclease deficient forms, T7 DNA polymerase, T5 DNA polymerase, an RB69 polymerase, etc.

In one aspect, the polymerase of use in the methods and compositions described herein is a modified Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. Alternately, the modified recombinant DNA polymerase can be homologous to other Φ29-type DNA polymerases, such as B103, GA-1, PZA, 015, BS32, M2Y, Nf, G1, Cp-1, PRD1, PZE, SFS, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Suitable polymerases (including polymerases with two biotinylation sites that constitute a bis-biotin tag) are described, for example, in U.S. Patent application publications 2007-0196846, 2008-0108082, 2010-0075332, 2010-0093555, 2010-0112645, 2011-0189659, 2012-0034602, 2013-0217007, 2014-0094374, and 2014-0094375, each of which is incorporated herein by reference in its entirety for all purposes.

In some embodiments, the polymerase enzyme used in the methods described herein includes RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

To reduce or prevent undesired dissociation of the polymerase from the template and primer, the processivity of the polymerase can be increased by locking the template in place in the enzyme, e.g., with chemical cross-links. For example, a bifunctional cross-linker can be reacted with residues in the polymerase on each side of the bound template, topologically encircling the template. See, e.g., U.S. Pat. No. 7,745,116 and US patent application publication 2015/0086994, each of which is incorporated herein by reference in its entirety for all purposes. Cysteine residues can be introduced into the polymerase at suitable positions for cross-link formation. For example, a recombinant Φ29 polymerase can include, e.g., A83C and E420C substitutions, D84C and E418C substitutions, V19C and N409C substitutions, and/or N409C and V568C substitutions. (See, e.g., US patent application publication 2014/0094375, incorporated herein by reference in its entirety for all purposes, for the sequence of wild-type Φ29 polymerase.) Existing solvent accessible cysteine residues can be mutated to ensure that the cross-link is formed between the desired pair of residues; thus, a suitable recombinant Φ29 polymerase can also include one or more substitutions such as, e.g., C106S and/or C448V. Suitable bifunctional linkers are known in the art, for example, a bismaleimide linker, e.g., a bismaleimide-PEG linker, e.g., 1,11-bismaleimido-triethyleneglycol (BM(PEG)$_3$). Other coupling chemistries that can be employed include, e.g., thiol reactive reagents and disulfide containing reagents, e.g., haloacetyl crosslinkers (e.g., linkers including two iodoacetyl/iodoacetamide or bromoacetyl groups) and linkers with two pyridyl disulfide groups. The body of the linker can include, e.g., PEG (polyethylene glycol), an oligopeptide (e.g., polyglycine), or the like. Optimal linker length can be chosen based on the distance between the two residues to be cross-linked, e.g., in a crystal structure or other model of the polymerase. The linker is typically reacted with the polymerase after binding of the template (or primer/template); suitable reaction conditions for various linker chemistries are known in the art. Noncovalent linkers can also be employed. Such topological encirclement of the template by polymerase can be particularly effective for circular templates (including, e.g., simple circles and SMRTbells™ (circular nucleic acids having a double-stranded central region and single-stranded hairpin ends) as described in, e.g., U.S. Pat. No. 8,153,375 "Compositions and Methods for Nucleic Acid Sequencing" and Travers et al. (2010) Nucl. Acids Res. 38(15):e159, each of which is incorporated herein by reference in its entirety for all purposes).

Many native DNA polymerases have a proof-reading exonuclease function which can yield substantial data analysis problems in processes that utilize real time observation of incorporation events as a method of identifying sequence information, e.g., single molecule sequencing applications. Even where exonuclease activity does not introduce such problems in single molecule sequencing, reduction of exonuclease activity can be desirable since it can increase accuracy (in some cases at the expense of readlength).

Accordingly, polymerases for use in the above techniques optionally include one or more mutations (e.g., substitutions, insertions, and/or deletions) relative to the parental polymerase that reduce or eliminate endogenous exonuclease activity. For example, relative to wild-type Φ29 DNA polymerase, one or more of positions N62, D12, E14, T15, H61, D66, D169, K143, Y148, and H149 is optionally mutated to reduce exonuclease activity in a recombinant Φ29 polymerase. Exemplary mutations that can reduce exonuclease activity in a recombinant Φ29 polymerase include, e.g., N62D, N62H, D12A, T151, E141, E14A, D66A, K143D, D145A and D169A substitutions, as well as addition of an exogenous feature at the C-terminus (e.g., a polyhistidine tag). See, e.g., US patent application publication 2014/0094375, incorporated herein by reference in its entirety for all purposes, for the sequence of wild-type Φ29 polymerase.

VII. Applications for Methods and Compositions of the Invention: Sequencing

The methods, devices, systems, and compositions of the invention are particularly useful for loading arrays that can then be used, e.g., in single molecule sequencing methods, and specifically single molecule sequencing by incorporation in real time or by nanopore sequencing, because the methods and compositions of the present disclosure provide a way to load a desired number of reaction regions with a composition such as a nucleic acid or a reaction complex that includes a polymerase complexed to a template nucleic acid. In general, the loading achieved by methods and compositions described herein allow single molecule analysis to be conducted more efficiently and with greater speed, because there will be a decreased need for the use of multiple substrates to assess loading, and because the result of the ability to load a predetermined number of reaction regions (also referred to herein as "reaction sites") will result in fewer "unusable" regions on a substrate surface. ("Unusable" regions on a substrate for a sequencing reaction would be regions that have no or multiple polymerase compositions loaded, which provide either no information (for the empty regions) or sequencing information that must be deconvoluted to be useful (to account for the multiply loaded molecules).)

In some aspects, the present invention includes methods of analyzing the sequence of template nucleic acids. In such aspects, the sequence analysis optionally employs template dependent synthesis in identifying the nucleotide sequence of the template nucleic acid. Nucleic acid sequence analysis that employs template dependent synthesis identifies individual bases, or groups of bases, as they are added during a template mediated synthesis reaction, such as a primer extension reaction, where the identity of the base is required to be complementary to the template sequence to which the primer sequence is hybridized during synthesis. Other such processes include ligation driven processes, where oligo- or polynucleotides are complexed with an underlying template sequence, in order to identify the sequence of nucleotides in that sequence. Typically, such processes are enzymatically mediated using nucleic acid polymerases, such as DNA polymerases, RNA polymerases, reverse transcriptases, and the like, or other enzymes such as in the case of ligation driven processes, e.g., ligases.

Sequence analysis using template dependent synthesis can include a number of different processes. For example, in embodiments utilizing sequence by synthesis processes, individual nucleotides or nucleotide analogs are identified iteratively as they are added to the growing primer extension product.

For sequencing processes that rely upon monitoring of the incorporation of nucleotides into growing nascent strands being synthesized by the complex, the progress of the reaction through these steps can be of significant importance. In particular, for certain real-time nucleotide incorporation monitoring processes, the detectability of the incorporation event is improved based upon the amount of time the nucleotide is incorporated into and retained within the synthesis complex during its ultimate incorporation into a primer extension product. By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene, et al. (2003) Science 299:682-686 and Eid, J. et al. (2009) Science, 323(5910):133-138, the full disclosures of which are incorporated herein by reference in their entirety for all purposes.

In some aspects, the methods of the present invention include steps from any single molecule sequencing methods known in the art. See, e.g., Rigler, et al., DNA-Sequencing at the Single Molecule Level, Journal of Biotechnology, 86(3): 161 (2001); Goodwin, P. M., et al., Application of Single Molecule Detection to DNA Sequencing. Nucleosides & Nucleotides, 16(5-6): 543-550 (1997); Howorka, S., et al., Sequence-Specific Detection of Individual DNA Strands using Engineered Nanopores, Nature Biotechnology, 19(7): 636-639 (2001); Meller, A., et al., Rapid Nanopore Discrimination Between Single Polynucleotide Molecules, Proceedings of the National Academy of Sciences of the United States of America, 97(3): 1079-1084 (2000); Driscoll, R. J., et al., Atomic-Scale Imaging of DNA Using Scanning Tunneling Microscopy. Nature, 346(6281): 294-296 (1990).

In some embodiments, methods of single molecule sequencing known in the art include detecting individual nucleotides as they are incorporated into a primed template, i.e., sequencing by synthesis. Such methods can utilize exonucleases to sequentially release individual fluorescently labeled bases as a second step after DNA polymerase has formed a complete complementary strand. See Goodwin et al., "Application of Single Molecule Detection to DNA Sequencing," Nucleos. Nucleot. 16: 543-550 (1997).

In general, for sequencing methods utilizing compositions of the present invention, individual polymerase compositions are provided within separate discrete regions of a support. For example, in some cases, individual complexes may be provided within individual confinement structures, including nanoscale structures such as nanoscale wells. In some examples, zero-mode waveguide cores or any of the reaction regions discussed above in the stepwise sequencing section serve as the reaction regions for sequencing methods utilizing compositions of the present invention. Examples of waveguides and processes for immobilizing individual complexes therein are described in, e.g., Published International Patent Application No. WO 2007/123763, the full disclosure of which is incorporated herein by reference in its entirety for all purposes and in particular for all teachings related to providing individual complexes into individual confinement structures. In some cases the molecules of interest (e.g., polymerase/template complexes) can be provided onto or proximal to structures or regions that allow for electronic single molecule sequencing. Such structures can include nanoscale electronic structures such as electrodes, capacitors, or field effect transducers (nanoFETs). NanoFETs include those having carbon nanotube gates. Such structures and their use for single molecule sequencing are described, for example, in U.S. Patent Application Publication Nos. 2015/0065353 and 2017/0037462, which are incorporated herein in their entirety for all purposes and in particular for all teachings related to structures for use in single molecule sequencing.

Incorporation of labeled nucleotide analogs by polymerases is particularly useful in a variety of different nucleic acid analyses, including real-time monitoring of DNA polymerization. The label can itself be incorporated, or more preferably, can be released during incorporation of the analog. For example, analog incorporation can be monitored in real time by monitoring label release during incorporation of the analog by the polymerase. The portion of the analog that is incorporated can be the same as a natural nucleotide, or can include features of the analog that differ from a natural nucleotide.

In general, label incorporation or release can be used to indicate the presence and composition of a growing nucleic acid strand, e.g., providing evidence of template replication/amplification and/or sequence of the template. Signaling from the incorporation can be the result of detecting labeling groups that are liberated from the incorporated analog, e.g., in a solid phase assay, or can arise upon the incorporation reaction. For example, in the case of FRET labels where a bound label is quenched and a free label is not, release of a label group from the incorporated analog can give rise to a fluorescent signal. Alternatively, the enzyme may be labeled with one member of a FRET pair proximal to the active site, and incorporation of an analog bearing the other member will allow energy transfer upon incorporation. The use of enzyme bound FRET components in nucleic acid sequencing applications is described, e.g., in U.S. Patent Application Publication No. 2003/0044781, incorporated herein by reference.

In one example reaction of interest, a polymerase reaction can be isolated within an extremely small observation volume that effectively results in observation of individual polymerase molecules. As a result, the incorporation event provides observation of an incorporating nucleotide analog that is readily distinguishable from non-incorporated nucleotide analogs. In a preferred aspect, such small observation volumes are provided by immobilizing the polymerase enzyme within an optical confinement, such as a Zero Mode Waveguide (ZMW). For a description of ZMWs and their application in single molecule analyses, and particularly nucleic acid sequencing, see, e.g., U.S. Patent Application Publication No. 2003/0044781 and U.S. Pat. No. 6,917,726, each of which is incorporated herein by reference in its entirety for all purposes. See also Levene et al. (2003) "Zero-mode waveguides for single-molecule analysis at high concentrations" Science 299:682-686, Eid et al. (2009) "Real-time DNA sequencing from single polymerase molecules" Science 323:133-138, and U.S. Pat. Nos. 7,056,676, 7,056,661, 7,052,847, and 7,033,764, the full disclosures of which are incorporated herein by reference in their entirety for all purposes.

In general, a polymerase enzyme is complexed with the template strand in the presence of one or more nucleotides and/or one or more nucleotide analogs. For example, in certain embodiments, labeled analogs are present representing analogous compounds to each of the four natural nucleotides, A, T, G and C, e.g., in separate polymerase reactions, as in classical Sanger sequencing, or multiplexed together, e.g., in a single reaction, as in multiplexed sequencing approaches. When a particular base in the template strand is encountered by the polymerase during the polymerization reaction, it complexes with an available analog that is complementary to such nucleotide, and incorporates that analog into the nascent and growing nucleic acid strand. In one aspect, incorporation can result in a label being released, e.g., in polyphosphate analogs, cleaving between the a and 13 phosphorus atoms in the analog, and consequently releasing the labeling group (or a portion thereof). The incorporation event is detected, either by virtue of a longer presence of the analog and, thus, the label, in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a zero mode waveguide. For additional information on single molecule sequencing monitoring incorporation of phosphate-labeled analogs in real time, see, e.g., Eid et al. (2009) "Real-time DNA sequencing from single polymerase molecules" Science 323:133-138.

In a first exemplary technique, a nucleic acid synthesis complex including a polymerase enzyme, a template sequence and a complementary primer sequence is provided immobilized within an observation region that permits illumination and observation of a small volume that includes the complex without excessive illumination of the surrounding volume. By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume. In particular, when a nucleotide is incorporated into DNA by the polymerase, it is retained within the observation volume for a prolonged period of time, and upon continued illumination yields a prolonged fluorescent signal. By comparison, randomly diffusing and not incorporated nucleotides remain within the observation volume for much shorter periods of time, and thus produce only transient signals, many of which go undetected due to their extremely short duration.

In particularly preferred exemplary systems, the confined illumination volume is provided through the use of arrays of optically confined apertures termed zero mode waveguides (ZMWs). See, e.g., U.S. Pat. No. 6,917,726, which is incorporated herein by reference in its entirety for all purposes. For sequencing applications, the DNA polymerase is typically provided immobilized upon the bottom of the ZMW, although another component of the complex (e.g., a primer or template) is optionally immobilized on the bottom of the ZMW to localize the complex. See, e.g., Korlach et al. (2008) PNAS U.S.A. 105(4):1176-1181 and US patent application publication 2008-0032301, each of which is incorporated herein by reference in its entirety for all purposes.

In operation, the fluorescently labeled nucleotides (e.g., analogs corresponding to A, C, G and T) bear one or more fluorescent dye groups on a terminal phosphate moiety that is cleaved from the nucleotide upon incorporation. As a result, synthesized nucleic acids do not bear the build-up of fluorescent labels, as the labeled polyphosphate groups diffuse away from the complex following incorporation of the associated nucleotide, nor do such labels interfere with the incorporation event. See, e.g., Korlach et al. (2008) Nucleosides, Nucleotides and Nucleic Acids 27:1072-1083.

In a second exemplary technique, the immobilized complex and the nucleotides to be incorporated are each provided with interactive labeling components. Upon incorporation, the nucleotide borne labeling component is brought into sufficient proximity to the complex borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal quenching. Upon incorporation and cleavage of the terminal phosphate groups, e.g., bearing a donor fluorophore, the quenching is removed and the resulting characteristic fluorescent signal of the donor is observable.

In exploiting the foregoing processes, where the incorporation reaction occurs too rapidly, it may result in the incorporation event not being detected, i.e., the event speed exceeds the detection speed of the monitoring system. The missed detection of incorporated nucleotides can lead to an increased rate of errors in sequence determination, as omissions in the real sequence. In order to mitigate the potential for missed pulses due to short reaction or product release times, in one aspect, the current invention can result in increased reaction and/or product release times during incorporation cycles. Similarly, very short interpulse distances can occasionally cause pulse merging. An advantage of employing polymerases with reduced reaction rates, e.g., polymerases exhibiting decreased rates and/or two slow-step kinetics as described in US patent application publications 2009-0286245 and 2010-0112645, is an increased frequency of longer, detectable, binding events. This advantage may also be seen as an increased ratio of longer, detectable pulses to shorter, non-detectable pulses, where the pulses represent binding events.

The sequencing processes, e.g., using the substrates described above and the compositions of the invention, are generally exploited in the context of a fluorescence optical system that is capable of illuminating the various complexes on the substrate, and obtaining, detecting and separately recording fluorescent signals from these complexes. Such systems typically employ one or more illumination sources that provide excitation light of appropriate wavelength(s) for the labels being used. An optical train directs the excitation light at the reaction region(s) and collects emitted fluorescent signals and directs them to an appropriate detector or detectors. Additional components of the optical train can provide for separation of spectrally different signals, e.g., from different fluorescent labels, and direction of these separated signals to different portions of a single detector or to different detectors. Other components may provide for spatial filtering of optical signals, focusing and direction of the excitation and or emission light to and from the substrate. An exemplary system is also described in U.S. Patent Application publication no. 2007-0036511 and Lundquist et al. (2008) Optics Letters 33(9):1026-1028, the full disclosures of which are incorporated herein by reference in their entirety for all purposes. Fluorescence reflective optical trains can be used in the applications of the systems of the invention. For a discussion on the advantages of such systems, see, e.g., U.S. patent application Ser. No. 11/704,689, filed Feb. 9, 2007, Ser. No. 11/483,413, filed Jul. 7, 2006, and Ser. No. 11/704,733, filed Feb. 9, 2007, the full disclosures of which are incorporated herein by reference in their entirety for all purposes.

In the context of the nucleic acid sequencing methods described herein, it will be appreciated that the signal sources each represent sequencing reactions, and particularly, polymerase mediated, template dependent primer extension reactions, where in preferred aspects, each base incorporation event results in a prolonged illumination (or localization) of one of four differentially labeled nucleotides being incorporated, so as to yield a recognizable pulse (peak) that carries a distinguishable spectral profile and/or color. Similar reactions may also be used to detect the presence of polymerase enzyme complexes within the nanoscale wells in accordance with the loading methods described above.

In other embodiments, the reaction sites into which molecules of interest are loaded are nanopores. As will be appreciated, any of the loading methods described herein with respect to loading of arrays of nanoscale wells applies equally to nanopores. In exemplary embodiments, polymerase enzyme complexes are loaded into a nanopore—the nanopore comprises binding moieties complementary to reaction moieties on the enzyme (or another molecule associated with the enzyme, e.g., a template). In this way, a single enzyme complex is loaded into each of a plurality of nanopores. In certain embodiments, the complexes are attached proximal to the nanopore. As will be appreciated, helicases, exonucleases, and/or other motor proteins can be used in addition to or instead of polymerases in nanopore sequencing and can be loaded by the techniques described herein. Complexes of these enzymes with nucleic acids can be loaded to nanopores as detailed herein, and the nucleic acid or enzyme component of the complex can be attached to or proximal to the nanopore. The nucleotide sequence of the nucleic acid can be determined as the nucleic acid traverses the nanopore. Methods of single molecule nanopore sequencing are known in the art and disclosed for example in US patent application publication nos. 2013/0327644 and 2014/0051068, which are hereby incorporated by reference for all purposes and in particular for all teachings, written description, figures, and figure legends related to nanopore sequencing.

The methods described herein can further include computer implemented processes, and/or software incorporated onto a computer readable medium instructing such processes, as set forth in greater detail below. As such, signal data generated by the reactions and optical systems described above is input or otherwise received into a computer or other data processor, and subjected to one or more of the various process steps or components set forth below. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the invention can range from personal computers such as PC or Macintosh® type computers, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

In some cases, the compositions, methods, and systems of the invention can be used as part of an integrated sequencing system, for example, as described in US 20120014837—Illumination of Integrated Analytical Systems, US 20120021525—Optics Collection and Detection System and Method, US 20120019828—Integrated Analytical System and Method, 61/660,776 filed Jun. 17, 2012—Arrays of Integrated Analytical Devices and Methods for Production, and US 20120085894—Substrates and Optical Systems and Methods of Use Thereof which are incorporated herein by reference in their entirety for all purposes. Suitable sequencing systems are commercially available, e.g., from Pacific Biosciences of California.

In certain embodiments, the sequencing compositions described herein will be provided in whole, or in part, in kit form enabling one to carry out the processes described herein. Such kits will typically comprise one or more components of the reaction complex, such as the polymerase enzyme and primer sequences. Such kits will also typically include buffers and reagents for loading of the polymerase and/or a template as in the processes described herein. The kits will also optionally include other components for carrying out sequencing applications in accordance with those methods described herein. In particular, such kits may include ZMW array substrates for use in observing individual reaction complexes as described herein.

In addition to the various components set forth above, the kits will typically include instructions for combining the various components in the amounts and/or ratios set forth herein, to carry out the desired processes, as also described or referenced herein, e.g., for loading polymerase enzyme complexes, immobilizing polymerase enzyme complexes, and/or performing sequence by incorporation reactions.

VIII. Substrates and Surfaces

Substrates of use in the methods described herein are known in the art and discussed herein, and as will be appreciated, any of the substrates discussed herein can be used in any combination for any embodiments discussed herein.

In exemplary embodiments, the loading methods described herein are generally used for loading molecules of interest, including polymerase enzyme complexes, onto substrates that include one or more reaction regions (also referred to herein as "array regions") arranged in the form of an array on an inert substrate material, also referred to herein as a "solid support" or "surface," that allows for combination of the reactants, e.g., in a sequencing reaction, in a defined space. Arrays can be regular or irregular, e.g., random. The substrates and array regions can also allow for detection, e.g., of the sequencing reaction event. As described above, nucleic acids or polymerase complexes can be deposited in the reaction regions such that individual nucleic acids (or polymerase reactions) are independently optically observable. A reaction region can be a localized area on the substrate material that facilitates interaction of reactants, e.g., in a nucleic acid sequencing reaction. A reaction region may in certain embodiments be a nanoscale well (also referred to herein as a nanowell), and in further embodiments the nanowell is a ZMW. A nanoscale well typically has dimensions in the nanometer range, i.e., less than 1 micrometer and more than 1 nanometer. In some embodiments, a nanoscale well has a cross-sectional diameter of less than 1000, 900, 800, 700, 600, or 500 nm, e.g., less than 400, 350, 300, 250, or 200 nm. In some embodiments, a nanoscale well has a depth of less than 1000, 900, 800, 700, 600, or 500 nm, e.g., less than 400, 350, 300, 250, or 200 nm. As discussed herein, the loading and then subsequent sequencing reactions contemplated by the invention can in some embodiments occur on numerous individual nucleic acid samples in tandem, in particular simultaneously sequencing numerous nucleic acid samples, e.g., derived from genomic and chromosomal DNA. The apparatus of the invention can therefore include an array having a sufficient number of array regions/reaction regions to carry out such numerous individual sequencing reactions. In one embodiment, the array comprises at least 1,000 reaction regions. In another embodiment, the array comprises greater than 400,000 reaction regions, preferably between 400,000 and 20,000,000 reaction regions. In a more preferred embodiment, the array comprises between 1,000,000 and 16,000,000 reaction regions, e.g., 1,000,000, 2,000,000, 3,000,000, 4,000,000, 5,000,000, 6,000,000, 7,000,000, 8,000,000, 9,000,000, or 10,000,000 reaction regions.

The reaction regions on the array may take the form of a cavity or well in the substrate material, having a width and depth, into which reactants can be deposited. One or more of the reactants typically are bound to the substrate material in the reaction region and the remainder of the reactants are in a medium which facilitates the reaction and which flows through or contacts the reaction region. When formed as cavities or wells, the chambers are preferably of sufficient dimension in order to allow for (i) the introduction of the necessary reactants into the chambers, (ii) reactions to take place within the chamber and (iii) inhibition of mixing of reactants between chambers. The shape of the well or cavity is preferably circular or cylindrical, but can be multisided so as to approximate a circular or cylindrical shape. In another embodiment, the shape of the well or cavity is substantially hexagonal. The cavity can have a smooth wall surface. In an additional embodiment, the cavity can have at least one irregular wall surface. The cavities can have, e.g., a planar bottom or a concave bottom.

The reaction regions may in some situations take the form of a nanopore. Such reaction regions, including arrays of nanopores, are known in the art and described for example in US Published App. Nos. 2013/0327644 and 2014/0051068, which are hereby incorporated by reference in their entirety for all purposes and in particular for all teachings related to nanopore arrays.

In general, the reaction regions into which molecules of interest are loaded in accordance with the methods described herein are of a configuration that any signals generated by the molecules of interest are only detectable when those molecules are within the reaction region, e.g., within the nanoscale well (e.g., in an observation volume in the well), within or proximal to the nanopores, or attached to the gate of a nanoFET.

Any material can be used as the solid support material, as long as the surface allows for stable attachment of polymerase enzyme complexes and optionally detection of nucleotide incorporation. The solid support material can be, e.g., planar or cavitated, e.g., in a cavitated terminus of a fiber optic or in a microwell etched, molded, or otherwise micromachined into the planar surface, e.g. using techniques commonly used in the construction of microelectromechanical systems. See e.g., Rai-Choudhury, HANDBOOK OF MICROLITHOGRAPHY, MICROMACHINING, AND MICROFABRICATION, VOLUME 1: MICROLITHOGRAPHY, Volume PM39, SPIE Press (1997); Madou, CRC Press (1997), Aoki, Biotech. Histochem. 67: 98-9 (1992); Kane et al., Biomaterials. 20: 2363-76 (1999); Deng et al., Anal. Chem. 72:3176-80 (2000); Zhu et al., Nat. Genet. 26:283-9 (2000). In some embodiments, the solid support is optically transparent, e.g., glass.

Suitable substrates include chips having arrays of nanoscale wells or zero mode waveguides. Exemplary substrates include substrates having a metal or metal oxide layer on a silica-based layer, with nanoscale wells disposed through the metal or metal layer to or into the silica-based layer. Such substrates are described, for example in U.S. patent application Ser. Nos. 10/259,268, 14/187,198, 14/107,730, 13/920,037, and U.S. Pat. Nos. 8,994,946, 8,906,670, 8,993,307, 8,802,600, 7,907,800, and 7,302,146, which are incorporated herein by reference in their entirety for all purposes and in particular for all teachings related to substrates. Biotinylation of such substrates is described, e.g., in U.S. Pat. Nos. 7,763,423 and 8,802,600 and U.S. patent application publication 2017-0184580 (which are incorporated herein by reference in their entirety for all purposes), as is loading and immobilization of nucleic acids, polymerases, and other molecules on such substrates. Other suitable substrates include, but are not limited to, chips having arrays of nanopores, chips having arrays of wells or apertures that comprise a bilayer in which one or more nanopores are inserted, and chips having arrays of nanoFETS.

IX. Application to Additional Types of Reaction Sites

For simplicity, the methods for establishing molecules of interest in reaction sites have been discussed herein primarily with regard to loading an array of nanoscale wells, particularly an array of zero mode waveguides, with polymerase/nucleic acid complexes using optical detection techniques to monitor loading. As noted above, however, it will be appreciated that any of the methods described herein are applicable to other types of reaction sites, other types of molecules, and/or other detection techniques.

For example, a nanopore array chip can be produced having an array of electrodes within shallow wells. Each of the wells can support a membrane (e.g., a phospholipid bilayer) in which one or more nanopores can be embedded. The electrode at each well is individually addressable, so electrical measurements from each well can be monitored. See, e.g., WO 2009/1077734, WO 2012/042226, and U.S. Patent Application Publication Nos. 2018/0057870, 2013/0244340, 2013/0264207, and 2014/0134616 (which are incorporated herein by reference in their entirety for all purposes). A molecule of interest can be attached to, passed through, or in proximity to a nanopore in the membrane in a well, and electrical measurements from that well can then provide information on the molecule. For example, a nucleic acid/polymerase complex can be attached to the nanopore, and nucleic acid sequence information can be obtained. See, e.g., Fuller et al. (2016) "Real-time single-molecule electronic DNA sequencing by synthesis using polymer-tagged nucleotides on a nanopore array" Proc Natl Acad Sci USA 113:5233-5238, Clarke et al. (2009) "Continuous base identification for single-molecule nanopore DNA sequencing" Nature Nanotechnology 4:265-270, Feng et al. (2015) "Nanopore-based Fourth-generation DNA Sequencing Technology" Genomics, Proteomics & Bioinformatics 13:4-16, U.S. Pat. No. 8,324,914, and WO2012083249, which are incorporated herein by reference in their entirety for all purposes. The wells can be nanoscale wells or microscale wells (having dimensions in the micrometer range, i.e., less than 1 millimeter and more than 1 µm). In other embodiments, arrays of nanoscale or microscale apertures in a solid support, where each of the apertures is individually addressable (e.g., electrically) and capable of supporting a membrane (e.g., a phospholipid bilayer) in which one or more nanopores can be embedded, can be employed. The molecule of interest (e.g., a polymerase, exonuclease, helicase, motor protein, or nucleic acid, including a complex thereof such as a polymerase/nucleic acid or helicase/nucleic acid complex) can be attached to or associated with the nanopore before or after insertion of the nanopore in the membrane.

It will be evident that loading of such well or aperture arrays is subject to similar considerations to loading of zero mode waveguide arrays. For example, it is typically desirable for a single molecule of interest to associate with a single nanopore inside one well or aperture. It is typically also desirable to maximize the number of wells or apertures that are occupied by a single nanopore-associated molecule of interest. The loading methods described herein are thus equally applicable to loading arrays of such wells or apertures.

Essentially all of the features noted above apply to these embodiments as well, as relevant. For example, in one aspect, an array of wells or apertures comprising membranes is provided. A loading solution comprising a molecule of interest (e.g., a polymerase, a helicase, a polymerase/nucleic acid complex, a helicase/nucleic acid complex, a nucleic acid, etc.) is contacted to the surface of the array. In some embodiments, the membranes comprise nanopores, and the molecule of interest associates with the nanopores. In some embodiments, the molecule of interest in the loading solution is associated with a nanopore, and the nanopore inserts into the membrane. (The molecule of interest remains associated.) While the loading solution is in contact with the surface, the array is monitored to detect signals from the wells or apertures to identify wells or apertures that include a nanopore and that have been loaded with a molecule of interest. The loading solution is maintained in contact with the surface until a predetermined number of the wells or apertures have been loaded with a nanopore-associated molecule of interest. In some embodiments, excess molecules of interest are delivered, and some are inactivated until the desired number of wells or apertures contain a single active nanopore-associated molecule of interest. In some embodiments, the molecule of interest is inhibited during or after delivery, and inhibition of a portion of the molecules is relieved to achieve the desired number of wells or apertures containing an active nanopore-associated molecule of interest. In some embodiments, molecules of interest are immobilized or attached to a nanopore through a cleavable linker, and exposure to a cleavage agent is performed until the desired number of wells or apertures contain a nanopore-associated molecule of interest.

The methods are similarly applicable to loading of a molecule of interest onto an array of nanoFET devices (e.g., onto the gate region, e.g., of carbon or other nanotubes), an array of solid-state nanopores (e.g., each having a nanometer range diameter aperture), or an array of other nanoscale or microscale reaction sites.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1: Monitoring During Real-Time Loading of ZMWs

The following sets forth a series of experiments that demonstrate monitoring of loading through cognate sampling during real-time loading of ZMWs.

A loading solution containing a DNA template, primer, and polymerase is prepared. The loading solution also contains a fluorescently labeled dA analog (since the templating base is a T) and unlabeled dT, dC, and dG analogs, along with a noncatalytic divalent cation ($Sr^{2+}$) so the analogs cannot be incorporated by the polymerase. The loading solution also includes an oxygen scavenging system. The sample is dispensed onto a nanoscale well array (a ZMW chip, commercially available from Pacific Biosciences of California). The chip is then transferred to the stage of a Sequel™ sequencing instrument (Pacific Biosciences of California) for data acquisition. A series of short movies are acquired during the loading period to determine how many ZMWs have a DNA/polymerase complex immobilized within. During the loading time, the number of occupied ZMWs is measured until desired loading level is achieved.

Unloaded wells can be distinguished from loaded wells as detailed below. If desired, multiply loaded wells can be distinguished from singly loaded wells by monitoring the level of signal from the wells. For example, the initial signal intensity in a loaded well represents single loading of the well. If additional complexes load into that well, signal intensity increases, so the well is recognizable as being multiply loaded.

Once the desired number of ZMWs are occupied, the chip is removed from the stage and prepared for sequencing. Excess DNA/polymerase is washed off the chip, sequencing solution is added, and the chip is transferred back to the instrument stage for acquisition of a sequencing movie.

Figure 11:
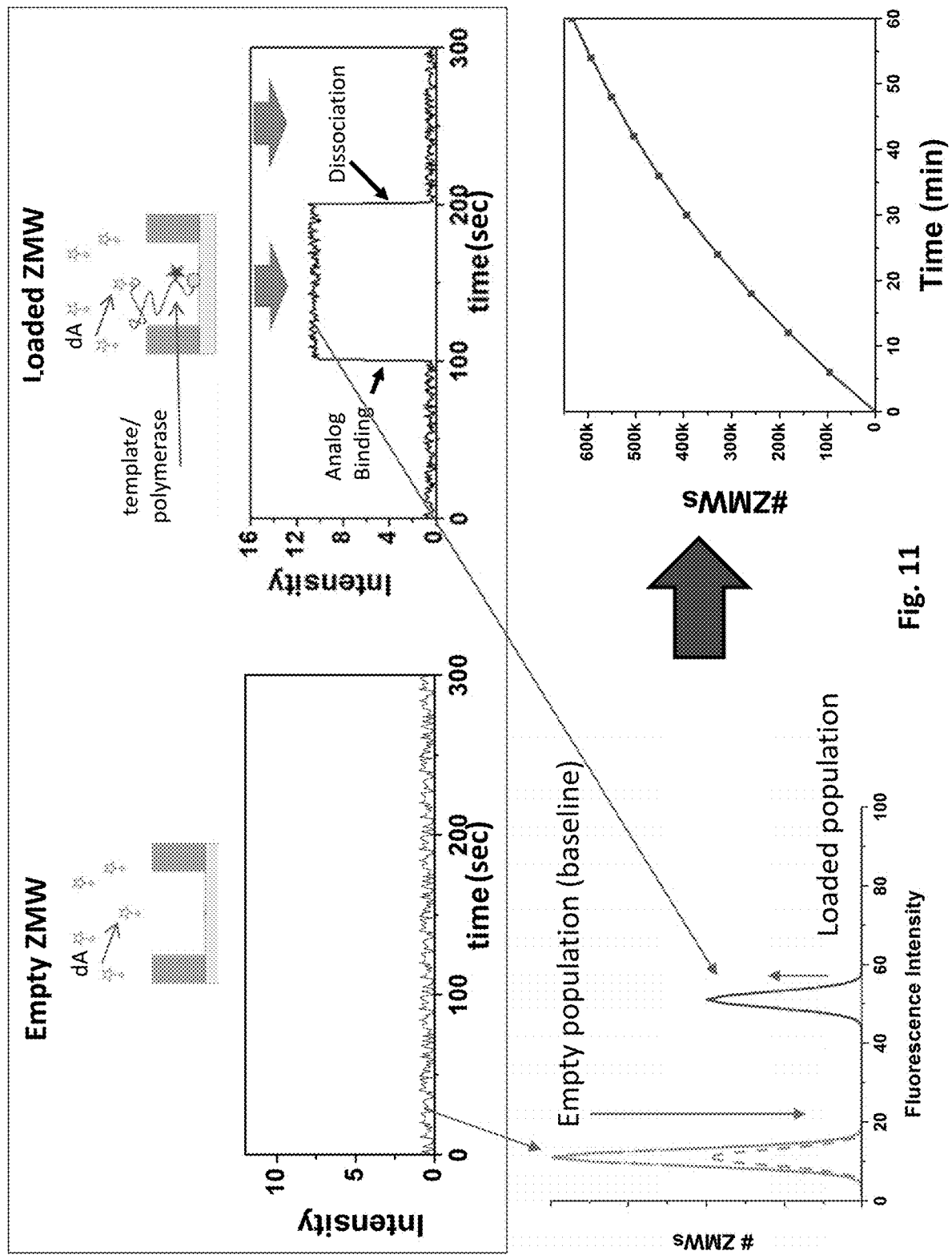
FIG. 11 schematically illustrates how loading of ZMWs can be monitored.

Loading is schematically illustrated in FIG. 11. As shown in the upper left drawing and corresponding fluorescent trace, an empty ZMW can be recognized by the absence of fluorescent signal. As shown in the upper right, when a polymerase/template is immobilized in the observation volume at the bottom of the well, binding of the fluorescently labeled dA analog to the complex produces a strong cognate sampling pulse. As indicated in the graph on the lower left, the population of empty wells (recognizable by the lack of cognate sampling pulses) decreases over time, while the population of loaded wells (recognizable by the presence of cognate sampling pulses) increases over time. The graph on the lower right illustrates the increase in the number of loaded ZMWs over time.

An exemplary trace showing cognate sampling from a loaded well is shown in FIG. 2A. A subsequent sequencing trace from the loaded well is shown in FIG. 2B.

Loading of a 48 kb SMRTbell™ (circular nucleic acid having a double-stranded central region and single-stranded hairpin ends) produced from bacteriophage lambda is shown in FIG. 12. The trace in the upper left shows an empty ZMW, with a baseline at ~5 counts, while the trace in the upper right shows a loaded ZMW, with an average intensity at ~40 counts (fluorescence channel two is being monitored). The graph on the lower left shows the decrease in the population of empty wells and the increase in the population of loaded wells over time (where different lines represent four different time points from 0 to 60 minutes). A portion of the graph is enlarged and shown on the lower right. 32,000 ZMWs spread evenly across the active area of the chip were selected as the region of interest (ROI) for monitoring.

Figure 13:
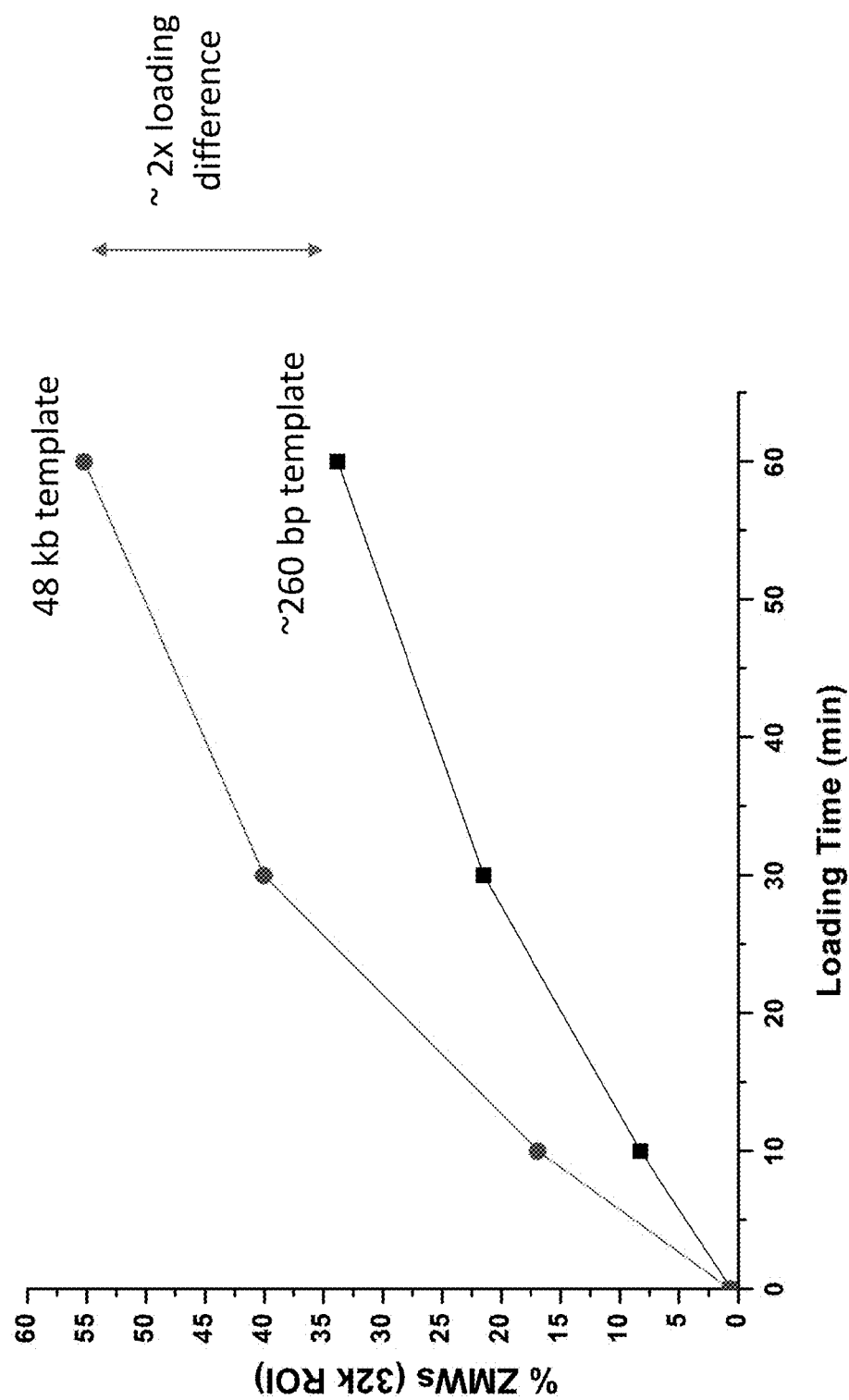
FIG. 13 compares loading of 48 kb and 260 bp templates.

A comparison of the loading efficiency of two different templates is shown in FIG. 13. At various time points, a 48 kb SMRTbell™ (circular nucleic acid having a double-stranded central region and single-stranded hairpin ends) produced from bacteriophage lambda is loaded into about twice as many wells as is an ≈260 bp defined sequence template. Loading time of the smaller template can thus be extended (compared to that for the longer template) to achieve the desired degree of loading.

In the experiments above, loaded levels are monitored at intervals throughout the entire loading period. However, loading can instead be monitored at one or a few initial time points and the time needed to achieve the desired level of loading can be predicted, rendering monitoring throughout the loading period unnecessary.

Figure 19:
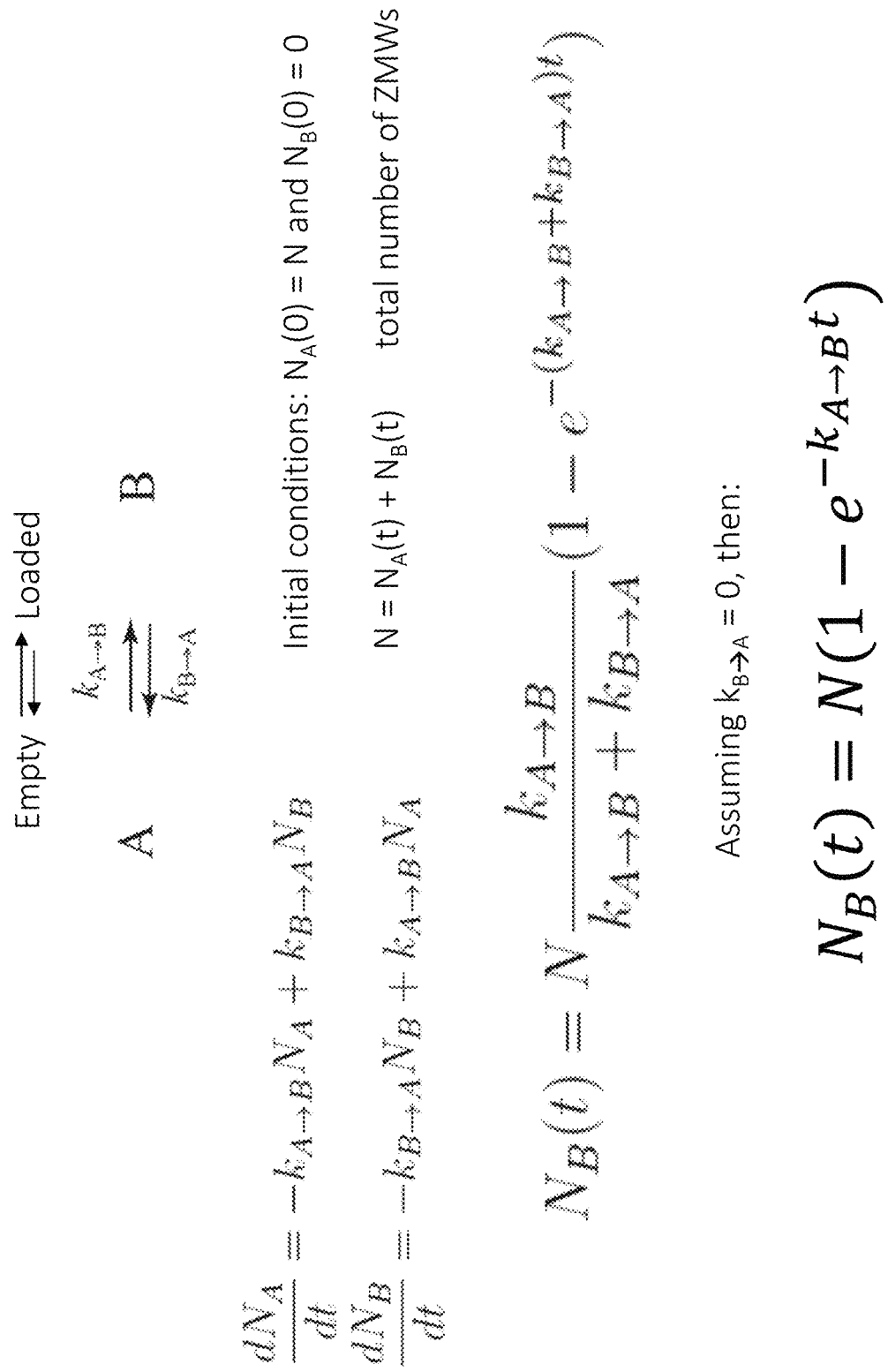
FIG. 19 depicts a mathematical model for predicting the number of loaded reaction sites.

A mathematical model for determination of loading levels at any point in time by monitoring, e.g., only the first few minutes of loading is presented in FIG. 19. A two-state model for ZMWs, loaded and unloaded, is assumed, with association and dissociation rate constants for loading and unloading. This model assumes first order rate kinetics. From the rate equations and initial conditions, an expression for the number of loaded ZMWs at any time t can be derived. Given that no unloading is expected to occur during the immobilization period, the unloading rate constant is assumed to be equal to zero. The expression then reduces to $N_{loaded}(t) = N(1 - e^{-k/(loading) \, t})$ (FIG. 19). With this expression and an assessment of initial loading levels, how much time a user needs to wait to achieve a particular application-dependent loaded state can be determined. (For example, high loading can be targeted for high throughput applications, or lower loading can be targeted for longer read length applications.)

Figure 20A:
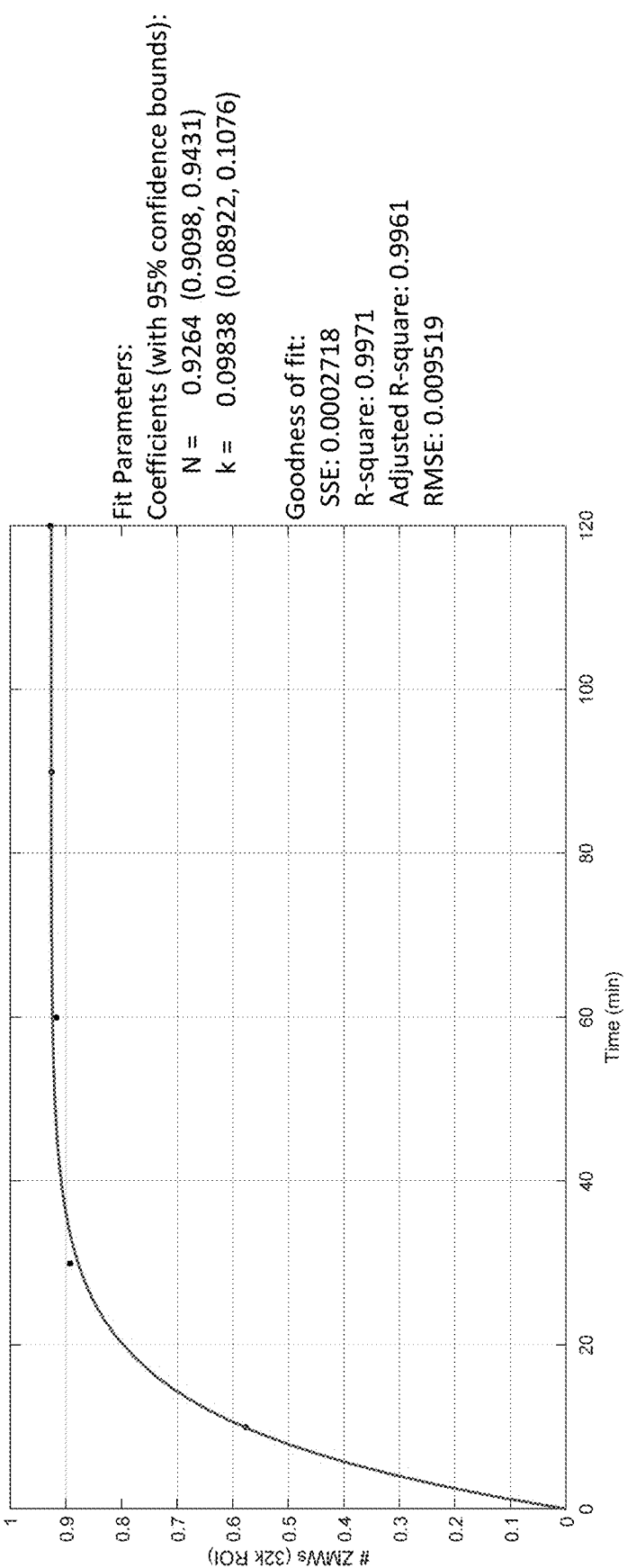
FIG. 20A illustrates use of the mathematical model to fit initial loading data and predict final loading level.
Figure 20B:
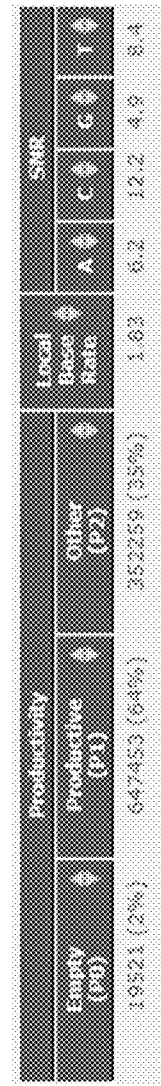
FIG. 20B shows final loading level as measured by sequencing.

Proof of concept experiments show that the model can fit the data very well given data points across the whole immobilization period. A 2 kb template is loaded on a ZMW chip for two hours, with real time monitoring every 30 minutes using cognate sampling as detailed above. Results are shown in FIGS. 20A-B. In FIG. 20A, dots are measured data, and the line is the fit to the model. The model predicts a final loaded state of ~93%. Dashboard metrics when sequencing is performed on a Sequel™ sequencing instrument (Pacific Biosciences of California) after the two hour loading period show a final yield of ~98% (FIG. 20B). The difference in predicted and observed loading percent may be due to errors in P0 vs P2 metrics (for example, if during sequencing an unloaded ZMW is assigned to P2 because it displays a high background signal rather than to P0 as empty) or to differences in observed region of interest for loading assessment (in FIG. 20A, the model is applied to 32,000 ZMWs, while sequencing results in FIG. 20B are for the entire 1 million ZMWs on the chip).

Figure 21A:
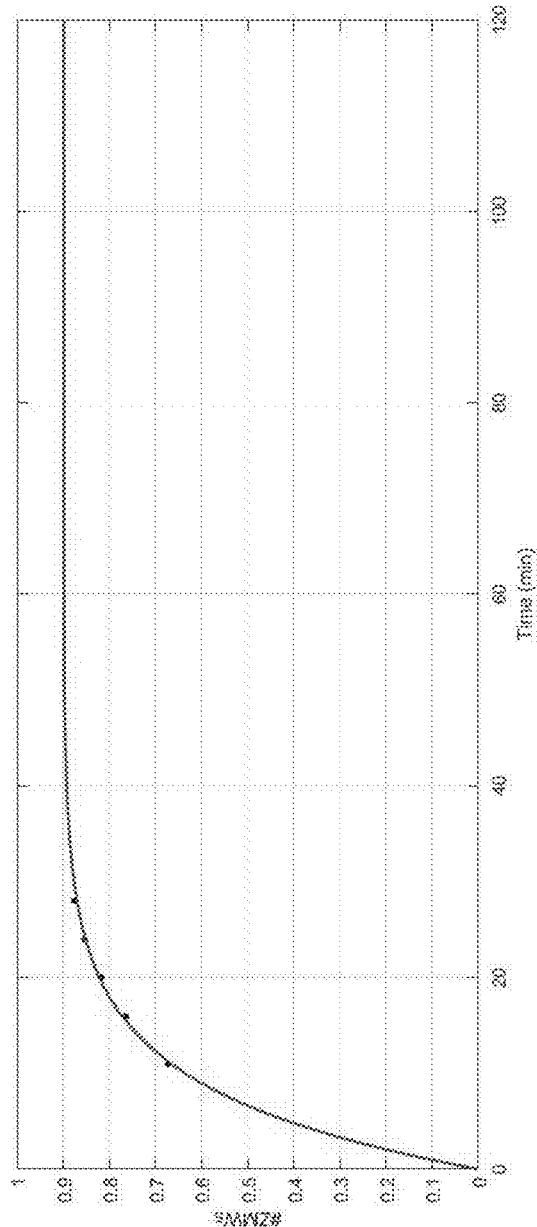
FIG. 21A illustrates use of the mathematical model to fit initial loading data and predict final loading level.
Figure 21B:
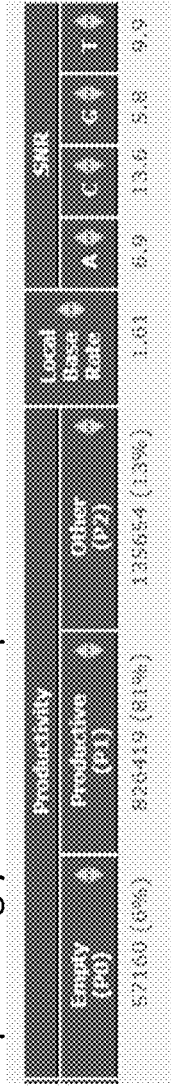
FIG. 21B shows final loading level as measured by sequencing.

Applying the model to the full 1 million ZMWs and collecting data during the first 30 minutes of immobilization also yields a good prediction of total loading. A 2 kb template is loaded on a ZMW chip for two hours, with real time monitoring every 5 minutes using cognate sampling as detailed above. Results are shown in FIGS. 21A-B. In FIG. 21A, dots are measured data, and the line is the fit to the model. The model fits the data very well and predicts (90±3)% total loading after 2 hrs (FIG. 21A). The final P1+P2 metric yielded 94% observed loading (FIG. 21B). With a difference of ~4%, the model is a good predictor for loading. Again, differences in predicted and observed loading may be due to allocation of ZMWs between the P0 and P2 metrics.

Figure 22:
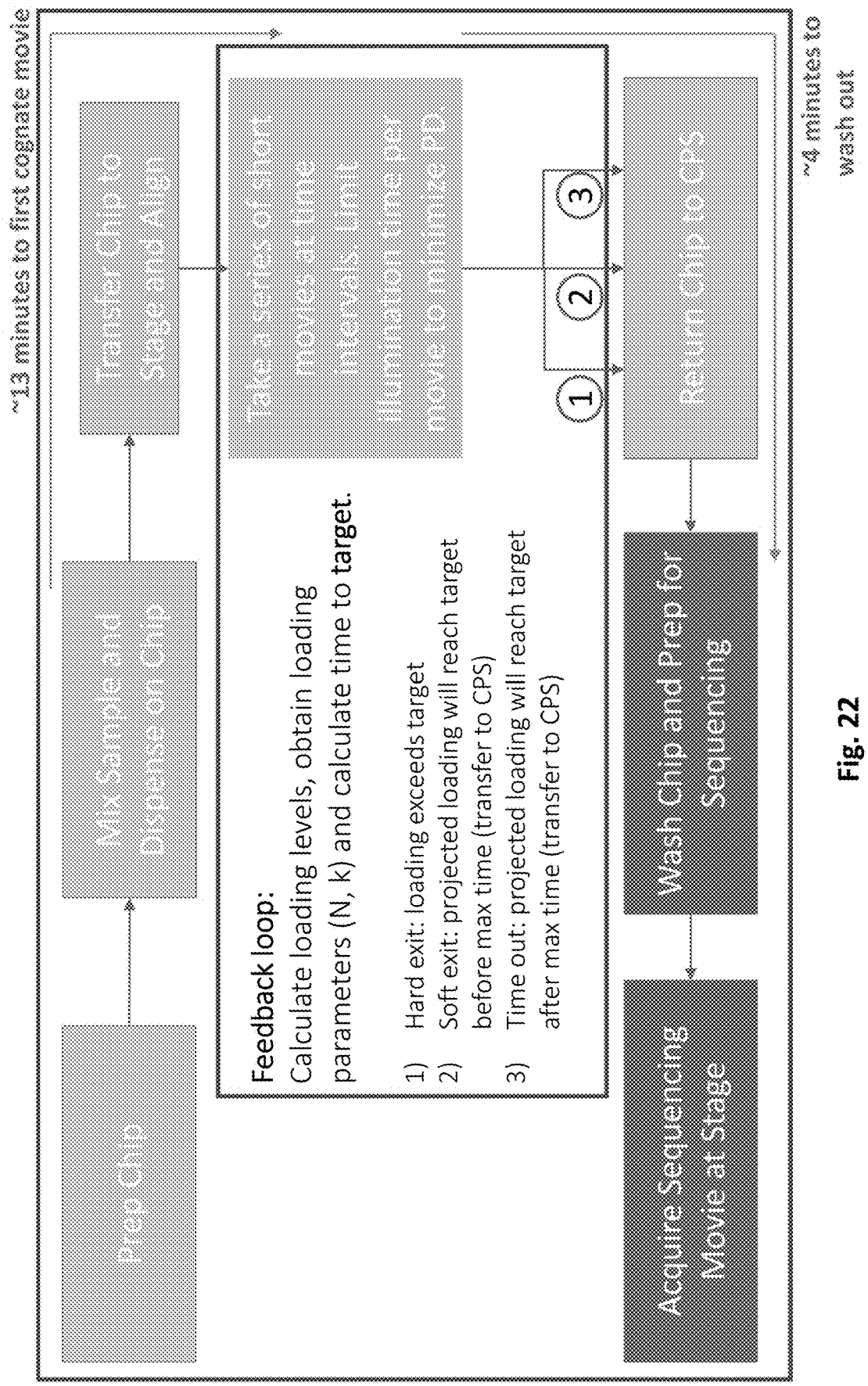
FIG. 22 schematically illustrates an exemplary work flow for software-assisted monitoring of loading in real time and predicting optimum loading end time.

In followup experiments, software is implemented to help automate loading. FIG. 22 schematically illustrates the workflow. A desired loading level is preselected. A ZMW chip is prepared, and the loading solution is prepared (including template, primer, polymerase, a fluorescently labeled cognate analog, a noncatalytic divalent cation ($Sr^{2+}$), etc., as detailed above) and dispensed onto the chip. The chip is transferred to the stage of a Sequel™ or a Sequel II™ sequencing instrument (Pacific Biosciences of California) for data acquisition. A series of short movies are acquired at time intervals (e.g., ten movies three minutes apart); illumination time is limited (e.g., to one second per movie) to minimize photodamage. At each of the time points, the loading level (number or percent of wells occupied, as indicated by detection of cognate sampling signal) is determined. This initial loading data ($N_{loaded}(t)$, loading level at each time point) is fit to the expression $N_{loaded}(t) = N(1 - e^{-k(loading)*(t-t(zero))})$ (FIG. 19) to obtain the loading parameters N and $k_{loading}$, and the time at which the desired preselected loading level will be reached is calculated. Fit is improved by allowing N to float, with a maximum value of 1 (i.e., setting N≤1); without limitation to any particular mechanism, permitting N to hold values less than 1 accounts for situations in which some number of wells are damaged or otherwise unloadable. Fit can also be improved by estimating to (the time before the first cognate movie is collected), e.g., by permitting it to vary by ±5 minutes from the time the loading solution is dispensed onto the chip, to account for variations in time required to mix the loading solution with solution already covering the chip (again without limitation to any particular mechanism). For example, N, $k_{loading}$, and to can be treated as constrained unknowns (e.g., where N is constrained to be less than or equal to 1 and to is constrained to be within +/−5 minutes of the estimated start of loading) and determined by a non-linear constrained least-squares fit to the loading level data (i.e., to $N_{loaded}(t)$, the loading level experimentally determined at each time point t that is monitored).

The software accounts for three general conditions. In some cases, loading proceeds as detailed above, with initial loading measurements being used to obtain N, k, and optionally to and predict the optimal loading time for which the loading solution is maintained in contact with the chip to achieve the desired target loading level (soft exit condition). In cases where the sample concentration is higher than estimated, loading can proceed very rapidly due to the high polymerase enzyme complex concentration; if the observed loading level already exceeds the predetermined target level, the loading process ends immediately (hard exit condition). In applications in which exceeding the predetermined loading level is acceptable, loading can intentionally be performed with a high polymerase enzyme complex concentration, such that hard exit is the most common occurrence; if the initial loading does not exceed the predetermined target, monitoring proceeds and soft exit can occur. In cases where the sample concentration is insufficient to ever achieve the desired target loading level, loading is permitted to continue for a preset maximum time (e.g., two hours), then the loading process ends (time out condition). When any of these three exit conditions is reached, the chip is removed from the stage and prepared for sequencing. Excess DNA/polymerase is washed off the chip, sequencing solution is added, and the chip is transferred back to the instrument stage for acquisition of a sequencing movie.

Figure 23B:
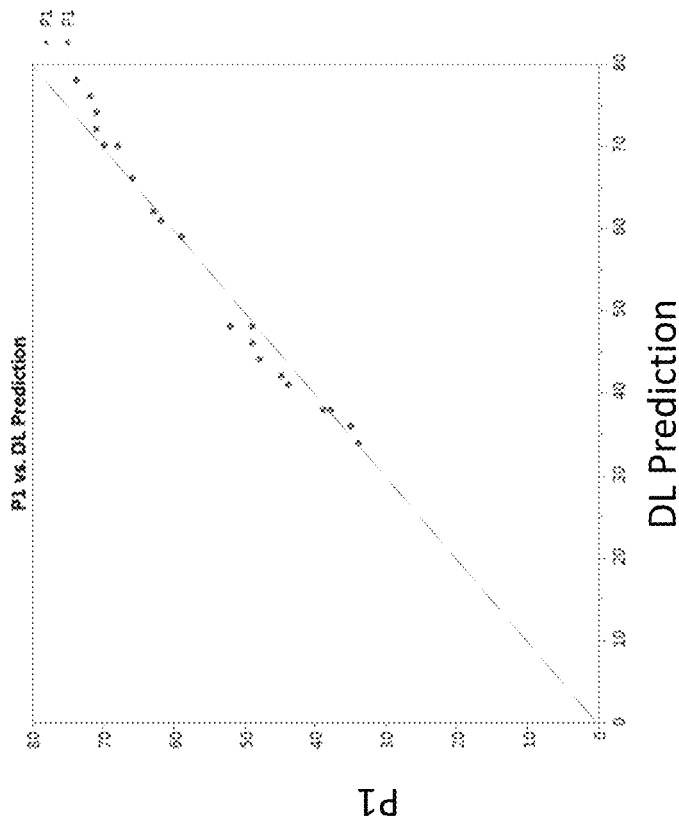
FIGS. 23A-B shows fit of predicted and observed loading levels.
Figure 23A:
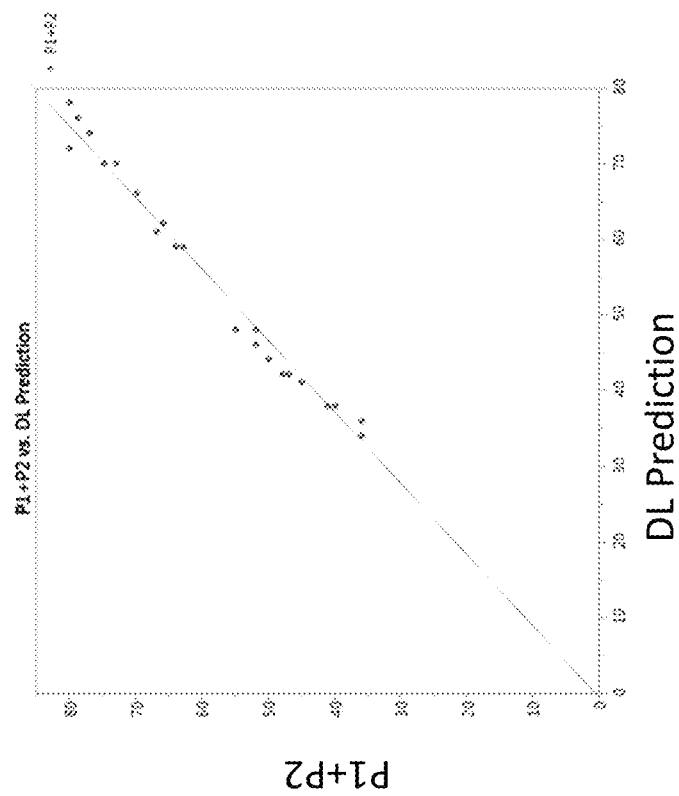

FIGS. 23A-B show how closely the predicted loading level matches the observed loading level for 24 chips loaded with a 10 kb template. FIG. 23A shows the correspondence between predicted loading and the P1+P2 metric, as an estimate of total loading. FIG. 23B shows the correspondence between predicted loading and the P1 metric, representing ZMWs that produce useable sequence data.

Example 2: Use of Laser Pulses to Establish Single Reaction Complexes in ZMWs

Figure 3:
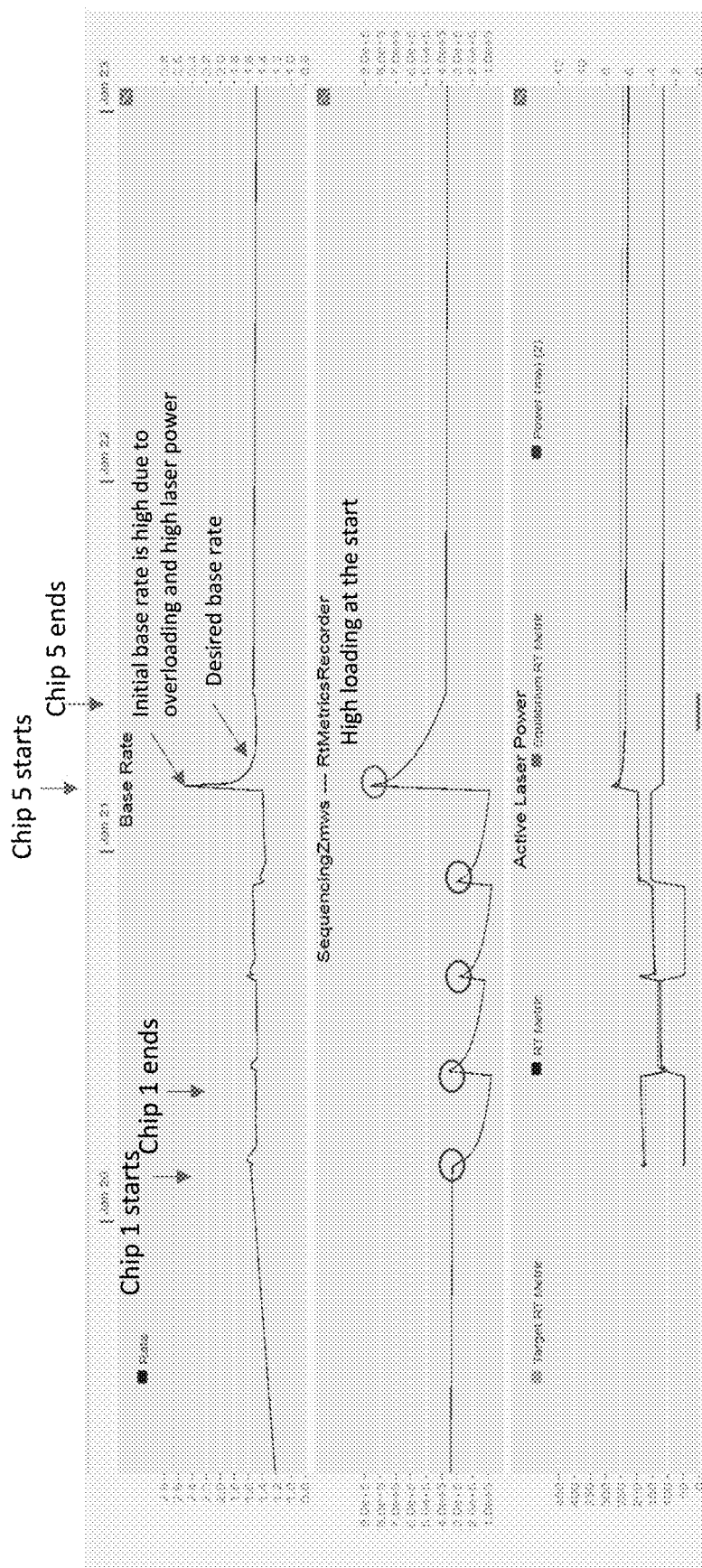
FIG. 3 shows traces indicating the number of occupied nanoscale wells as compared to laser power. The top trace shows base rate, the middle trace shows the estimated occupancy, and the bottom trace shows the adjustments made to active laser power.

Monitoring of base rate, number of sequencing ZMWs, and laser power through five chips each containing an array of ZMWs is demonstrated in FIG. 3. The top trace shows base rate, the middle trace the number of occupied ZMWs, and the bottom trace the laser power. The first four chips are loaded at a low level, with approximately $4 \times 10^5$ ZMWs occupied by at least one active complex (see the four circles on the left in the middle trace of FIG. 3). The fifth chip is loaded at a high level, with about $9 \times 10^5$ ZMWs occupied by at least one complex (see the rightmost circle in the middle trace of FIG. 3). Loading of this array of ZMWs is performed at a concentration of 0.6 fMol, which, based on the configuration of the array and the number of ZMWs, is expected to overload the array with a lambda (average number of active polymerases per well) of 3-4 for this run.

Figure 4:
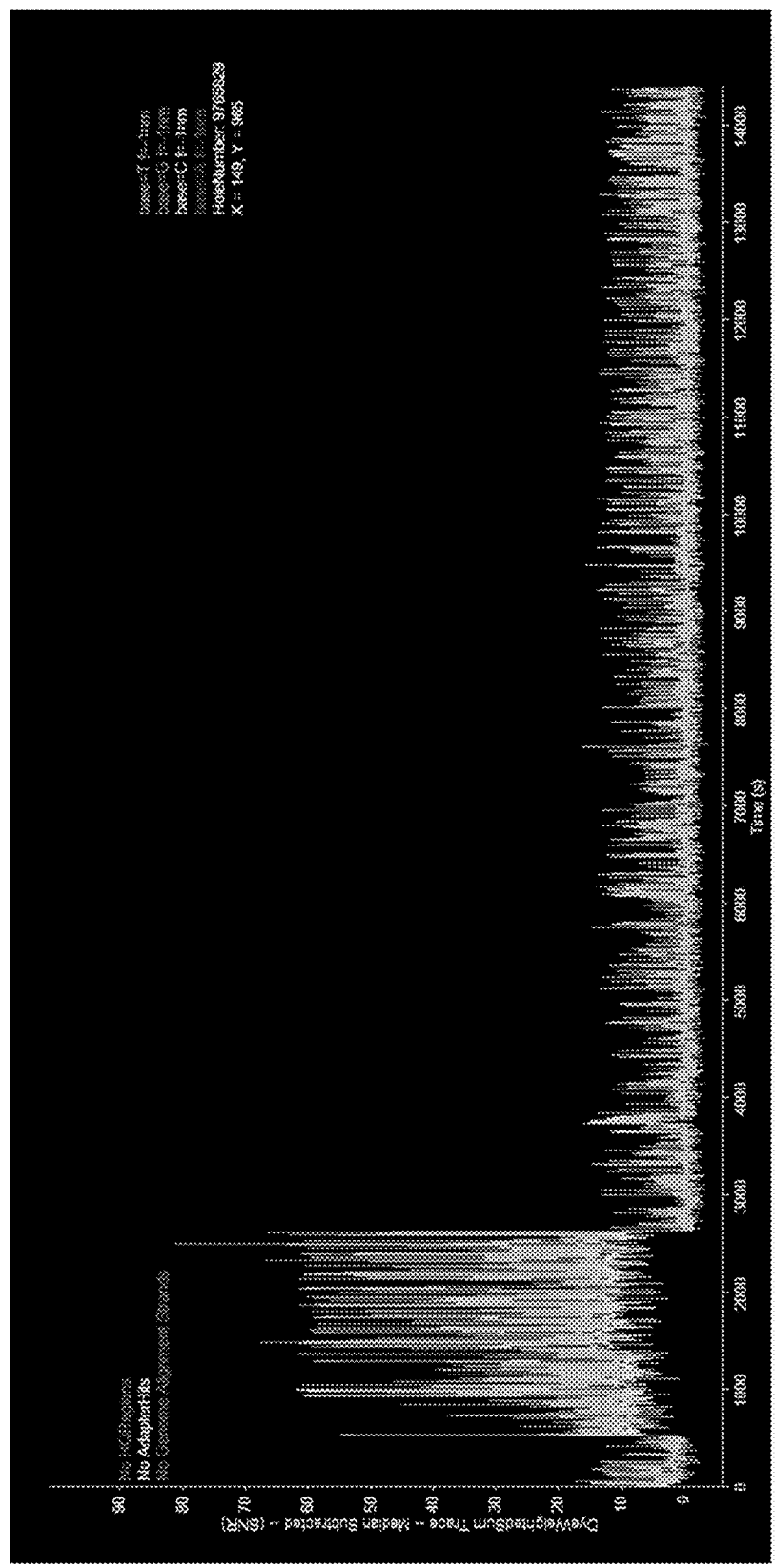
FIG. 4 shows an exemplary trace from a nanoscale well illustrating the transition from multiply to singly occupied resulting from an intense laser pulse.

Once loading is complete, a sequencing reaction is begun (using reagents commercially available from Pacific Biosciences of California) and base rate curve is monitored based on signals generated by the sequencing reactions taking place in the multiply loaded wells at a relatively high laser power of 3 mW. As shown in the top trace of FIG. 3, for the fifth run the initial base rate is high due to the array being overloaded and the high laser power being used, and the initial base rate is higher than in the first four runs. As application of the laser is continued, photodamage to reactants of the sequencing reaction results in inactivation of some of the complexes. Monitoring the base rate curve allows adjustment of the laser power until a base rate is achieved that indicates that a desired number of nanoscale wells are loaded with a single active complex. FIG. 4 shows an exemplary trace from a single ZMW. The initial portion of the trace (until about 2500 sec) is consistent with multiple loading of the ZMW, while the later portion of the trace is consistent with the presence of a single active complex remaining in the ZMW.

Example 3: Inactivating Polymerases by Terminating Chain Extension to Establish Single Reaction Complexes in ZMWs An *E. coli* PCR amplicon sample with size around 5000 bp is converted to SMRTbell™ constructs (circular nucleic acids having a double-stranded central region and single-stranded hairpin ends) and complexed with polymerase as preparation for sequencing on a Sequel™ system from Pacific Biosciences of California, following protocols described in the commercial literature. Loading of an array of ZMWs is performed at a sample concentration of approximately 2-4 times that of normal loading, in the range of 0.5 to 1.0 fmol per chip. Three rounds of signals are collected from the array. A first round of signals provides a preliminary estimate of the level of occupancy of the array. The loading is estimated to be 85-98% in the experiment. The length of time to achieve the desired degree of termination is then calculated based on the loading level. A 6 nM concentration of ddTTP is then spiked into the array. Termination times of 20-75 minutes are applied to reduce the number of active polymerases to the desired level (roughly 1.5 polymerases per ZMW on average). A second round of signals confirms how many ZMWs of the array are occupied by at least one active polymerase enzyme complex after the inactivation by ddTTP. The array is then washed and prepared for sequencing (the third round of signals), for which data was collected in a 10 hour long movie. Through this process, the over-loading is suppressed from 98%+ to about 80%. In addition, readlength improves by 20% as noise from multi-loaded ZMWs is reduced.

Example 4: Reversibly Inhibiting and Reviving Polymerases

One technique for inhibiting a polymerase involves tethering the polyphosphate product of the polymerization reaction to the polymerase. The resulting high effective concentration of polyphosphate is highly inhibitory to polymerase activity.

Figure 16A:
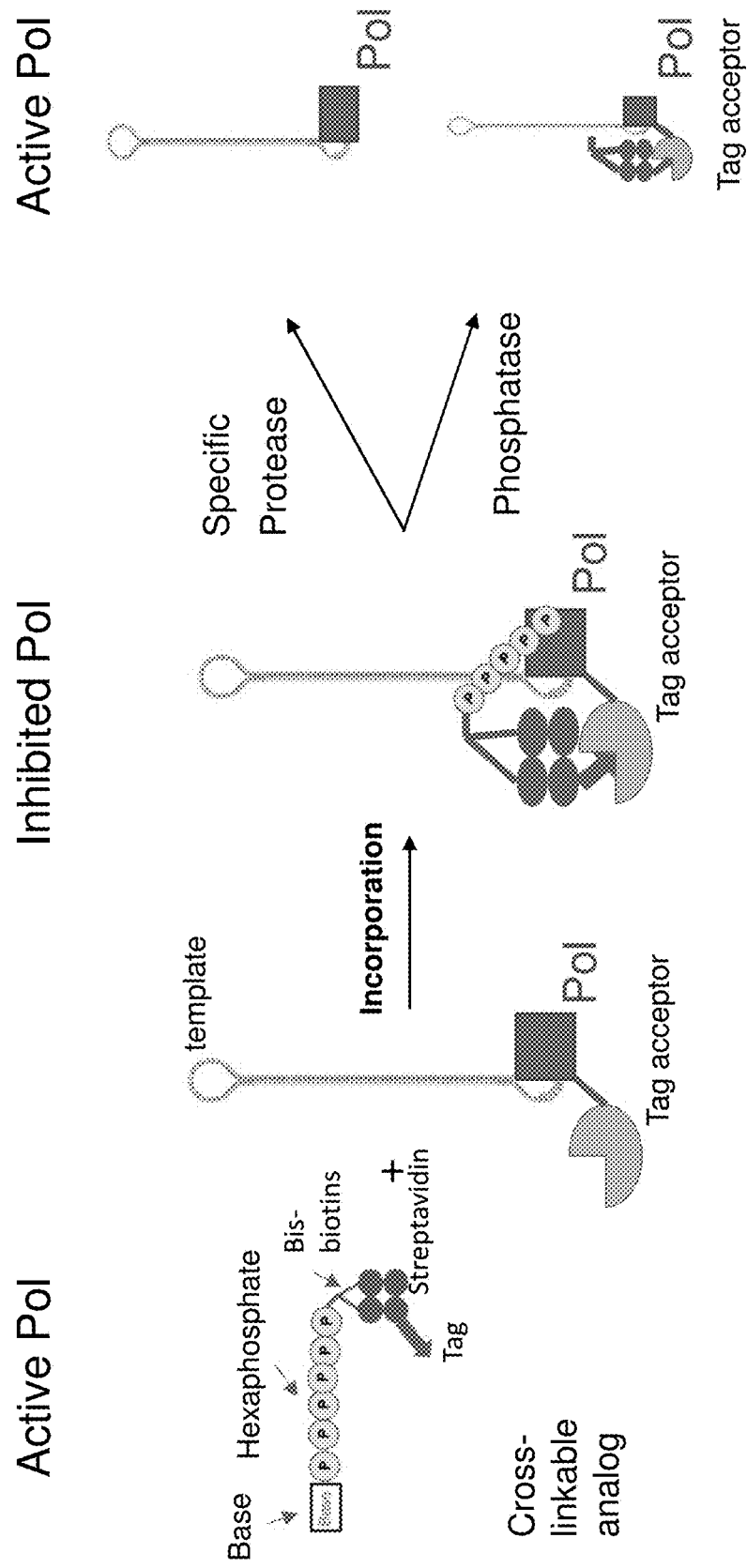
FIG. 16A schematically illustrates production of an inhibited polymerase through incorporation of a nucleotide analog that includes a SpyTagged streptavidin to which the polyphosphate group of the analog is bound, followed by relief of inhibition by application of a phosphatase or protease.

An inhibited polymerase is constructed as outlined in FIG. 16A. A nucleotide analog in which the polyphosphate can be linked to the polymerase is provided. In the analog shown in FIG. 16A, a hexaphosphate nucleotide analog in which the terminal phosphate is bis-biotinylated is bound to a streptavidin tetramer that includes three wild-type monomers and one monomer in which a SpyTag is fused to the C-terminus of the monomer; see also FIG. 16B. For expression of streptavidin and formation of mixed multimers, see, e.g., "Expression of a cloned streptavidin gene in *Escherichia coli*" Proc Natl Acad Sci USA 87:142-6 and Fairhead et al. (2014) "SpyAvidin hubs enable precise and ultrastable orthogonal nanoassembly" J. Am. Chem. Soc. 136: 12355-12363. For discussion of the SpyTag/SpyCatcher and SnoopTag/SnoopCatcher systems, see, e.g., Zakeri et al. (2012) "Peptide tag forming a rapid covalent bond to a protein, through engineering a bacterial adhesin" Proc Natl Acad Sci USA 109(12):E690-7; Fairhead et al. (2014) J. Am. Chem. Soc. 136: 12355-12363; U.S. Pat. No. 9,547,003; Veggiani et al. (2016) "Programmable polyproteams built using twin peptide superglues" Proc Natl Acad Sci USA 113(5):1202-7; and Brune et al. (2017) "Dual Plug-and-Display Synthetic Assembly Using Orthogonal Reactive Proteins for Twin Antigen Immunization" Bioconjugate Chem. 28:1544-1551. Similar untagged analogs are described, e.g., in U.S. patent application publications 2017/0145495, 2017/0145496, and 2017/0321268.

A polymerase fused to a SpyCatcher domain is complexed with a nucleic acid template and primer. When the polymerase complex incorporates the nucleotide analog of FIG. 16B, the SpyTag on the analog can react with the SpyCatcher on the polymerase, stably associating the pentaphosphate product of the incorporation reaction with the polymerase and inhibiting it. Efficient bond formation between the SpyTag and SpyCatcher typically requires a high (e.g., µM) concentration of the reactants. Inhibition of the polymerase can be relieved, e.g., by digesting the polyphosphate with a phosphatase (e.g., CIP) or by removing the polyphosphate with a protease or other agent that cleaves at a site between the polyphosphate and the polymerase.

Figure 16B:
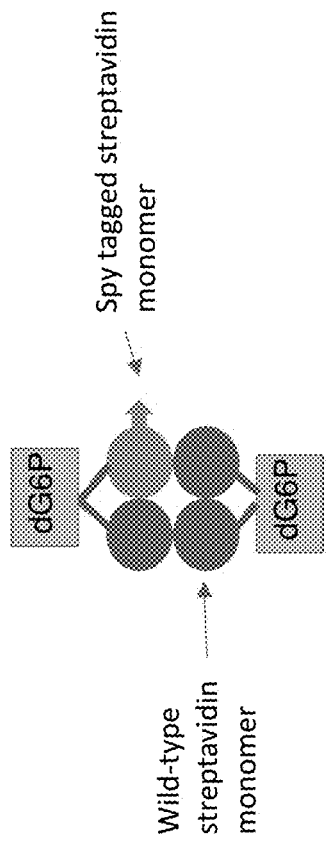
FIG. 16B schematically illustrates a nucleotide analog that includes a SpyTagged streptavidin tetramer to which are bound two deoxyguanosine hexaphosphate moieties bearing a bis-biotin group on the terminal phosphate.
Figure 16C:
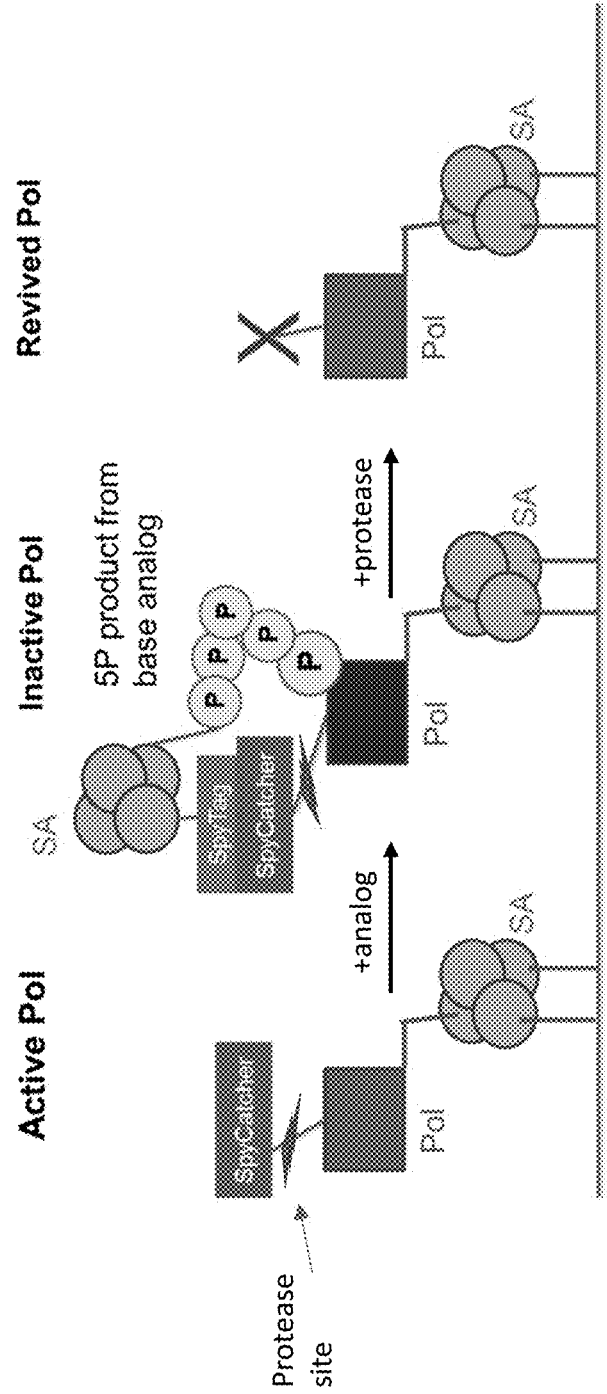
FIG. 16C schematically illustrates production of an inhibited polymerase through incorporation of a nucleotide analog like that of FIG. 16B, followed by relief of inhibition by application of a site-specific protease.

One exemplary polymerase configured for proteolytic removal of the pentaphosphate includes an N-terminal SpyCatcher followed by a specific protease site and the polymerase: SpyCatcher-GGGS-ThrombinSite-GGGS-mutant Φ29 DNA polymerase-GGGSGGGS-BtagV7-BtagV7-glycine-His10 tag. Biotinylation sequences (Btags; see, e.g., U.S. Pat. No. 8,389,676) at the C-terminal end of the polymerase facilitate immobilization of the bis-biotinylated polymerase through streptavidin on a biotinylated surface. GGGS (SEQ ID NO:1) and GGGSGGGS (SEQ ID NO:2) linkers are included for flexibility. Thrombin cleaves at the indicated site in its recognition sequence LVPR/GS (SEQ ID NO:3). Inhibition of this polymerase followed by release of inhibition by thrombin protease digestion is schematically illustrated in FIG. 16C.

Seven polymerase constructs described in Table 1 are produced (e.g., basically as described in U.S. Pat. No. 9,399,766). Constructs 1 and 2 include a SpyCatcher domain but do not include a thrombin site; these domains can be inhibited by incorporation of an analog like that of FIG. 16B, but inhibition cannot be reversed by addition of thrombin. Constructs 3 and 4 include a SpyCatcher domain that is removable by thrombin. Constructs 5 and 6 lack both SpyCatcher and thrombin site. Construct 7 lacks a SpyCatcher domain but includes a thrombin site in the linker between the polymerase and the biotinylation sites used for immobilization (immobilization of the polymerase in the other constructs is not sensitive to thrombin).

TABLE 1

Polymerase constructs

| # | Description | Construct |
|---|---|---|
| 1 | C-terminal SpyCatcher | Phi29 mutant A-GGGSGGGSGGGS-SpyCatcher-GGGSGGGSGGGS-BtagV7-BtagV7-G-His10 |
| 2 | C-terminal SpyCatcher, shorter linker | Phi29 mutant B-GGGS-SpyCatcher-GGGS-BtagV7-BtagV7-G-His10 |
| 3 | N-terminal SpyCatcher, thrombin cleavable | SpyCatcherV2-GGGS-ThrombinSite-GGGS-Phi29 mutant C-GGGSGGGS-BtagV7-BtagV7-G-His10 |
| 4 | C-terminal SpyCatcher, thrombin cleavable | Phi29 mutant C-GGGSGGGS-BtagV7-BtagV7-GGGS-ThrombinSite-GGGS-MSYY-SpyCatcher-G-His10 |
| 5 | Control | Phi29 mutant A-GGGSGGGS-BtagV7-BtagV7-G-His10 |
| 6 | Control | Phi29 mutant C-GGGSGGGS-BtagV7-BtagV7-G-His10 |
| 7 | Thrombin sensitive control | Phi29 mutant C-GGGS-ThrombinSite-GGGS-BtagV7-BtagV7-G-His10 |

Performance of the polymerase constructs is assessed in single molecule sequencing reactions in three stages: initial performance, after incorporation of the analog of FIG. 16B to inhibit polymerases fused to a SpyCatcher domain, and after exposure to thrombin, as follows. The polymerases are formulated with streptavidin and incubated with appropriate nucleic acid primer/templates and used with commercially available reagents for sequencing on a Sequel™ system from Pacific Biosciences of California, following protocols described in the commercial literature. The polymerase formulations are multiplexed on identifiably different templates with similar characteristics (i.e., length and base composition). Data is presented in FIG. 17. An initial 15 minute movie is taken on a single Sequel™ chip with the multiplexed polymerase constructs. The SpyTagged G analog of FIG. 16B is added to the chip (along with untagged A, T, and C analogs) and incorporation is permitted for 90 minutes. A second 15 minute movie is collected from the chip. The chip is then incubated at room temperature for 10 minutes with 1 unit of thrombin in bead binding buffer, and a third 15 minute movie is taken. The active fraction observed for each different construct in each movie is shown in FIG. 17.

Figure 17:
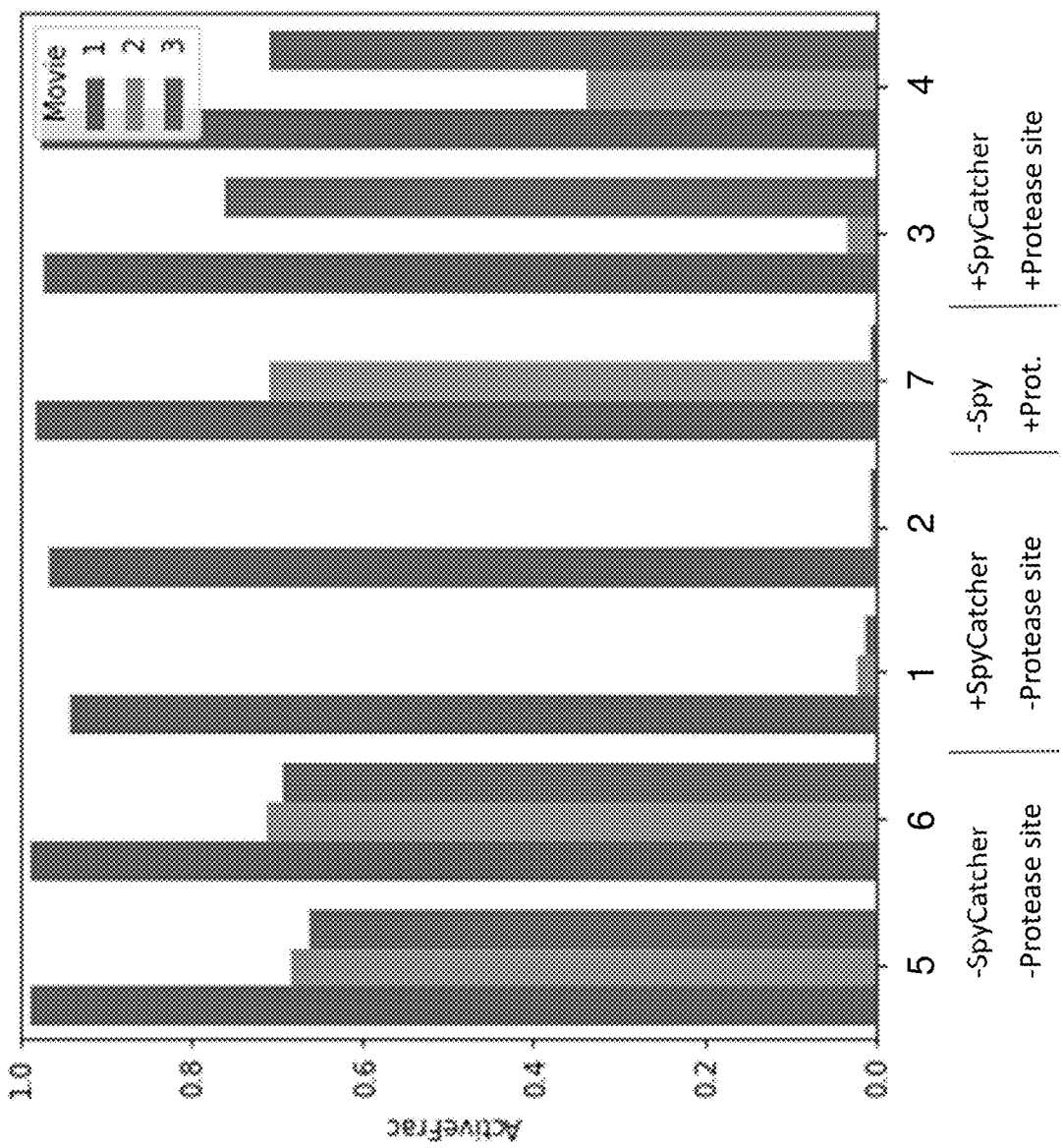
FIG. 17 presents a graph illustrating efficiency of inhibition and revival of various polymerase constructs.

As seen in the data shown in FIG. 17, polymerases including a SpyCatcher domain can be inhibited by incorporation of the analog. Thrombin effectively recovers activity of inhibited polymerases that contain a thrombin site, and does not lead to significant dieoffs of polymerases without a thrombin site (except the thrombin-sensitive control). In addition, inhibition and revival with thrombin does not seem to affect pulse kinetics, accuracy, or read length (data not shown).

Example 5: Tuning Loading Through Polymerase Immobilization

As detailed above, loading level can be adjusted by immobilizing a mixture of polymerases that include linkers cleavable by specific agents and polymerases including non-cleavable linkers, then removing a portion of the complexes as necessary. An exemplary embodiment is illustrated in FIG. 18. A mixture of polymerase complexes with non-cleavable linkers, thrombin-cleavable linkers, and TEV-cleavable linkers is immobilized through binding of bis-biotinylated polymerases to streptavidin tetramers bound to a biotinylated surface (e.g., the bottom of the ZMW). About 30% of the polymerases include a thrombin-cleavable linker and are removed by treatment with thrombin. About 50% of the polymerases include a TEV-cleavable linker; thus, about 80% of the polymerases are removed by treatment with both thrombin and TEV.

To demonstrate the feasibility of this approach, three polymerase constructs are produced, e.g., basically as described in U.S. Pat. No. 9,399,766. All three polymerases include two C-terminal Btags to facilitate immobilization. One construct includes a thrombin site (LVPRGS, SEQ ID NO:3) between the polymerase and the Btags, one includes a TEV site (ENLYFQ, SEQ ID NO:4) between the polymerase and the Btags, and one lacks both sites.

Performance of the polymerase constructs is assessed in single molecule sequencing reactions after immobilization and again after exposure to protease, as follows. The polymerases are formulated with streptavidin and incubated with appropriate nucleic acid primer/templates and used with commercially available reagents for sequencing. The polymerase formulations are multiplexed on identifiably different templates with similar characteristics (i.e., length and base composition). An initial 15 minute movie is taken on a single ZMW chip with the multiplexed polymerase constructs. Protease (thrombin or a mixture of thrombin and TEV) is added to the chip in digestion buffer (50 mM Tris pH 7.5, 100 mM NaCl, 500 nM nucleotide analog mix, and 0.10 mM strontium acetate) and incubated for 20 minutes at room temperature. The chip is washed three times to remove protease, and sequencing buffer is added. A second 15 minute movie is collected from the chip. Data is presented in Table 2. nReads represents the number of ZMWs from which single molecule sequencing data was obtained.

TABLE 2

On-chip digestion data

| polymerase construct | site | template | nReads before thrombin | nReads after thrombin | % Delta |
|---|---|---|---|---|---|
| A | TEV | 1 | 8949 | 8687 | −2.9% |
| B | thrombin | 2 | 12129 | 351 | −97.1% |
| C | | 3 | 18986 | 18379 | −3.2% |

| | | | nReads before thrombin + TEV | nReads after thrombin + TEV | |
|---|---|---|---|---|---|
| A | TEV | 1 | 10228 | 438 | −97.7% |
| B | thrombin | 2 | 13071 | 265 | −98.0% |
| C | | 3 | 21399 | 22560 | +5.4% |

As seen in the data shown in Table 2, polymerases including a thrombin sites are selectively removed by incubation with thrombin, while polymerases including a TEV site are selectively removed by incubation with TEV.

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. All the techniques, compositions, and apparatus described above can be used in various combinations. It is intended that all matter contained in the above description shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

What is claimed is:

1. A method for loading polymerase enzyme complexes into a predetermined number of nanoscale wells, the method comprising:
   (a) providing a surface comprising an array of nanoscale wells;
   (b) contacting a loading solution to the surface, wherein the loading solution comprises:
      (i) one or more nucleotides and/or nucleotide analogs; and
      (ii) polymerase enzyme complexes comprising a template nucleic acid and a polymerase enzyme,
   wherein interactions between the nucleotides and/or nucleotide analogs and the polymerase enzyme complexes result in generation of signal pulses;
   (c) while the loading solution is in contact with the surface, monitoring the array of nanoscale wells to detect signal pulses from within the wells and thereby identifying nanoscale wells that have been loaded with a polymerase enzyme complex; and
   (d) maintaining the loading solution in contact with the surface until the predetermined number of nanoscale wells have been loaded with a polymerase enzyme complex.

2. The method of claim 1, wherein the loading solution comprises one or more labeled nucleotide analogs, wherein the signal pulses are a result of non-incorporation events involving the labeled nucleotide analogs.

3. The method of claim 2, wherein the loading solution comprises one or more additives that maintain the polymerase enzymes in an inactive state.

4. The method of claim 3, wherein the one or more additives comprise a divalent cation selected from the group consisting of strontium, cobalt, tin, calcium, nickel, europium, barium, iron, and zinc.

5. The method of claim 2, wherein the labeled nucleotide analog is a nonhydrolyzable labeled nucleotide analog.

6. The method of claim 1, wherein the array of nanoscale wells is part of a substrate that allows signal pulses to be detected only when a polymerase enzyme complex is within a nanoscale well.

7. The method of claim 1, wherein the template nucleic acids in the polymerase enzyme complexes are hybridized to a primer.

8. The method of claim 1, wherein the predetermined number of nanoscale wells occupied by a polymerase enzyme complex is about 60-80% of the nanoscale wells in the array.

9. The method of claim 1, wherein after the predetermined number of nanoscale wells in the array are occupied by a polymerase enzyme complex, the surface is washed to remove the loading solution.

10. The method of claim 9, wherein after the wash step, the array is prepared for analyzing the polymerase enzyme complexes within the nanoscale wells.

11. The method of 10, wherein the analyzing comprises determining a nucleotide sequence of the template nucleic acid.

12. The method of claim 11, wherein determining the nucleotide sequence comprises (i) providing one or more nucleotides or nucleotide analogs;

(ii) performing a polymerization reaction in which the polymerase enzyme replicates at least a portion of the template nucleic acid in a template-dependent manner, whereby one or more of the nucleotides or nucleotide analogs are incorporated into the resulting nucleic acid; and (iii) identifying a time sequence of incorporation of the one or more nucleotide or nucleotide analogs into the resulting nucleic acid.

13. The method of claim 1, comprising immobilizing the polymerase enzyme complexes within the nanoscale wells.

14. The method of claim 1, wherein the loading solution further comprises at least one agent to mitigate photodamage.

15. The method of claim 14, wherein the at least one agent to mitigate photodamage is selected from the group consisting of a triplet-state quencher, a reducing agent, a singlet oxygen quencher, and an oxygen depleting enzyme.

\* \* \* \* \*